United States Patent [19]
Askew et al.

[11] Patent Number: 6,017,926
[45] Date of Patent: Jan. 25, 2000

[54] INTEGRIN RECEPTOR ANTAGONISTS

[75] Inventors: Ben C. Askew, Lansdale; Paul J. Coleman, Wallingford; Mark E. Duggan, Schwenksville; Wasyl Halczenko, Lansdale; John H. Hutchinson, Philadelphia; Robert S. Meissner, Schwenksville; Michael A. Patane, Harleysville; Jiabing Wang, Lansdale, all of Pa.

[73] Assignee: Merck & Co., Inc., Rahway, N.J.

[21] Appl. No.: 09/212,079

[22] Filed: Dec. 15, 1998

Related U.S. Application Data

[60] Provisional application No. 60/069,910, Dec. 17, 1997, provisional application No. 60/083,251, Apr. 27, 1998, provisional application No. 60/092,588, Jul. 13, 1998, provisional application No. 60/079,197, Mar. 24, 1998, provisional application No. 60/079,944, Mar. 30, 1998, provisional application No. 60/080,397, Apr. 2, 1998, provisional application No. 60/092,624, Jul. 13, 1998, and provisional application No. 60/099,948, Sep. 11, 1998.

[51] Int. Cl.[7] ........................ A61K 31/435; C07D 471/04
[52] U.S. Cl. ........................ 514/300; 514/230.5; 514/300; 514/333; 544/105; 544/335; 546/81; 546/82; 546/122; 546/256; 546/115; 546/118; 548/306.1
[58] Field of Search ........................ 546/122, 256, 546/81, 82; 544/105, 335; 548/306.1; 514/230.5, 333, 303, 300

[56] References Cited

U.S. PATENT DOCUMENTS

| | | | |
|---|---|---|---|
| 5,455,243 | 10/1995 | Duggan et al. | 514/218 |
| 5,668,159 | 9/1997 | Jin et al. | 514/363 |

FOREIGN PATENT DOCUMENTS

| | | |
|---|---|---|
| 051 829 | 5/1982 | European Pat. Off. . |
| 0796 855 A1 | 9/1997 | European Pat. Off. . |
| WO 95/32710 | 7/1995 | WIPO . |
| WO 96/31485 | 10/1996 | WIPO . |
| WO 97/37655 | 10/1997 | WIPO . |
| WO 98/08840 | 3/1998 | WIPO . |
| WO 98/18460 | 5/1998 | WIPO . |
| WO 98/18461 | 5/1998 | WIPO . |
| WO 98/31359 | 7/1998 | WIPO . |

*Primary Examiner*—Bernard Dentz
*Attorney, Agent, or Firm*—Philippe L. Durette; Melvin Winokur; Anthony D. Sabatelli

[57] ABSTRACT

The present invention relates to compounds and derivatives thereof, their synthesis, and their use as integrin receptor antagonists. More particularly, the compounds of the present invention are antagonists of the integrin receptors $\alpha v \beta 3$, $\alpha v \beta 5$ and/or $\alpha v \beta 6$ and are useful for inhibiting bone resorption, treating and preventing osteoporosis, and inhibiting vascular restenosis, diabetic retinopathy, macular degeneration, angiogenesis, atherosclerosis, inflammation, wound healing, viral disease, and tumor growth and metastasis.

48 Claims, No Drawings

INTEGRIN RECEPTOR ANTAGONISTS

CROSS-REFERENCE TO RELATED APPLICATIONS

The present invention is related to U.S. provisional applications Serial No. 60/069,910, filed Dec. 17, 1997; 60/083,251, filed Apr. 27, 1998; 60/092,588, filed Jul. 13, 1998; 60/079,197, filed Mar. 24, 1998; 60/079,944, filed Mar. 30, 1998; 60/080,397, filed Apr. 2, 1998; 60/092,624, filed Jul. 13, 1998; and 60/099,948, filed Sep. 11, 1998; the contents of each of which are hereby incorporated by reference.

FIELD OF THE INVENTION

The present invention relates to compounds and derivatives thereof, their synthesis, and their use as integrin receptor antagonists. More particularly, the compounds of the present invention are antagonists of the integrin receptors $\alpha v\beta 3$, $\alpha v\beta 5$, and/or $\alpha v\beta 6$ and are useful for inhibiting bone resorption, treating and preventing osteoporosis, and inhibiting vascular restenosis, diabetic retinopathy, macular degeneration, angiogenesis, atherosclerosis, inflammation, wound healing, viral disease, tumor growth, and metastasis.

BACKGROUND OF THE INVENTION

It is believed that a wide variety of disease states and conditions can be mediated by acting on integrin receptors and that integrin receptor antagonists represent a useful class of drugs. Integrin receptors are heterodimeric transmembrane proteins through which cells attach and communicate with extracellular matrices and other cells (See S. B. Rodan and G. A. Rodan, "Integrin Function In Osteoclasts", *Journal of Endocrinology*, Vol. 154, S47–S56 (1997), which is incorporated by reference herein in its entirety).

In one aspect of the present invention, the compounds herein are useful for inhibiting bone resorption. Bone resorption is mediated by the action of cells known as osteoclasts. Osteoclasts are large multinucleated cells of up to about 400 mm in diameter that resorb mineralized tissue, chiefly calcium carbonate and calcium phosphate, in vertebrates. Osteoclasts are actively motile cells that migrate along the surface of bone, and can bind to bone, secrete necessary acids and proteases, thereby causing the actual resorption of mineralized tissue from the bone. More specifically, osteoclasts are believed to exist in at least two physiological states, namely, the secretory state and the migratory or motile state. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they again attach to bone.

Integrins are involved in osteoclast attachment, activation and migration. The most abundant integrin in osteoclasts, e.g., in rat, chicken, mouse and human osteoclasts, is an integrin receptor known as $\alpha v\beta 3$, which is thought to interact in bone with matrix proteins that contain the RGD sequence. Antibodies to $\alpha v\beta 3$ block bone resorption in vitro indicating that this integrin plays a key role in the resorptive process. There is increasing evidence to suggest that $\alpha v\beta 3$ ligands can be used effectively to inhibit osteoclast mediated bone resorption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid-induced osteoporosis. All of these conditions are characterized by bone loss, resulting from an imbalance between bone resorption, i.e. breakdown, and bone formation, which continues throughout life at the rate of about 14% per year on the average. However, the rate of bone turnover differs from site to site; for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

In the United States, there are currently about 20 million people with detectable fractures of the vertebrae due to osteoporosis. In addition, there are about 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, $\alpha v\beta 3$ ligands have been found to be useful in treating and/or inhibiting restenosis, i.e. recurrence of stenosis after corrective surgery on the heart valve, atherosclerosis, diabetic retinopathy, macular degeneration, and angiogenesis, i.e. formation of new blood vessels. Moreover, it has been postulated that the growth of tumors depends on an adequate blood supply, which in turn is dependent on the growth of new vessels into the tumor; thus, inhibition of angiogenesis can cause tumor regression in animal models (See *Harrison's Principles of Internal Medicine*, 12th ed., 1991, which is incorporated by reference herein in its entirety). Therefore, $\alpha v\beta 3$ antagonists which inhibit angiogenesis can be useful in the treatment of cancer by inhibiting tumor growth (See e.g., Brooks et al., *Cell*, 79:1157–1164 (1994), which is incorporated by reference herein in its entirety).

Moreover, compounds of this invention can also inhibit neovascularization by acting as antagonists of the integrin receptor, $\alpha v\beta 5$. A monoclonal antibody for $\alpha v\beta 5$ has been shown to inhibit VEGF-induced angiogenesis in rabbit cornea and the chick chorioallantoic membrane model (See M. C. Friedlander, et al., *Science* 270, 1500–1502, (1995), which is incorporated by reference herein in its entirety). Thus, compounds that antagonize $\alpha v\beta 5$ are useful for treating and preventing macular degeneration, diabetic retinopathy, tumor growth, and metastasis.

Additionally, compounds of the instant invention can inhibit angiogenesis and inflammation by acting as antagonists of the integrin receptor, $\alpha v\beta 6$, which is expressed during the later stages of wound healing and remains expressed until the wound is closed (See Christofidou-Solomidou, et al., "Expression and Function of Endothelial Cell $\alpha v$ Integrin Receptors in Wound-Induced Human Angiogenesis in Human Skin/SCID Mice Chimeras, *American Journal of Pathology*, Vol. 151, No. 4, pp. 975–983 (October 1997), which is incorporated by reference herein in its entirety). It is postulated that $\alpha v\beta 6$ plays a role in the remodeling of the vasculature during the later stages of angiogenesis. Also, $\alpha v\beta 6$ participates in the modulation of epithelial inflammation and is induced in response to local injury or inflammation (See Xiao-Zhu Huang, et al., "Inactivation of the Integrin $\beta 6$ Subunit Gene Reveals a Role of Epithelial Integrins in Regulating Inflammation in the Lungs and Skin," *Journal of Cell Biology,* Vol. 133, No.4, pp. 921–928 (May 1996), which is incorporated by reference herein in its entirety). Accordingly, compounds that antagonize αvβ6 are useful in treating or preventing cancer by inhibiting tumor growth and metastasis.

In addition, certain compounds of this invention antagonize both the αvβ3 and αvβ5 receptors. These compounds, referred to as "dual αvβ3/αvβ5 antagonists," are useful for inhibiting bone resorption, treating and preventing osteoporosis, and inhibiting vascular restenosis, diabetic retinopathy, macular degeneration, angiogenesis, atherosclerosis, inflammation, tumor growth, and metastasis.

In addition, certain compounds of this invention are useful as mixed αvβ3, αvβ5, and αvβ6 receptor antagonists.

It is therefore an object of the present invention to provide compounds which are useful as integrin receptor antagonists.

It is another object of the present invention to provide compounds which are useful as αvβ3 receptor antagonists.

It is another object of the present invention to provide compounds which are useful as αvβ5 receptor antagonists.

It is another object of the present invention to provide compounds which are useful as αvβ6 receptor antagonists.

It is another object of the present invention to provide compounds which are useful as dual αvβ3/αvβ5 receptor antagonists.

It is another object of the present invention to provide compounds which are useful as mixed αvβ3, αvβ5, and αvβ6 receptor antagonists.

It is another object of the present invention to provide pharmaceutical compositions comprising integrin receptor antagonists.

It is another object of the present invention to provide methods for making the pharmaceutical compositions of the present invention.

It is another object of the present invention to provide methods for eliciting an integrin receptor antagonizing effect in a mammal in need thereof by administering the compounds and pharmaceutical compositions of the present invention.

It is another object of the present invention to provide compounds and pharmaceutical compositions useful for inhibiting bone resorption, restenosis, atherosclerosis, inflammation, viral disease, diabetic retinopathy, macular degeneration, angiogenesis, tumor growth, and metastasis.

It is another object of the present invention to provide compounds and pharmaceutical compositions useful for treating osteoporosis.

It is another object of the present invention to provide methods for inhibiting bone resorption, restenosis, atherosclerosis, inflammation, viral disease, diabetic retinopathy, macular degeneration, angiogenesis, tumor growth, and metastasis.

It is another object of the present invention to provide methods for treating osteoporosis.

These and other objects will become readily apparent from the detailed description which follows.

SUMMARY OF THE INVENTION

The present invention relates to compounds having a structural formula selected from the group consisting of

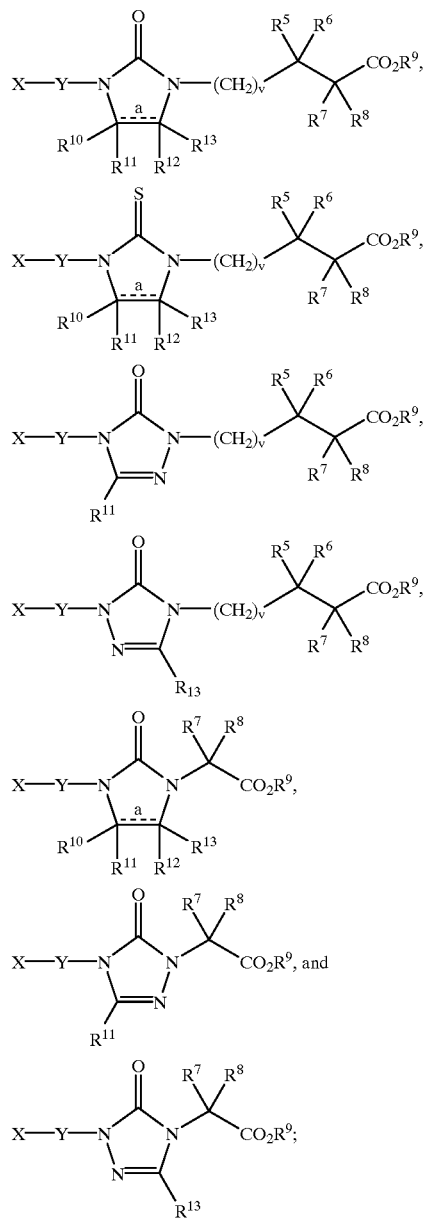

wherein the dotted line a represents a single or a double bond, provided that when a represents a double bond, the double bond carbon atoms are substituted only with $R^{10}$ and $R^{12}$;

X is selected from the group consisting of

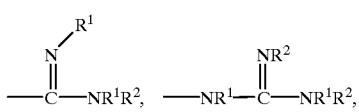

a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

Y is selected from the group consisting of
—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^4$—$(CH_2)_p$—,
—$(CH_2)_m$—$NR^4$—$(CH_2)_n$—$NR^4$—$(CH_2)_p$—,
—$(CH_2)_m$—O—$(CH_2)_n$—S—$(CH_2)_p$—,
—$(CH_2)_m$—S—$(CH_2)_n$—S—$(CH_2)_p$—,
—$(CH_2)_m$—$NR^4$—$(CH_2)_n$—S—$(CH_2)_p$—,
—$(CH_2)_m$—$NR^4$—$(CH_2)_n$—O—$(CH_2)_p$—,
—$(CH_2)_m$—S—$(CH_2)_n$—O—$(CH_2)_p$—,
—$(CH_2)_m$—S—$(CH_2)_n$—$NR^4$—$(CH_2)_p$—, and
—$(CH_2)_m$—Z—$(CH_2)_n$—, wherein Z is a 3- to 10-membered monocyclic or polycyclic aromatic or nonaromatic ring system having 0, 1, 2, 3, or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and wherein any methylene ($CH_2$) carbon atom in Y, other than in $R^4$, can be substituted by one or two $R^3$ substituents; and wherein $R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkloxy-$C_{1-6}$ alkyl, nitro, cyano, trifluoromethyl, trifluoromethoxy, trifluoroethoxy, $C_{1-8}$ alkyl-$S(O)_p$, $(C_{1-8}$ alkyl$)_p$aminocarbonyl, $C_{1-8}$ alkyloxycarbonylamino, $(C_{1-8}$ alkyl$)_p$aminocarbonyloxy, (aryl $C_{1-8}$ alkyl$)_p$amino, (aryl$)_p$amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of
hydrogen,
aryl,
$C_{1-10}$ alkyl,
aryl-$(CH_2)_r$—O—$(CH_2)_s$—;
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino, $C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or two $R^3$ substituents, when on the same carbon atom, are taken together with the carbon atom to which they are attached to form a carbonyl group or a cyclopropyl group,
wherein any of the alkyl groups of $R^3$ are either unsubstituted or substituted with one to three $R^1$ substituents, and provided that each $R^3$ is selected such that in the resultant compound the carbon atom or atoms to which $R^3$ is attached is itself attached to no more than one heteroatom;
each $R^4$ is independently selected from the group consisting of
hydrogen,
aryl,
aminocarbonyl,
$C_{3-8}$ cycloalkyl,
amino $C_{1-6}$ alkyl,
(aryl$)_p$aminocarbonyl,
(aryl $C_{1-5}$ alkyl$)_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
(aryl$)_p$aminosulfonyl,
(aryl $C_{1-8}$ alkyl$)_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of R4 are either unsubstituted or substituted with one to three $R^1$ substituents;
$R^5$ and $R^6$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-SO$_2$—$(CH_2)_t$—, $C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl;
or $R^5$ and $R^6$ are taken together with the carbon atom to which they are attached to form a carbonyl group,
wherein any of the alkyl groups of $R^5$ or $R^6$ are either unsubstituted or substituted with one to three $R^1$ substituents,
and provided that each $R^5$ and $R^6$ are selected such that in the resultant compound the carbon atom to which $R^5$ and $R^6$ are attached is itself attached to no more than one heteroatom;
$R^7$ and $R^8$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N(R$^4$)—$(CH_2)_s$—,
aryl-$(CH_2)_r$—N(R$^4$)—C(O)—$(CH_2)_s$—,
aryl-$(CH_2)_r$—N(R$^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡-C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino, (aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
arylaminocarbonylamino,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl,
(aryl $C_{1-8}$ alkyl)$_p$aminocarbonyl $C_{1-6}$ alkyl, and
$C_{7-20}$ polycyclyl $C_{0-8}$ alkylsulfonylamino;
wherein any of the alkyl groups of $R^7$ and $R^8$ are either unsubstituted or substituted with one to three $R^1$ substituents,
and provided that each $R^7$ and $R^8$ are selected such that in the resultant compound the carbon atom to which $R^7$ and $R^8$ are attached is itself attached to no more than one heteroatom;

$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;
$R^{10}$, $R^{11}$, $R^{12}$ and $R^{13}$ are each independently selected from the group consisting of
hydrogen,
$C_{1-8}$ alkyl,
aryl,
halogen,
hydroxyl,
aminocarbonyl,
$C_{3-8}$ cycloalkyl,
amino $C_{1-6}$ alkyl,
(aryl)$_p$aminocarbonyl,
hydroxycarbonyl,
(aryl $C_{1-5}$ alkyl)$_p$aminocarbonyl,
hydroxycarbonyl $C_{1-6}$ alkyl,
aryl $C_{1-6}$ alkyl,
($C_{1-6}$ alkyl)$_p$amino $C_{1-6}$ alkyl,
(aryl $C_{1-6}$ alkyl)$_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
($C_{1-8}$ alkyl)$_p$aminocarbonyl,
aminosulfonyl,
$C_{1-8}$ alkylaminosulfonyl,
(aryl)$_p$aminosulfonyl,
(aryl $C_{1-8}$ alkyl)$_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—, $C_{1-6}$ alkyl-CH=CH-(CH$_2$)$_t$-,
$C_{3-7}$ cycloalkyl-CH=CH-(CH$_2$)$_t$-,
aryl-CH=CH-(CH$_2$)$_t$-,
$C_{1-6}$ alkylaryl-CH=CH-(CH$_2$)$_t$-,
$C_{1-6}$ alkyl-SO$_2$-(CH$_2$)$_t$-,
$C_{1-6}$ alkylaryl-SO$_2$-(CH$_2$)$_t$-,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
($C_{1-6}$ alkyl)$_p$amino,
aminocarbonyl $C_{1-6}$ alkyl,
$C_{1-6}$ alkoxy,
aryl $C_{1-6}$ alkoxy,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl; or
$R^{10}$ and $R^{12}$ are taken together with the carbon atoms to which they are attached to form a 5- to 7-membered monocyclic aromatic or nonaromatic ring system having 0, 1, 2, 3, or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents,
and wherein any of the alkyl groups of $R^{10}$, $R^{11}$, $R^{12}$, and $R^{13}$ are either unsubstituted or substituted with one to three $R^1$ substituents;
wherein
each m is independently an integer from 0 to 6;
each n is independently an integer from 0 to 6
each p is independently an integer from 0 to 2;
each r is independently an integer from 1 to 3;
each s is independently an integer from 0 to 3;
each t is independently an integer from 0 to 3; and
each v is independently an integer from 0 to 2;
and the pharmaceutically acceptable salts thereof.

The present invention also relates to pharmaceutical compositions comprising the compounds of the present invention and a pharmaceutically acceptable carrier.

The present invention also relates to methods for making the pharmaceutical compositions of the present invention.

The present invention also relates to methods for eliciting an integrin receptor antagonizing effect in a mammal in need thereof by administering the compounds and pharmaceutical compositions of the present invention.

The present invention also relates to methods for inhibiting bone resorption, restenosis, atherosclerosis, inflammation, viral disease, diabetic retinopathy, macular degeneration, angiogenesis, wound healing, tumor growth, and metastasis by administering the compounds and pharmaceutical compositions of the present invention.

The present invention also relates to methods for treating osteoporosis by administering the compounds and pharmaceutical compositions of the present invention.

DETAILED DESCRIPTION OF THE INVENTION

The present invention relates to compounds useful as integrin receptor antagonists. Compounds of the present invention are described by the following structural formulas selected from the group consisting of

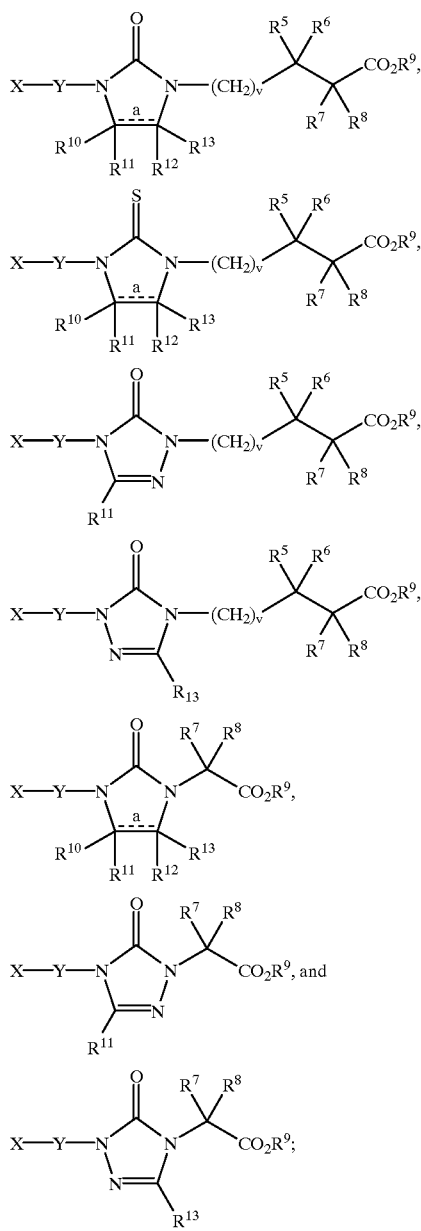

wherein the dotted line a represents a single or a double bond, provided that when a represents a double bond, the double bond carbon atoms are substituted only with $R^{10}$ and $R^{12}$;

X is selected from the group consisting of

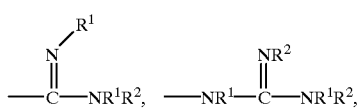

a 5- or 6-membered monocyclic aromatic or nonaromatic ring system having 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

Y is selected from the group consisting of

—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^4$—$(CH_2)_p$—,
—$(CH_2)_m$—$NR^4$—$(CH_2)_n$—$NR^4$—$(CH_2)_p$—,
—$(CH_2)_m$—O—$(CH_2)_n$—S—$(CH_2)_p$—,
—$(CH_2)_m$—S—$(CH_2)_n$—S—$(CH_2)_p$—,
—$(CH_2)_m$—$NR^4$—$(CH_2)_n$—S—$(CH_2)_p$—,
—$(CH_2)_m$—$NR^4$—$(CH_2)_n$—O—$(CH_2)_p$—,
—$(CH_2)_m$—S—$(CH_2)_n$—O—$(CH_2)_p$—,
—$(CH_2)_m$—S—$(CH_2)_n$—$NR^4$—$(CH_2)_p$—, and
—$(CH_2)_m$—Z—$(CH_2)_n$—, wherein Z is a 3- to 10-membered monocyclic or polycyclic aromatic or nonaromatic ring system having 0, 1, 2, 3, or 4 heteroatoms selected from the group consisting of N, O, and S wherein the 3- to 10-membered monocyclic or polycyclic aromatic or nonaromatic ring system is either unsubstituted or substituted with one or two $R^1$ substituents, and wherein any methylene ($CH_2$) carbon atom in Y, other than in $R^4$, can be substituted by one or two $R^3$ substituents; and wherein $R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, ($C_{1-6}$ alkyl)$_p$amino, ($C_{1-6}$ alkyl)$_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_p$, ($C_{1-8}$ alkyl)$_p$aminocarbonyl, $C_{1-8}$ alkyloxycarbonylamino, ($C_{1-8}$ alkyl)$_p$aminocarbonyloxy, (aryl $C_{1-8}$ alkyl)$_p$amino, (aryl)$_p$amino, aryl $C_{1-8}$ alkylsulfonylamino, and $C_{1-8}$ alkylsulfonylamino;

or two $R^1$ substituents, when on the same carbon atom, are taken together to form a carbonyl group;

each $R^3$ is independently selected from the group consisting of hydrogen,
aryl,
$C_{1-10}$ alkyl,
aryl-$(CH_2)_r$—O—$(CH_2)_s$—,
aryl-$(CH_2)_r$$S(O)_p$—$(CH_2)_s$—,
aryl-$(CH_2)_r$—C(O)—$(CH_2)_s$—,
aryl-$(CH_2)_r$—C(O)—$N(R^4)$—$(CH_2)_s$—, aryl-(CH$_2$)$_r$—N(R$^4$)—C(O)—(CH$_2$)$_s$—,
aryl-(CH$_2$)$_r$—N(R$^4$)—(CH$_2$)$_s$—,
halogen,
hydroxyl,
oxo,
trifluoromethyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl,
hydroxycarbonyl,
hydroxycarbonyl C$_{1-6}$ alkyl,
HC≡C—(CH$_2$)$_t$—,
C$_{1-6}$ alkyl-C≡C—(CH$_2$)$_t$—,
C$_{3-7}$ cycloalkyl-C≡C—(CH$_2$)$_t$—,
aryl-C≡C—(CH$_2$)$_t$—,
C$_{1-6}$ alkylaryl-C≡C—(CH$_2$)$_t$—,
CH$_2$=CH—(CH$_2$)$_t$—,
C$_{1-6}$ alkyl-CH=CH—(CH$_2$)$_t$—,
C$_{3-7}$ cycloalkyl-CH=CH—(CH$_2$)$_t$—,
aryl-CH=CH—(CH$_2$)$_t$—,
C$_{1-6}$ alkylaryl-CH=CH—(CH$_2$)$_t$—,
C$_{1-6}$ alkyl-SO$_2$—(CH$_2$)$_t$—,
C$_{1-6}$ alkylaryl-SO$_2$—(CH$_2$)$_t$—,
C$_{1-6}$ alkoxy,
aryl C$_{1-6}$ alkoxy,
aryl C$_{1-6}$ alkyl,
(C$_{1-6}$ alkyl)$_p$amino C$_{1-6}$ alkyl,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl$_p$aminocarbonyloxy,
C$_{1-8}$ alkylsulfonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;
or two R$^3$ substituents, when on the same carbon atom, are taken together with the carbon atom to which they are attached to form a carbonyl group or a cyclopropyl group,
wherein any of the alkyl groups of R$^3$ are either unsubstituted or substituted with one to three R$^1$ substituents, and provided that each R$^3$ is selected such that in the resultant compound the carbon atom or atoms to which R$^3$ is attached is itself attached to no more than one heteroatom;
each R$^4$ is independently selected from the group consisting of
hydrogen,
aryl,
aminocarbonyl,
C$_{3-8}$ cycloalkyl,
amino C$_{1-6}$ alkyl,
(aryl)$_p$aminocarbonyl,
(aryl C$_{1-5}$ alkyl)$_p$aminocarbonyl,
hydroxycarbonyl C$_{1-6}$ alkyl,
C$_{1-8}$ alkyl,
aryl C$_{1\ 6}$ alkyl,
(C$_{1-6}$ alkyl)$_p$amino C$_{2-6}$ alkyl,
(aryl C$_{1-6}$ alkyl)$_p$amino C$_{2-6}$ alkyl,
C$_{1-8}$ alkylsulfonyl, $C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
amino sulfonyl,
$C_{1-8}$ alkylaminosulfonyl,
(aryl)$_p$aminosulfonyl,
(aryl $C_{1-8}$ alkyl)$_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl,
wherein any of the alkyl groups of $R^4$ are either unsubstituted or substituted with one to three $R^1$ substituents;
R5 and $R^6$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N(R$^4$)—$(CH_2)_s$—,
aryl-$(CH_2)_r$—N(R$^4$)—C(O)—$(CH_2)_s$—,
aryl-$(CH_2)_r$—N(R$^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-SO$_2$—$(CH_2)_t$—,
$C_{1-6}$ alkylaryl-SO$_2$—$(CH_2)_t$—, $C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl)$_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl)$_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl)$_p$aminocarbonyl $C_{1-6}$ alkyl, (aryl $C_{1-8}$ alkyl)$_p$aminocarbonyl, and
(aryl $C_{1-8}$ alkyl)$_p$aminocarbonyl $C_{1-6}$ alkyl;
or R5 and $R^6$ are taken together with the carbon atom to which they are attached to form a carbonyl group,
wherein any of the alkyl groups of $R^5$ or $R^6$ are either unsubstituted or substituted with one to three $R^1$ substituents,
and provided that each $R^5$ and $R^6$ are selected such that in the resultant compound the carbon atom to which $R^5$ and $R^6$ are attached is itself attached to no more than one heteroatom;
$R^7$ and $R^8$ are each independently selected from the group consisting of
hydrogen,
$C_{1-10}$ alkyl,
aryl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
$C_{3-8}$ cycloalkyl,
($C_{1-6}$ alkyl)$_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl-C≡C—$(CH_2)_t$—,
$C_{3-7}$ cycloalkyl-C≡C—$(CH_2)_t$—,
aryl-C≡C—$(CH_2)_t$—,
$C_{1-6}$ alkylaryl-C≡C—$(CH_2)_t$—,
$CH_2$=CH—$(CH_2)_t$—,
$C_{1-6}$ alkyl-CH=CH—$(CH_2)_t$—,
$C_{3-7}$ cycloalkyl-CH=CH—$(CH_2)_t$—,
aryl-CH=CH—$(CH_2)_t$—,
$C_{1-6}$ alkylaryl-CH=CH—$(CH_2)_t$—,
$C_{1-6}$ alkyl-$SO_2$—$(CH_2)_t$—,
$C_{1-6}$ alkylaryl-$SO_2$—$(CH_2)_t$—,
$C_{1-6}$ alkoxy,
aryl $C_{1-6}$ alkoxy,
aryl $C_{1-6}$ alkyl,
($C_{1-6}$ alkyl)$_p$amino $C_{1-6}$ alkyl,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl,
(aryl $C_{1-8}$ alkyl)$_p$aminocarbonyl $C_{1-6}$ alkyl, and
$C_{7-20}$ polycyclyl $C_{0-8}$ alkylsulfonylamino;
wherein any of the alkyl groups of $R^7$ and $R^8$ are either unsubstituted or substituted with one to three $R^1$ substituents, and provided that each $R^7$ and $R^8$ are selected such that in the resultant compound the carbon atom to which $R^7$ and R8 are attached is itself attached to no more than one heteroatom;

$R^9$ is selected from the group consisting of
hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;

$R^{10}$, $R^{11}$, $R^{12}$ and $R^{13}$ are each independently selected from the group consisting of
hydrogen,
$C_{1-8}$ alkyl,
aryl,
halogen,
hydroxyl,
aminocarbonyl,
$C_{3-8}$ cycloalkyl,
amino $C_{1-6}$ alkyl,
$(aryl)_p$aminocarbonyl,
hydroxycarbonyl,
$(aryl\ C_{1-5}\ alkyl)_p$aminocarbonyl,
hydroxycarbonyl $C_{1-6}$ alkyl,
aryl $C_{1-6}$ alkyl,
$(C_{1-6}\ alkyl)_p$amino $C_{1-6}$ alkyl,
$(aryl\ C_{1-6}\ alkyl)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}\ alkyl)_p$aminocarbonyl,
aminosulfonyl,
$C_{1-8}$ alkylaminosulfonyl,
$(aryl)_p$aminosulfonyl,
$(aryl\ C_{1-8}\ alkyl)_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl-$(CH_2)_r$—O—$(CH_2)_s$—,
aryl-$(CH_2)_r$S(O)$_p$—$(CH_2)_s$—,
aryl-$(CH_2)_r$—C(O)—$(CH_2)_s$—,
aryl-$(CH_2)_r$—C(O)—N($R^4$)—$(CH_2)_s$—,
aryl-$(CH_2)_r$—N($R^4$)—C(O)—$(CH_2)_s$—,
aryl-$(CH_2)_r$—N($R^4$)—$(CH_2)_s$—,
HC≡C—$(CH_2)_r$—,
$C_{1-6}$ alkyl-C≡C—$(CH_2)_r$—,
$C_{3-7}$ cycloalkyl-C≡C—$(CH_2)_r$—,
aryl-C≡C—$(CH_2)_r$—,
$C_{1-6}$ alkylaryl-C≡C—$(CH_2)_r$—,
$CH_2$=CH—$(CH_2)_r$—,
$C_{1-6}$ alkyl-CH=CH—$(CH_2)_r$—,
$C_{3-7}$ cycloalkyl-CH=CH—$(CH_2)_r$—,
aryl-CH=CH—$(CH_2)_r$—,
$C_{1-6}$ alkylaryl-CH=CH—$(CH_2)_r$—,
$C_{1-6}$ alkyl-SO$_2$—$(CH_2)_r$—,
$C_{1-6}$ alkylaryl-SO$_2$—$(CH_2)_r$—,
$C_{1-8}$ alkylcarbonylamino,
aryl $C_{1-5}$ alkoxy,
$C_{1-5}$ alkoxycarbonyl,
$(C_{1-8}\ alkyl)_p$aminocarbonyl,
$C_{1-6}$ alkylcarbonyloxy,
$(C_{1-6}\ alkyl)_p$amino,
aminocarbonyl $C_{1-6}$ alkyl,
$C_{1-6}$ alkoxy,
aryl $C_{1-6}$ alkoxy,
$(aryl)_p$amino,
$(aryl)_p$amino $C_{1-6}$ alkyl,
$(aryl\ C_{1-6}\ alkyl)_p$amino,
$(aryl\ C_{1-6}\ alkyl)_p$amino $C_{1-6}$ alkyl,
arylcarbonyloxy,
aryl $C_{1-6}$ alkylcarbonyloxy,
$(C_{1-6}\ alkyl)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}\ alkyl)_p$aminocarbonylamino,
$(C_{1-8}\ alkyl)_p$aminocarbonylamino $C_{1-6}$ alkyl,
$(aryl)_p$aminocarbonylamino $C_{1-6}$ alkyl,
$(aryl\ C_{1-8}\ alkyl)_p$aminocarbonylamino,
$(aryl\ C_{1-8}\ alkyl)_p$aminocarbonylamino $C_{1-6}$ alkyl,
aminosulfonylamino $C_{1-6}$ alkyl,
$(C_{1-8}\ alkyl)_p$aminosulfonylamino,
$(C_{1-8}\ alkyl)_p$aminosulfonylamino $C_{1-6}$ alkyl,
$(aryl)_p$aminosulfonylamino $C_{1-6}$ alkyl,
$(aryl\ C_{1-8}\ alkyl)_p$aminosulfonylamino,
$(aryl\ C_{1-8}\ alkyl)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl, $C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
(aryl$)_p$aminocarbonyl $C_{1-6}$ ally,
(aryl $C_{1-8}$ alkyl$)_p$aminocarbonyl, and
(aryl $C_{1-8}$ alkyl$)_p$aminocarbonyl $C_{1-6}$ alkyl; or
$R^{10}$ and $R^{12}$ are taken together with the carbon atoms to which they are attached to form a 5- to 7-membered monocyclic aromatic or nonaromatic ring system having 0, 1, 2, 3, or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents,
and wherein any of the alkyl groups of $R^{10}$, $R^{11}$, $R^{12}$, and $R^{13}$ are either unsubstituted or substituted with one to three $R^1$ substituents;
wherein
each m is independently an integer from 0 to 6;
each n is independently an integer from 0 to 6
each p is independently an integer from 0 to 2;
each r is independently an integer from 1 to 3;
each s is independently an integer from 0 to 3;
each t is independently an integer from 0 to 3; and
each v is independently an integer from 0 to 2;
and the pharmaceutically acceptable salts thereof In one embodiment of the present invention, compounds are described by the following structural formulas selected from the group consisting of

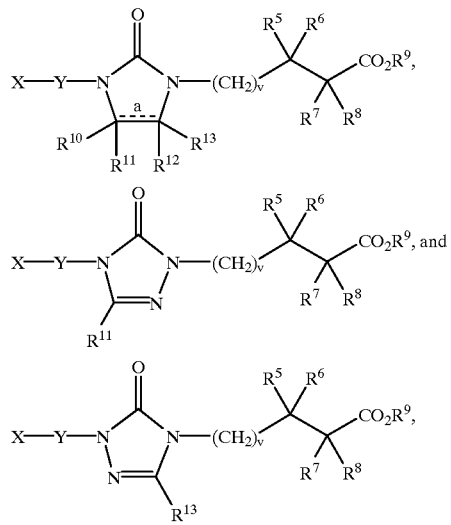

wherein the dotted line a represents a single or a double bond, provided that when a represents a double bond, the double bond carbon atoms are substituted only with $R^{10}$ and $R^{12}$.

In a class of this embodiment of the present invention, compounds are described by the following structural formula

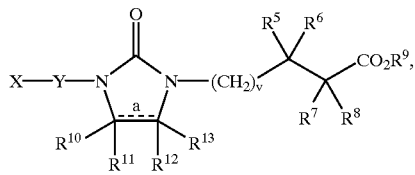

wherein the dotted line a represents a single or a double bond, provided that when a represents a double bond, the double bond carbon atoms are substituted only with $R^{10}$ and R12.

In a subclass of this class of the present invention, compounds are described by the following structural formula

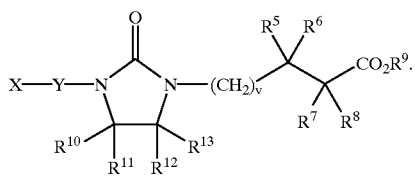

In the compounds of the present invention, X is preferably a 6-membered monocyclic aromatic ring system having 1 or 2 nitrogen atoms wherein each ring carbon atom is unsubstituted or substituted with one $R^1$ substituent, or a 9- to 14membered polycyclic ring system, wherein one or more of the rings is aromatic, and wherein the polycyclic ring system has 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents.

More preferably, X is selected from the group consisting of

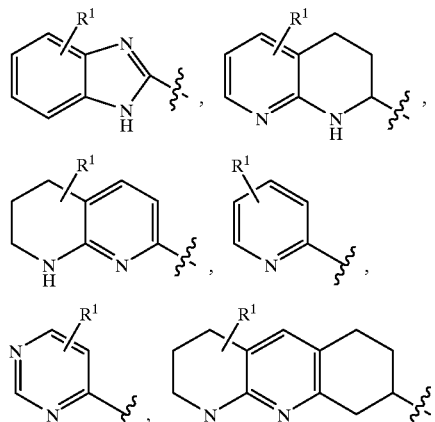

and

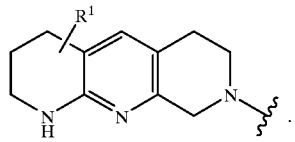

Most preferably X is

[chemical structures with R¹ substituents]

, or

In the compounds of the present invention, Y is preferably selected from the group consisting of —(CH$_2$)$_m$—,
—(CH$_2$)$_m$—O—(CH$_2$)$_n$—,
—(CH$_2$)$_m$—NR$^4$—(CH$_2$)$_n$—,
—(CH$_2$)$_m$—S—(CH$_2$)$_n$—,
—(CH$_2$)$_m$—SO—(CH$_2$)$_n$—,
—(CH$_2$)$_m$—SO$_2$—(CH$_2$)$_n$—,
—(CH2)m—O—(CH2)n—O—(CH2)p—,
—(CH2)m—O—(CH2)n—NR$^4$—(CH2)p—,
—(CH2)m—NR$^4$—(CH2)n—NR$^4$—(CH2)p—, and
—(CH2)m—NR$^4$—(CH2)n—O—(CH2)p—, wherein any methylene (CH2) carbon atom in Y, other than in R$^4$, can be substituted by one or two R$^3$ substituents.

More preferably Y is selected from the group consisting of (CH$_2$)$_m$, (CH$_2$)$_m$—S—(CH$_2$)$_n$, and (CH$_2$)$_m$—NR$^4$—(CH$_2$)$_n$, wherein any methylene (CH$_2$) carbon atom in Y, other than in R$^4$, can be substituted by one or two R$^3$ substituents.

Most preferably Y is (CH$_2$)$_m$ or (CH$_2$)$_m$—NR$^4$—(CH$_2$)$_n$ wherein any methylene (CH$_2$) carbon atom in Y, other than R$^4$, can be substituted by one or two R3 substituents.

In the compounds of the present invention, R$^1$ and R$^2$ are preferably selected from the group consisting of hydrogen, halogen, C$_{1-10}$ alkyl, C$_{3-8}$ cycloalkyl, C$_{3-8}$ cycloheteroalkyl, hydroxy, nitro, cyano, trifluoromethyl, and trifluoromethoxy.

More preferably, R$^1$ and R2 are selected from the group consisting of hydrogen, halogen, C$_{1-10}$ alkyl, C$_{3-8}$ cycloalkyl, trifluoromethyl, and trifluoromethoxy.

In the compounds of the present invention, R$^3$ is preferably selected from the group consisting of hydrogen,
fluoro,
trifluoromethyl,
aryl,
C$_{1-8}$ alkyl,
arylC$_{1-6}$ alkyl
hydroxyl,
oxo,
arylaminocarbonyl,
aryl C$_{1-5}$ alkylaminocarbonyl,
aminocarbonyl, and
aminocarbonyl C$_{1-6}$ alkyl.

More preferably, R$^3$ is selected from the group consisting of fluoro,
aryl,
C$_{1-8}$ alkyl,
arylC$_{1-6}$ alkyl
hydroxyl,
oxo, and
arylaminocarbonyl.

In the compounds of the present invention, R$^4$ is preferably selected from the group consisting of hydrogen,
aryl,
C$_{3-8}$ cycloalkyl,
C$_{1-8}$ alkyl,
C$_{1-8}$ alkylcarbonyl,
arylcarbonyl,
C$_{1-6}$ alkylsulfonyl,
arylsulfonyl,
arylC$_{1-6}$alkylsulfonyl,
arylC$_{1-6}$alkylcarbonyl,
C$_{1-8}$alkylaminocarbonyl,
arylC$_{1-5}$alkylaminocarbonyl,
arylC$_{1-8}$alkoxycarbonyl, and
C$_{1-8}$alkoxycarbonyl.

More preferably, R$^4$ is selected from the group consisting of hydrogen,
C$_{1-8}$ alkyl,
C$_{1-8}$ alkylcarbonyl,
arylcarbonyl,
arylC$_{1-6}$alkylcarbonyl,
C$_{1-6}$ alkylsulfonyl,
arylsulfonyl, and
arylC$_{1-6}$alkylsulfonyl.

In one embodiment of the present invention, R$^5$ and R$^6$ are each independently selected from the group consisting of hydrogen,
aryl,
C$_{1-8}$ alkyl,
aryl-C≡C—(CH$_2$)$_t$—,
aryl C$_{1-6}$ alkyl,
CH$_2$=CH—(CH$_2$)$_t$—, and
HC≡C—(CH$_2$)$_t$—.

In a class of this embodiment of the present invention, R$^6$ is hydrogen and R$^5$ is selected from the group consisting of hydrogen,
aryl,
C$_{1-8}$ alkyl,
aryl-C≡C—(CH$_2$)$_t$—,
aryl C$_{1-6}$ alkyl,
CH2=CH—(CH$_2$)$_t$—, and
HC≡C—(CH$_2$)$_t$—.

In a subclass of this class of the present invention, R$^6$, R$^7$, and R$^8$ are each hydrogen and R$^5$ is selected from the group consisting of hydrogen,
aryl,
C$_{1-8}$ alkyl,
aryl-C≡C—(CH$_2$)$_t$—,
aryl C$_{1-6}$ alkyl, $CH_2=CH-(CH_2)_t-$, and
$HC\equiv C-(CH_2)_t-$.

In another embodiment of the present invention, $R^7$ and $R^8$ are each independently selected from the group consisting of
hydrogen,
aryl,
$C_{1-8}$ alkylcarbonylamino,
arylcarbonylamino,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

In a class of this embodiment of the present invention, $R^8$ is hydrogen and $R^7$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

In a subclass of this class of the present invention, $R^5$, $R^6$, and $R^8$ are each hydrogen and $R^7$ is selected from the group consisting of
hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

In the compounds of the present invention, $R^9$ is preferably selected from the group consisting of hydrogen, methyl, and ethyl.

More preferably, $R^9$ is hydrogen.

In the compounds of the present invention, $R^{10}$, $R^{11}$, $R^{12}$, and $R^{13}$ are preferably each independently selected from the group consisting of hydrogen, aryl, $C_{1-6}$ alkyl, and aryl$C_{1-6}$ alkyl.

In the compounds of the present invention, m is preferably an integer from 0 to 4, and more preferably from 0 to 3.

In the compounds of the present invention, n is preferably an integer from 0 to 4, more preferably from 0 to 3.

In the compounds of the present invention, r is preferably an integer from 1 to 2.

In the compounds of the present invention, s is preferably an integer from 0 to 2.

In the compounds of the present invention, t is preferably an integer from 0 to 2, more preferably from 0 to 1.

In the compounds of the present invention, v is preferably 0.

In certain embodiments of the present invention, the compounds correspond to the formulas with the following designated stereochemistry at the carbon atom where $R^5$ and $R^6$ are attached:

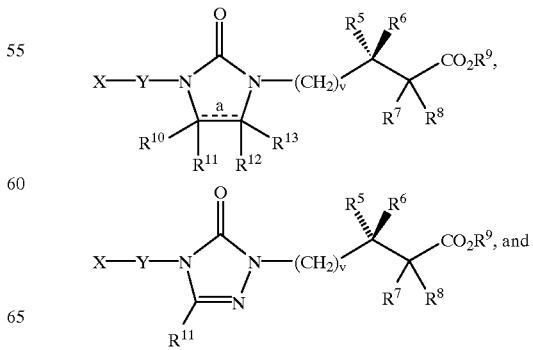

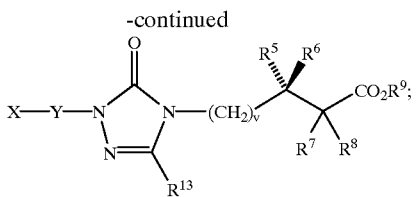

wherein the substituents X, Y, Z, $R^1$, $R^2$, $R^3$, $R^4$, $R^5$, $R^6$, $R^7$, $R^8$, $R^9$, $R^{10}$, $R^{11}$, $R^{12}$, and $R^{13}$ and the subscripts a, m, n, p, r, s, t, and v are as described above.

Illustrative but nonlimiting examples of compounds of the present invention that are useful as integrin receptor antagonists are the following:

3(S)-(2,3-Dihydro-benzofuran-6-yl)-3-{2-oxo-3-[3-(5,6,7,8-tetrahydro- [1,8]naphthyridin-2-yl)-propyl]-imidazolidin-1-yl}-propionic acid, 3(R)-(2,3-Dihydro-benzofuran-6-yl)-3-{2-oxo-3-[3-(5,6,7,8-tetrahydro- [1,8]naphthyridin-2-yl)-propyl]-imidazolidin-1-yl}-propionic acid, 3-(2,3-Dihydro-benzofuran-6-yl)-3-{2-oxo-3-[3-(5,6,7,8-tetrahydro- [1,8]naphthyridin-2-yl)-propyl]-imidazolidin-1-yl}-propionic acid, 3(S)-(3-Fluorophenyl)-3-{2-oxo-3-[3-(5,6,7,8-tetrahydro-[1,8]naphthyridin- 2-yl)-propyl]-imidazolidin-1-yl}-propionic acid, 3(R)-(3-Fluorophenyl)-3-{2-oxo-3-[3-(5,6,7,8-tetrahydro-[1,8]naphthyridin- 2-yl)-propyl]imidazolidin-1-yl}-propionic acid, 3-(3-Fluorophenyl)-3-{2-oxo-3-[3-(5,6,7,8-tetrahydro-[1,8]naphthyridin-2- yl)-propyl]-imidazolidin-1-yl}-propionic acid, 3(S)-(Quinolin-3-yl)-3-{2-oxo-3-[3-(5,6,7,8-tetrahydro-[1,8]naphthyridin-2- yl)-propyl]-imidazolidin-1-yl}-propionic acid, 3(R)-(Quinolin-3-yl)-3-{2-oxo-3-[3-(5,6,7,8-tetrahydro-[1,8]naphthyridin-2- yl)-propyl]-imidazolidin-1-yl}-propionic acid, 3-(Quinolin-3-yl)-3-{2-oxo-3-[3-(5,6,7,8-tetrahydro-[1,8]naphthyridin-2-yl)- propyl]-imidazolidin-1-yl}-propionic acid, 3(S)-(Ethynyl)-3-{2-oxo-3-[3-(5,6,7,8-tetrahydro-[1,8]naphthyridin-2-yl)- propyl]-imidazolidin-1-yl}-propionic acid, 3(R)-(Ethynyl)-3-{2-oxo-3-[3-(5,6,7,8-tetrahydro-[1,8]naphthyridin-2-yl)- propyl]-imidazolidin-1-yl}-propionic acid, 3-(Ethynyl)-3-{2-oxo-3-[3-(5,6,7,8-tetrahydro-[1,8]naphthyridin-2-yl)- propyl]-imidazolidin-1-yl}-propionic acid, 3(S)-(Pyridin-3-yl)-3-{2-oxo-3-[3-(5,6,7,8-tetrahydro-[1,8]naphthyridin-2- yl)-propyl]-imidazolidin-1-yl}-propionic acid, 3(R)-(Pyridin-3-yl)-3-{2-oxo-3-[3-(5,6,7,8-tetrahydro-[1,8]naphthyridin-2- yl)-propyl]-imidazolidin-1-yl}-propionic acid, 3-(Pyridin-3-yl)-3-{2-oxo-3-[3-(5,6,7,8-tetrahydro-[1,8]naphthyridin-2-yl)- propyl]-imidazolidin-1-yl}-propionic acid, 3(S)-(Pyridin-3-yl)-3-{2-oxo-3-[3-(5,6,7,8-tetrahydro-[1,8]naphthyridin-2- yl)-propyl]-4-methyl-imidazolidin-1-yl}-propionic acid, 3(R)-(Pyridin-3-yl)-3-{2-oxo-3-[3-(5,6,7,8-tetrahydro-[1,8]naphthyridin-2- yl)-propyl]-4-methyl-imidazolidin-1-yl}-propionic acid, 3-(Pyridin-3-yl)-3-{2-oxo-3-[3-(5,6,7,8-tetrahydro-[1,8]naphthyridin-2-yl)- propyl]-4-methyl-imidazolidin-1-yl}-propionic acid, 3(S)-(6-Methoxypyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Methoxypyridin-3-yl)-3-{2-oxo-3-[3-(5,6,7,8-tetrahydro- [1,8]naphthyridin-2-yl)-propyl]-imidazolidin-1-yl}-propionic acid, 3-(6-Methoxypyridin-3-yl)-3-{2-oxo-3-[3-(5,6,7,8-tetrahydro- [1,8]naphthyridin-2-yl)-propyl]-imidazolidin-1-yl}-propionic acid, 3(S)-(6-Ethoxypyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Ethoxypyridin-3-yl)-3-{2-oxo-3-[3-(5,6,7,8-tetrahydro- [1,8]naphthyridin-2-yl)-propyl]-imidazolidin-1-yl}-propionic acid, 3-(6-Ethoxypyridin-3-yl)-3-{2-oxo-3-[3-(5,6,7,8-tetrahydro- [1,8]naphthyridin-2-yl)-propyl]-imidazolidin-1-yl}-propionic acid, trifluoroacetate salt, 3(S)-(4-Methoxyquinolin-7-yl)-3-{2-oxo-3-[3-(5,6,7,8-tetrahydro- [1,8]naphthyridin-2-yl)-propyl]-imidazolidin-1-yl}-propionic acid, bis(trifluoroacetate) salt, 3(R)-(4-Methoxyquinolin-7-yl)-3-{2-oxo-3-[3-(5,6,7,8-tetrahydro- [1,8]naphthyridin-2-yl)-propyl]-imidazolidin-1-yl}-propionic acid, 3-(4-Methoxyquinolin-7-yl)-3-{2-oxo-3-[3-(5,6,7,8-tetrahydro- [1,8]naphthyridin-2-yl)-propyl]-imidazolidin-1-yl}-propionic acid, 3(S)-(6-Amino-pyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Amino-pyridin-3-yl)-3-{2-oxo-3-t3-(5,6,7,8-tetrahydro- [1,8]naphthyridin-2-yl)-propyl]-imidazolidin-1-yl}-propionic acid, 3-(6-Amino-pyridin-3-yl)-3-{2-oxo-3-[3-(5,6,7,8-tetrahydro- [1,8]naphthyridin-2-yl)-propyl]-imidazolidin-1-yl}-propionic acid, 3-(S)-(4-Methyl-3-oxo-3,4-dihydro-2H-benzo[1,4]oxazin-7-yl)-3-{2-oxo-3- [3- (5,6,7,8-tetrahydro-[1,8] naphthyridin-2-yl)-propyl]-imidazolidin-1-yl}- propionic acid, 3-(R)-(4-Methyl-3-oxo-3,4-dihydro-2H-benzo[1,4oxazin-7-yl)-3-{2-oxo-3- [3- (5,6,7,8-tetrahydro-[1,8] naphthyridin-2-yl)-propyl]-imidazolidin-1-yl}- propionic acid, 3-(4-Methyl-3-oxo-3,4-dihydro-2H-benzo[1,4]oxazin-7-yl) 3-{2-oxo-3- [3- (5,6,7,8-tetrahydro-[1,8]naphthyridin-2-yl)-propyl]-imidazolidin-1-yl}- propionic acid, 3(S)-(6-Methylamino-pyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Methylamino-pyridin-3-yl)-3-{2-oxo-3-[3-(5,6,7,8-tetrahydro- [1,8]naphthyridin-2-yl)-propyl]-imidazolidin-1-yl}-propionic acid, 3-(6-Methylamino-pyridin-3-yl)-3-{2-oxo-$^3$-[$^3$-(5,6,7,8-tetrahydro- [1,8]naphthyridin-2-yl)-propyl]-imidazolidin-1-yl}-propionic acid, 3(S)-(2-Fluoro-biphenyl-4yl)-3-{2-oxo-3-[3-(5,6,7,8-tetrahydro- [1,8]naphthyridin-2-yl)-propyl]-imidazolidin-1-yl}-propionic acid, 3(R)-(2-Fluoro-biphenyl-4-yl)-3-{2-oxo-3-[3-(5,6,7,8-tetrahydro- [1,8]napthyridin-2-yl)-propyl]-imidazolidin-1-yl}-propionic acid, 3-(2-Fluoro-biphenyl-4-yl)-3-{2-oxo-3-[3-(5,6,7,8-tetrahydro- (1,8]naphthyridin-2-yl)-propyl]-imidazolidin-1-yl}-propionic acid, 3(S)-(2-Oxo-2,3-dihydro-benzoxazol-6-yl)-3-{2-oxo-3-[3- (5,6,7,8-tetrahydro- [1,8]napthyridin-2-yl)-propyl]-imidazolidin-1-yl}-propionic acid, 3(R)-(2-Oxo-2,3-dihydro-benzoxazol-6-yl)-3-{2-oxo-3-[3-(5,6,7,8-tetrahydro- [1,8]napthyridin-2-yl)-propyl]-imidazolidin-1-yl}-propionic acid, 3-(2-Oxo-2,3-dihydro-benzoxazol-6-yl)-3-{2-oxo-3-[3-(5,6,7,8-tetrahydro- [1,8]napthyridin-2-yl)-propyl]-imidazolidin-1-yl}-propionic acid, 3(S)-(4-Ethoxy-3-fluorophenyl)-3-{2-oxo-3-[3-(5,6,7,8-tetrahydro- [1,8]napthyridin-2-yl)-propyl-imidazolidin-1-yl}-propionic acid, 3(R)-(4-Ethoxy-3-fluorophenyl)-3-{2-oxo-3-[3-(5,6,7,8-tetrahydro- [1,8]napthyridin-2-yl)-propyl]-imidazolidin-1-yl}-propionic acid, 3-(4-Ethoxy-3-fluorophenyl)-3-{2-oxo-3-[3-(5,6,7,8-tetrahydro- [1,8]napthyridin-2-yl)-propyl]-imidazolidin-1-yl}-propionic acid, 3(S)-(5-Ethoxy-pyridin-3-yl)-3-{2-oxo-3-[3-(5,6,7,8-tetrahydro- [1,8]naphthyridin-2-yl)-propyl]-imidazolidin-1-yl}-propionic acid, 3(R)-(5-Ethoxy-pyridin-3-yl)-3-{2-oxo-3-[3-(5,6,7,8-tetrahydro- [1,8]naphthyridin-2-yl)-propyl]-imidazolidin-1-yl}-propionic acid, 3-(5-Ethoxy-pyridin-3-yl)-3-{2-oxo-3-[3-(5,6,7,8-tetrahydro- [1,8]naphthyridin-2-yl)-propyl]-imidazolidin-1-yl}-propionic acid, 3(S)-(5-Hydroxy-pyridin-3-yl)-3-{2-oxo-3-[3-(5,6,7,8-tetrahydro- [1,8]naphthyridin-2-yl)-propyl]-imidazolidin-1-yl}-propionic acid, 3()-(5-Hydroxy-pyridin-3-yl)-3-{2-oxo-3-[3-(5,6,7,8-tetrahydro- [1,8]naphthyridin-2-yl)-propyl]-imidazolidin-1-yl}-propionic acid, 3-(5-Hydroxy-pyridin-3-yl)-3-{2-oxo-3-[3-(5,6,7,8-tetrahydro- [1,8]naphthyridin-2-yl)-propyl]-imidazolidin-1-yl}-propionic acid, 2(S)-Benzenesulfonylamino-3-{2-oxo-3-[3-(5,6,7,8-tetrahydro- [1,8]naphthyridin-2-yl)-propyl]-imidazolidin-1-yl}-propionic acid, 3(S)-{2-Oxo-3-[3-(5,6,7,8-tetrahydro-[1,8]naphthyridin-2-yl)-propyl]- imidazolidin-1-yl}-pent-4-enoic acid, 3(R)-{2-Oxo-3-[3-(5,6,7,8-tetrahydro-[1,8]naphthyridin-2-yl)-propyl]- imidazolidin-1-yl}-pent-4-enoic acid, 3-{2-Oxo-3-[3-(5,6,7,8-tetrahydro-[1,8]naphthyridin-2-yl)-propyl]- imidazolidin-1-yl}-pent-4-enoic acid, 3(S)-(5-Ethoxy-pyridin-3-yl)-3-(3-{3-[6-(4-methoxy-benzylamino)-pyridin-2- yl]-propyl}-2-oxo-imidazolidin-1-yl)-propionic acid, 3(R)-(5-Ethoxy-pyridin-3-yl)-3-(3-{3-[6-(4-methoxy-benzylamino)-pyridin-2- yl]-propyl}-2-oxo-imidazolidin-1-yl)-propionic acid, 3-(5-Ethoxy-pyridin-3-yl)-3-(3-{3-[6-(4-methoxy-benzylamino)-pyridin-2-yl]- propyl}-2-oxo-imidazolidin-1-yl)-propionic acid, 3-{3-[3-(6-Amino-pyridin-2-yl)-propyl]-2-oxo-imidazolidin-1-yl}-3(S)-(5- ethoxy-pyridin-3-yl)-propionic acid, 3-{3-[3-(6-Amino-pyridin-2-yl)-propyl]-2-oxo-imidazolidin-1-yl}-3(R)-(5- ethoxy-pyridin-3-yl)-propionic acid, 3-{3-[3-(6-Amino-pyridin-2-yl)-propyl]-2-oxo-imidazolidin-1-yl}-3-(5- ethoxy-pyridin-3-yl)-propionic acid, 3(S)-(2-Oxo-2,3-dihydro-1H-4-oxa-1,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3(R)-(2-Oxo-2,3-dihydro-1H-4-oxa-1,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3-(2-Oxo-2,3-dihydro-1H-4-oxa-1,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3(S)-(2,3-Dihydro-1H-4-oxa-1,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3(R)-(2,3-Dihydro-1H-4-oxa-1,5-diaza-naphthalen-7-yl)3-{2-oxo-3-[3- (5,6,7,8-tetrahydro-[1,8]naphthyridin-2-yl)propyl]-imidazolidin-1- yl}propionic acid, 3-(2,3-Dihydro-1H-4-oxa-1,5-diaza-naphthalen-7-yl)3-{2-oxo-3-[3-(5,6,7,8- tetrahydro-[1,8]naphthyridin-2-yl)propyl]-imidazolidin-1-yl}propionic acid, 3(S)-(3-Oxo-3,4-dihydro-2H- 1-oxa-4,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3(R)-(3-Oxo-3,4-dihydro-2H-1-oxa-4,5-diaza-naphthalen-7-yl)-3-{2-oxo-3-[3- (5,6,7,8-tetrahydro-[1,8]naphthyridin-2-yl)propyl]-imidazolidin1- yl}propionic acid, 3-(3-Oxo-3,4-dihydro-2H-1-oxa-4,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3(S)-(3,4-Dihydro-2H-1-oxa-4,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3(R)-(3,4-Dihydro-2H-1-oxa-4,5-diaza-naphthalen-7-yl)-3-{2-oxo-3-[3- (5,6,7,8-tetrahydro-[1,8]naphthyridin-2-yl)propyl]-imidazolidin-1- yl}propionic acid, 3-(3,4Dihydro-2H-1-oxa-4,5-diaza-naphthalen-7-yl)-3-{2-oxo-3-[3-(5,6,7,8- tetrahydro-[1,8]naphthyridin-2-yl)propyl]-imidazolidin-1-yl}propionic acid, 3-(Furo[2,3-b]pyridin-6-yl)-3-{2-oxo-3-[3-(5,6,7,8-tetrahydro- [1,8]naphthyridin-2-yl)propyl]imidazolidin-1-yl}propionic acid, 3(S)-(Furo[2,3-b]pyridin-6-yl)-3-{2-oxo-3-[3-(5,6,7,8-tetrahydro- [1,8]naphthyridin-2-yl)propyl]imidazolidin-1-yl}propionic acid, 3(R)-(Furo[2,3-b]pyridin-6-yl)-3-{2-oxo-3-[3-(5,6,7,8-tetrahydro- [1,8]naphthyridin-2-yl)propyl]imidazolidin-1-yl}propionic acid, 3(S)-(2,3-Dihydrofuro[2,3-b]pyridin-6-yl)-3-{2-oxo-3-[3-(5,6,7,8-tetrahydro- [1,8]naphthyridin-2-yl)propyl]imidazolidin- 1-yl}propionic acid, 3(R)-(2,3-Dihydrofuro[2,3-b]pyridin-6-yl)-3-{2-oxo-3-[3-(5,6,7,8-tetrahydro- [1,8]naphthyridin-2-yl)propyl]imidazolidin-1-yl}propionic acid, 3-(2,3-Dihydrofuro[2,3-b]pyridin-6-yl)-3-{2-oxo-3-[3-(5,6,7,8-tetrahydro- [1,8]naphthyridin-2-yl)propyl]imidazolidin-1-yl}propionic acid, 3(S)-(Furo[3,2-b]pyridin-6-yl)-3-{2-oxo-3-[3-(5,6,7,8-tetrahydro- [1,8]naphthyridin-2-yl)propyl]imidazolidin-1-yl}propionic acid, 3(R)-(Furo[3,2-b]pyridin-6-yl)-3-{2-oxo-3-[3-(5,6,7,8-tetrahydro- [1,8]naphthyridin-2-yl)propyl]imidazolidin-1-yl}propionic acid, 3-(Furo[3,2-b]pyridin-6-yl)-3-{2-oxo-3-[3-(5,6,7,8-tetrahydro- [1,8]naphthyridin-2-yl)propyl]imidazolidin-1-yl}propionic acid, 3(S)-(2,3-Dihydrofuro[3,2-b]pyridin-6-yl-3-{2-oxo-3-[3-(5,6,7,8-tetrahydro- [1,8]naphthyridin-2-yl)propyl]imidazolidin-1-yl}propionic acid, 3(R)-(2,3-Dihydrofuro[3,2-b]pyridin-6-yl)-3-{2-oxo-3-[3-(5,6,7,8-tetrahydro- [1,8]naphthyridin-2-yl)propyl]imidazolidin-1-yl}propionic acid, 3-(2,3-Dihydrofuro[3,2-b]pyridin-6-yl)-3-{2-oxo-3-[3-(5,6,7,8-tetrahydro- [1,8]naphthyridin-2-yl)propyl]imidazolidin-1-yl}propionic acid, 3(S)-(Benzimidazol-2-yl)-3-(2-oxo-3-[3-(5,6,7,8-tetrahydro- [1,8]naphthyridin-2-yl)propyl]imidazolidin-1-yl)propionic acid, 3(R)-(Benzimidazol-2-yl)-3-(2-oxo-3-[3-(5,6,7,8-tetrahydro- [1,8]naphthyridin-2-yl)propyl]imidazolidin-1-yl)propionic acid, 3-(Benzimidazol-2-yl)-3-(2-oxo-3-[3-(5,6,7,8-tetrahydro-[1,8]naphthyridin- 2-yl)propyl]imidazolidin- 1-yl) propionic acid, 3(S)-(1H-Imidazo[4,5-c]pyridin-2-yl)-3-(2-oxo-3-[3-(5,6,7,8-tetrahydro- [1,8]naphthyridin-2-yl)propyl]-imidazolidin- 1yl)propionic acid, 3(R)-(1H-Imidazo[4,5-c]pyridin-2-yl)-3-(2-oxo-3-[3-(5,6,7,8-tetrahydro- [1,8]naphthyridin-2-yl)propyl]-imidazolidin-1-yl)propionic acid, 3-(1H-Imidazo[4,5-c]pyridin-2-yl)-3-(2-oxo-3-[3-(5,6,7,8-tetrahydro- [1,8]naphthyridin-2-yl)propyl]-imidazolidin-1-yl)propionic acid, 3(S)-(Benzoxazol-2-yl)-3-( 2-oxo-3-[3-(5,6,7,8-tetrahydro-[1,8]naphthyridin- 2-yl)propyl]imidazolidin-1-yl) propionic acid, 3(R)-(Benzoxazol-2-yl)-3-(2-oxo-3-[3-(5,6,7,8-tetrahydro-[1,8]naphthyridin- 2-yl)propyl]imidazolidin-1-yl) propionic acid, 3-(Benzoxazol-2-yl)-3-(2-oxo-3-[3-(5,6,7,8-tetrahydro-[1,8]naphthyridin-2 yl)propyl]imidazolidin-1-yl)propionic acid, 3(S)-(1-Methyl-1H-pyrazol-4yl)-3-(2-oxo-3-[3-(5,6,7,8-tetrahydro [1,8]naphthyridin-2-yl)propyl]-imidazolidin-1-yl)propionic acid, 3(R)-(1-Methyl-1H-pyrazol-4yl)-3-(2-oxo-3-[3-(5,6,7,8-tetrahydro- [1,8]naphthyridin-2-yl)propyl]-imidazolidin-1-yl)propionic acid, 3-(1-Methyl-1H-pyrazol-4yl)-3-(2-oxo-3-[3-(5,6,7,8-tetrahydro- [1,8]naphthyridin-2-yl)propyl]-imidazolidin-1-yl)propionic acid, and the pharmaceutically acceptable salts thereof.

Further illustrative of the present invention are the compounds selected from the group consisting of 3(S)-(2,3-Dihydro-benzofuran-6-yl)-3-{2-oxo-3-[3-(5,6,7,8-tetrahydro- [1,8]naphthyridin-2-yl)-propyl]-imidazolidin-1-yl}-propionic acid, 3(R)-(2,3-Dihydro-benzofuran-6-yl)-3-{2-oxo-3-[3-(5,6,7,8-tetrahydro- [1,8]naphthyridin-2-yl)-propyl]-imidazolidin-1-yl}-propionic acid, 3(S)-(3-Fluorophenyl)-3-{2-oxo-3-[3-(5,6,7,8-tetrahydro-[1,8]naphthyridin- 2-yl)-propyl]-imidazolidin-1-yl}-propionic acid, 3(R)-(3-Fluorophenyl)-3-{2-oxo-3-[3-(5,6,7,8-tetrahydro-[1,8]naphthyridin- 2-yl)-propyl]-imidazolidin-1-yl}-propionic acid, 3(S)-(Quinolin-3-yl)-3-{2-oxo-3-[3-(5,6,7,8-tetrahydro-[1,8]naphthyridin-2- yl)-propyl]-imidazolidin-1-yl}-propionic acid, 3(R)-(Quinolin-3-yl)-3-{2-oxo-3-[3-(5,6,7,8-tetrahydro-[1,8]naphthyridin-2- yl)-propyl]-imidazolidin-1-yl}-propionic acid, 3(S)-(Ethynyl)-3-{2-oxo-3-[3-(5,6,7,8-tetrahydro-[1,8]naphthyridin-2-yl)- propyl]-imidazolidin-1-yl}-propionic acid, 3(R)-(Ethynyl)-3-{2-oxo-3-[3-(5,6,7,8-tetrahydro-[1,8]naphthyridin-2-yl)- propyl]-imidazolidin-1-yl}-propionic acid, 3(S)-(Pyridin-3-yl)-3-{2-oxo-3-[3-(5,6,7,8-tetrahydro-[1,8]naphthyridin-2- yl)-propyl]-imidazolidin-1-yl}-propionic acid, 3(R)-(Pyridin-3-yl)-3-{2-oxo-3-[3-(5,6,7,8-tetrahydro-[1,8]naphthyridin-2- yl)-propyl]-imidazolidin-1-yl}-propionic acid, 3(S)-(Pyridin-3-yl)-3-{2-oxo-3-[3-(5,6,7,8-tetrahydro-[1,8]naphthyridin-2- yl)-propyl]-4-methyl-imidazolidin-1-yl}-propionic acid, 3(R)-(Pyridin-3-yl)-3-{2-oxo-3-[3-(5,6,7,8-tetrahydro-[1,8]naphthyridin-2- yl)-propyl]-4-methyl-imidazolidin-1-yl}-propionic acid, 3(S)-(6-Methoxypyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Methoxypyridin-3-yl)-3- {2-oxo-3-[3-(5,6,7,8-tetrahydro- [1,8]naphthyridin-2-yl)-propyl]-imidazolidin-1-yl}-propionic acid, 3(S)-(6-Ethoxypyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Ethoxypyridin-3-yl)-3-{2-oxo-3-[3-(5,6,7,8-tetrahydro- [1,8]naphthyridin-2-yl)-propyl]-imidazolidin-1-yl}-propionic acid, 3(S)-(4-Methoxyquinolin-7-yl)-3-{2-oxo-3-[3-(5,6,7,8-tetrahydro- [1,8]naphthyridin-2-yl)-propyl]-imidazolidin-1-yl}-propionic acid, bis(trifluoroacetate) salt, 3(R)-(4-Methoxyquinolin-7-yl)-3-{2-oxo-3-[3-(5,6,7,8-tetrahydro- [1,8]naphthyridin-2-yl)-propyl]-imidazolidin-1-yl}-propionic acid, 3(S)-(6-Amino-pyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Amino-pyridin-3-yl)-3-{2-oxo-3-[3-(5,6,7,8-tetrahydro- [1,8]naphthyridin-2-yl)-propyl]-imidazolidin-1-yl}-propionic acid, 3-(S)-(4-Methyl-3-oxo-3,4-dihydro-2H-benzo[1,4]oxazin-7-yl)-3-{2-oxo -3-[3- (5,6,7,8-tetrahydro-[1,8]naphthyridin-2-yl)-propyl]-imidazolidin-1-yl}- propionic acid, 3-(R)-(4-Methyl-3-oxo-3,4-dihydro-2H-benzo[1,4]oxazin-7-yl)-3-{2-oxo-3-[3- (5,6,7,8-tetrahydro-[1,8]naphthyridin-2-yl)-propyl]-imidazolidin-1-yl}- propionic acid, 3(S)-(6-Methylamino-pyridin-3-yl)-3-{2-oxo-3-[3-(5,6,7,8-tetrahydro- [1,8]naphthyridin-2-yl)-propyl]-imidazolidin-1-yl}-propionic acid, 3(R)-(6-Methylamino-pyridin-3-yl)-3-{2-oxo-3-[3-(5,6,7,8-tetrahydro- [1,8]naphthyridin-2-yl)-propyl]-imidazolidin-1-yl}-propionic acid, 3(S)-(2-Fluoro-biphenyl-4yl)-3-{2-oxo-3-[3-(5,6,7,8-tetrahydro- [1,8]naphthyridin-2-yl)-propyl]-imidazolidin-1-yl}-propionic acid, 3(R)-(2-Fluoro-biphenyl-4-yl)-3-{2-oxo-3-[3-(5,6,7,8-tetrahydro- [1,8]naphthyridin-2-yl)-propyl]-imidazolidin-1-yl}-propionic acid, 3(S)-(2-Oxo-2,3-dihydro-benzoxazol-6-yl)-3-{2-oxo-3-[3-(5,6,7,8-tetrahydro- [1,8]napthyridin-2-yl)-propyl]-imidazolidin-1-yl}-propionic acid, 3(R)-(2-Oxo-2,3-dihydro-benzoxazol-6-yl)-3-{2-oxo-3-[3-(5,6,7,8-tetrahydro- [1,8]napthyridin-2-yl)-propyl]-imidazolidin-1-yl}-propionic acid, 3(S)-(4-Ethoxy3-fluorophenyl)-3-{2-oxo-3-[3-(5,6,7,8-tetrahydro- [1,8]napthyridin-2-yl)-propyl]-imidazolidin-1-yl}-propionic acid, 3(R)-(4-Ethoxy-3-fluorophenyl)-3-{2-oxo-3-[3-(5,6,7,8-tetrahydro- [1,8]napthyridin-2-yl)-propyl]-imidazolidin-1-yl}-propionic acid, 3(S)-(5-Ethoxy-pyridin-3-yl)-3-{2-oxo-3-[3-(5,6,7,8-tetrahydro- [1,8]naphthyridin-2-yl)-propyl]-imidazolidin-1-yl}-propionic acid, 3(R)-(5 -Ethoxy-pyridin-3-yl)-3-{2-oxo-3-[3-(5,6,7,8-tetrahydro- [1,8]naphthyridin-2-yl)-propyl]-imidazolidin-1-yl}-propionic acid, 3(S)-(5-Hydroxy-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(5-Hydroxy-pyridin-3-yl)-3-{2-oxo-3-[3-(5,6,7,8-tetrahydro-[1,8]naphthyridin-2-yl)-propyl]-imidazolidin-1-yl}-propionic acid, 3(S)-{2-Oxo-3-[3-(5,6,7,8-tetrahydro-[1,8]naphthyridin-2-yl)-propyl]-imidazolidin-1-yl]-pent-4-enoic acid, 3(R)-{2-Oxo-3-[3-(5,6,7,8-tetrahydro-[1,8 naphthyridin-2-yl)-propyl]-imidazolidin-1-yl}-pent-4-enoic acid, 3(S)-(5-Ethoxy-pyridin-3-yl)-3-(3-{3-[6-(4-methoxy-benzylamino)-pyridin-2-yl]-propyl}-2-oxo-imidazolidin-1-yl)-propionic acid, 3(R)-(5-Ethoxy-pyridin-3-yl)-3-(3-{3-[6-(4-methoxy-benzylamino)-pyridin-2-yl]-propyl}-2-oxo-imidazolidin-1-yl)-propionic acid, 3-{3-[3-(6-Amino-pyridin-2-yl)-propyl]-2-oxo-imidazolidin-1-yl}-3(S)-(5-ethoxy-pyridin-3-yl)-propionic acid, 3-{3-[3-(6-Amino-pyridin-2-yl)-propyl]-2-oxo-imidazolidin-1-yl}-3(R)-(5-ethoxy-pyridin-3-yl)-propionic acid, 3(S)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(S)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-yl}propionic acid, 3(S)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(S)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(S)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Furo3,2-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Benzimidazol-2-yl)-3-(2-oxo-3-[3-(5,6,7,8-tetrahydro-[1,8]naphthyridin-2-yl)propyl]imidazolidin-1-yl)propionic acid, 3(R)-(Benzimidazol-2-yl)-3-(2-oxo-3-[3-(5,6,7,8-tetrahydro-[1,8]naphthyridin-2-yl)propyl]imidazolidin-1-yl)propionic acid, 3(S)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid, 3(R)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid, 3(S)-(Benzoxazol-2-yl)-3-(2-oxo-3-[3-(5,6,7,8-tetrahydro-[1,8]naphthyridin-2-yl)propyl]imidazolidin-1-yl) propionic acid, 3(R)-(Benzoxazol-2-yl)-3-(2-oxo-3-[3-(5,6,7,8-tetrahydro-[1,8]naphthyridin-2-yl)propyl]imidazolidin-1-yl) propionic acid, 3(S)-(1-Methyl-1H-pyrazol-4yl)-3-(2-oxo-3-[3-(5,6,7,8-tetrahydro-[1,8]naphthyridin-2-yl)propyl]-imidazolidin-1-yl)propionic acid, 3(R)-(1-Methyl-1H-pyrazol-4 yl)-3-(2-oxo-3-[3-(5,6,7,8-tetrahydro-[1,8]naphthyridin-2-yl)propyl]-imidazolidin-1-yl)propionic acid, and the pharmaceutically acceptable salts thereof.

Yet further illustrative are the compounds

3(S)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3(S)-(Quinolin-3-yl)-3-{2-oxo-3-[3-(5,6,7,8-tetrahydro-[1,8]naphthyridin-2-yl)-propyl]-imidazolidin-1-yl}-propionic acid, 3(S)-(Pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, bis(trifluoroacetate) salt, 3(S)-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid, 3(S)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Benzimidazol-2-yl)-3-(2-oxo-3-[3-(5,6,7,8-tetrahydro-[1,8]naphthyridin-2-yl)propyl]imidazolidin-1-yl)propionic acid, 3(S)-(Benzoxazol-2-yl)-3-(2-oxo-3-[3-(5,6,7,8-tetrahydro-[1,8]naphthyridin-2-yl)propyl]imidazolidin-1-yl) propionic acid, and the pharmaceutically acceptable salts thereof.

For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following: acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention can have chiral centers and occur as racemates, racemic mixtures, diastereomeric mixtures, and as individual diastereomers, or enantiomers with all isomeric forms being included in the present invention. Therefore, where a compound is chiral, the separate enantiomers or diastereomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "integrin receptor antagonist," as used herein, refers to a compound which binds to and antagonizes either the αvβ3 receptor, the αvβ5 receptor, or the αvβ6 receptor, or a compound which binds to and antagonizes combinations of these receptors (for example, a dual αvβ3/αvβ5 receptor antagonist).

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "cycloheteroalkyl," as used herein, shall mean a 3- to 8-membered fully saturated heterocyclic ring containing one or two heteroatoms chosen from N, O or S. Examples of cycloheteroalkyl groups include, but are not limited to piperidinyl, pyrrolidinyl, azetidinyl, morpholinyl, piperazinyl.

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system comprising at least one aromatic ring, wherein the monocylic or polycyclic system contains 0, 1, 2, 3, or 4 heteroatoms chosen from N, O, or S, and wherein the monocylic or polycylic system is either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, benzthiazolyl, benzoxazolyl, indolyl, thienyl, furyl, pyrryl, pyrazolyl, dihydrobenzofuryl, benzo(1,3) dioxolane, oxazolyl, isoxazolyl and thiazolyl, which are either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above- named substituents.

Whenever the term "alkyl" or "aryl" or either of their prefix roots appears in a name of a substituent (e.g., aryl $C_{0-8}$ alkyl), it shall be interpreted as including those limitations given above for "alkyl" and "aryl." Designated numbers of carbon atoms (e.g., $C_{0-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

In the compounds of the present invention, two $R^1$ substituents, when on the same carbon atom, can be taken together with the carbon to which they are attached to form a carbonyl group.

In the compounds of the present invention, two $R^3$ substituents, when on the same carbon atom, can be taken together with the carbon atom to which they are attached to form a carbonyl group. In such instances, the limitation, that in the resultant compound the carbon atom or atoms to which $R^3$ is attached is itself attached to no more than one heteroatom, does not apply. Also, in the compounds of the present invention, two $R^3$ substituents, when on the same carbon atom, can be taken together with the carbon atom to which they are attached to form a cyclopropyl group.

In the compounds of the present invention, $R^5$ and $R^6$ can be taken together with the carbon atom to which they are attached to form a carbonyl group. In such instances, the limitation, that in the resultant compound the carbon atom at which $R^5$ and $R^6$ is attached is itself attached to no more than one heteroatom, does not apply.

When substituents $R^7$ and $R^8$ include the definition $C_0$ (e.g., $C_{0-8}$ alkyl), the group modified by $C_0$ is not present in the substituent when C is zero. Similarly, when any of the variables m, n, t, or v, is zero, then the group modified by the variable is not present; for example, when t is zero, the group "—$(CH_2)_t$C≡CH" is "—C≡CH". In addition, the substituent "$(C_{1-6}$ alkyl$)_p$amino" where p is zero, one or two, refers to an amino, $C_{1-6}$ alkylamino and $C_{1-6}$ dialkylamino group, respectively. When a $C_{1-6}$ dialkylamino substituent is intended, the $C_{1-6}$ alkyl groups can be the same (e.g., dimethylamino) or different (e.g., $N(CH_3)(CH_2CH_3)$). Similarly, the substituent "(aryl)$_p$amino" or ["(aryl $C_{1-6}$ alkyl)$_p$amino"], where p is zero, one or two, refers to an amino, arylamino and diarylamino group, [or an amino, aryl $C_{1-6}$ alkylamino or di-(aryl $C_{1-6}$ alkyl)amino] respectively, where the aryl [or aryl $C_{1-6}$ alkyl] groups in a diarylamino [or di-(aryl $C_{1-6}$ alkyl)amino] substituent can be the same or different.

In the compounds of the present invention, $R^{10}$ and $R^{12}$ can be taken together with the carbon atoms to which they are attached to form a 5- to 7-membered monocyclic aromatic or nonaromatic ring system having 0, 1, 2, 3, or 4 heteroatoms selected from the group consisting of N, O, and S wherein said 5- to 7-membered monocylic aromatic or nonaromatic ring system is either unsubstituted or substituted with one or more $R^1$ substituents.

The term "halogen" shall include iodine, bromine, chlorine, and fluorine.

The term "oxy" means an oxygen (O) atom. The term "thio" means a sulfur (S) atom. The term "oxo" means "=O." The term "carbonyl" means "C=O."

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Under standard nonmenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

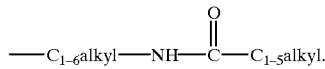

In choosing compounds of the present invention, one of ordinary skill in the art will recognize that the various substituents, i.e. X, Y, Z, $R^1$, $R^2$, $R^3$, $R^4$, $R^5$, $R^6$, $R^7$, $R^8$, $R^9$, $R^{10}$, $R^{11}$, $R^{12}$, and R13 and the subscripts m, n, p, r, s, t, and v are to be chosen in conformity with well-known principles of chemical structure connectivity.

Representative compounds of the present invention typically display submicromolar affinity for the integrin receptors, particularly the αvβ3, αvβ5, and/or αvβ6 receptors. Compounds of this invention are therefore useful for treating mammals suffering from a bone condition caused or mediated by increased bone resorption, who are in need of such therapy. Pharmacologically effective amounts of the compounds, including pharamaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis.

Further exemplifying the invention is the method wherein the integrin receptor antagonizing effect is an αvβ3 antagonizing effect. An illustration of the invention is the method wherein the αvβ3 antagonizing effect is selected from inhibition of bone resorption, restenosis, angiogenesis, diabetic retinopathy, macular degeneration, inflammation, viral disease, tumor growth, or metastasis. Preferably, the αvβ3 antagonizing effect is the inhibition of bone resorption.

An example of the invention is the method wherein the integrin receptor antagonizing effect is an αvβ5 antagonizing effect. More specifically, the αvβ5 antagonizing effect is selected from inhibition of restenosis, angiogenesis, diabetic retinopathy, macular degeneration, inflammation, tumor growth, or metastasis.

Illustrating the invention is the method wherein the integrin receptor antagonizing effect is a dual αvβ3/αvβ5 antagonizing effect. More particularly, the dual αvβ3/αv,β5 antagonizing effect is selected from inhibition of bone resorption, restenosis, angiogenesis, diabetic retinopathy, macular degeneration, inflammation, viral disease, tumor growth, or metastasis.

Illustrating the invention is the method wherein the integrin receptor antagonizing effect is an αvβ6 antagonizing effect. More particularly, the αvβ6 antagonizing effect is selected from inhibition of angiogenesis, inflammatory response, or wound healing.

Illustrating the invention is the method wherein the αvβ3 antagonizing effect is selected from inhibition of bone resorption, inhibition of restenosis, inhibition of angiogenesis, inhibition of diabetic retinopathy, inhibition of macular degeneration, inhibition of atherosclerosis, inflammation, viral disease, or inhibition of tumor growth or metastasis. Preferably, the αvβ3 antagonizing effect is the inhibition of bone resorption.

More particularly illustrating the invention is a pharmaceutical composition comprising any of the compounds described above and a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Further illustrating the invention is a method of treating and/or preventing a condition mediated by antagonism of an integrin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, viral disease, cancer, tumor growth, and metastasis. More preferably, the condition is selected from osteoporosis and cancer. Most preferably, the condition is osteoporosis.

More specifically exemplifying the invention is a method of eliciting an integrin antagonizing effect in a mammal in need thereof, comprising administering to the mammal a therapeutically effective amount of any of the compounds or any of the pharmaceutical compositions described above. Preferably, the integrin antagonizing effect is an αvβ3 antagonizing effect; more specifically, the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation, inhibition of viral disease, or inhibition of tumor growth or metastasis. Most preferably, the αvβ3 antagonizing effect is inhibition of bone resorption. Alternatively, the integrin antagonizing effect is an αvβ5 antagonizing effect, an αvβ6 antagonizing effect, or a mixed αvβ3, αvβ5, and αvβ6 antagonizing effect. Examples of αvβ5 antagonizing effects are inhibition of restenosis, atherosclerosis, angiogenesis, diabetic retinopathy, macular degeneration, inflammation, viral disease, or tumor growth. Examples of dual αvβ6 antagonizing effects are inhibition of angiogenesis, inflammatory response and wound healing.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions described above.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of bone resorption, tumor growth, cancer, restenosis, atherosclerosis, diabetic retinopathy, macular degeneration, inflammation, viral disease, and/or angiogenesis.

Also exemplifying the invention are compositions farther comprising an active ingredient selected from the group consisting of
a.) an organic bisphosphonate or a pharmaceutically acceptable salt or ester thereof,
b.) an estrogen receptor modulator,
c.) a cytotoxic/antiproliferative agent,
d.) a matrix metalloproteinase inhibitor,
e.) an inhibitor of epidermal-derived, fibroblast-derived, or platelet-derived growth factors,
f.) an inhibitor of VEGF,
g.) an inhibitor of Flk-1/KDR, Flt-1, Tck/Tie-2, or Tie-1,
h.) a cathepsin K inhibitor; and
i.) a prenylation inhibitor, such as a farnesyl transferase inhibitor or a geranylgeranyl transferase inhibitor or a dual farnesyl/geranylgeranyl transferase inhibitor; and mixtures thereof.

(See, B. Millauer et al., "Dominant-Negative Inhibition of Flk-1 Suppresses the Growth of Many Tumor Types in Vivo", *Cancer Research* 56, 161514 1620 (1996), which is incorporated by reference herein in its entirety).

Preferably, the active ingredient is selected from the group consisting of:
a.) an organic bisphosphonate or a pharmaceutically acceptable salt or ester thereof,
b.) an estrogen receptor modulator, and
c.) a cathepsin K inhibitor; and mixtures thereof Nonlimiting examples of such bisphosphonates include alendronate, etidronate, pamidronate, risedronate, ibandronate, and pharmaceutically acceptable salts and esters thereof. A particularly preferred bisphosphonate is alendronate, especially alendronate monosodiuim trihydrate.

Nonlimiting examples of estrogen receptor modulators include estrogen, progesterin, estradiol, droloxifene, raloxifene, and tamoxifene.

Nonlimiting examples of cytotoxic/antiproliferative agents are taxol, vincristine, vinblastine, and doxorubicin.

Cathepsin K, formerly known as cathepsin O2, is a cysteine protease and is described in PCT International Application Publication No. WO 96/13523, published May 9, 1996; U.S. Pat. No. 5,501,969, issued Mar. 3, 1996; and U.S. Pat. No. 5,736,357, issued Apr. 7, 1998, all of which are incorporated by reference herein in their entirety. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis.

The present invention is also directed to combinations of the compounds of the present invention with one or more agents useful in the prevention or treatment of osteoporosis. For example, the compounds of the instant invention may be effectively administered in combination with effective amounts of other agents such as an organic bisphosphonate, an estrogen receptor modulator, or a cathepsin K inhibitor.

Additional illustrations of the invention are methods of treating tumor growth in a mammal in need thereof, comprising administering to the mammal a therapeutically effective amount of a compound described above and one or more agents known to be cytotoxic/antiproliferative. Also, the compounds of the present invention can be admninistered in combination with radiation therapy for treating tumor growth and metastasis.

In addition, the integrin αvβ3 antagonist compounds of the present invention may be effectively administered in combination with a growth hormone secretagogue in the therapeutic or prophylactic treatment of disorders in calcium or phosphate metabolism and associated diseases. These diseases include conditions which can benefit from a reduction in bone resorption. A reduction in bone resorption should improve the balance between resorption and formation, reduce bone loss or result in bone augmentation. A reduction in bone resorption can alleviate the pain associated with osteolytic lesions and reduce the incidence and/or growth of those lesions. These diseases include: osteoporosis (including estrogen deficiency, immobilization, glucocorticoid induced and senile), osteodystrophy, Paget's disease, myositis ossificans, Bechterew's disease, malignant hypercalcemia, metastatic bone disease, periodontal disease, cholelithiasis, nephrolithiasis, urolithiasis, urinary calculus, hardening of the arteries (sclerosis), arthritis, bursitis, neuritis and tetany. Increased bone resorption can be accompanied by pathologically high calcium and phosphate concentrations in the plasma, which would be alleviated by this treatment. Similarly, the present invention would be useful in increasing bone mass in patients with growth hormone deficiency. Thus, preferred combinations are simultaneous or alternating treatments of an αvβ3 receptor antagonist of the present invention and a growth hormone secretagogue, optionally including a third component comprising an organic bisphosphonate, preferably alendronate monosodium trihydrate.

In accordance with the method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating integrin-mediated conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixirs, tinctures, suspensions, syrups and emulsions. Likewise, they may also be administered in intravenous (bolus or in-fusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 antagonist.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:

| | |
|---|---|
| AcOH: | Acetic acid. |
| BH$_3$. DMS: | Borane.dimethylsulfide. |
| BOC(Boc): | t-Butyloxycarbonyl. |
| BOP: | Benzotriazol-1-yloxytris(dimethylamino)-phosphonium hexafluorophosphate. |
| CBZ(Cbz): | Carbobenzyloxy or benzyloxycarbonyl. |
| CDI: | Carbonyldiimidazole. |
| CH$_2$Cl$_2$: | Methylene chloride. |
| CH$_3$CN: | Acetonitrile |
| CHCl$_3$: | Chloroform. |
| DBA: | Bis(dibenzylidene)acetone. |
| DEAD: | Diethyl azodicarboxylate. |
| DIAD: | Diisopropyl azodicarboxylate. |
| DIBAH or DIBAL-H: | Diisobutylaluminum hydride. |
| DIPEA: | Diisopropylethylamine. |
| DMAP: | 4-Dimethylaminopyridine. |
| DME: | 1,2-Dimethoxyethane. |
| DMF: | Dimethylformamide. |
| DMSO: | Dimethylsulfoxide. |
| DPPF: | 1,1'-bis(diphenylphosphino)ferrocene. |
| DPFN: | 3,5-Dimethyl-1-pyrazolylformamidine nitrate. |
| EDC: | 1-(3-Dimethylaminopropyl)-3-ethylcarbodiimide.HCl |
| EtOAc: | Ethyl acetate. |
| EtOH: | Ethanol. |
| HOAc: | Acetic acid. |
| HOAT: | 1-Hydroxy-7-azabenzotriazole |
| HOBT: | 1-Hydroxybenzotriazole. |
| IBCF: | Isobutylchloroformate |
| LDA: | Lithium diisopropylamide. |
| MeOH: | Methanol. |
| MMNG | 1,1-methyl-3-nitro-1-nitrosoguanidine |
| NEt$_3$: | Triethylamine. |
| NMM: | N-methylmorpholine. |
| PCA.HCl: | Pyrazole carboxamidine hydrochloride. |
| Pd/C: | Palladium on activated carbon catalyst. |
| Ph: | Phenyl. |
| pTSA | p-Toluenesulfonic acid. |
| TEA: | Triethylamine. |
| TFA: | Trifluoroacetic acid. |
| THF: | Tetrahydrofuran. |
| TLC: | Thin Layer Chromatography. |
| TMEDA: | N,N,N',N'-Tetramethylethylenediamine. |
| TMS: | Trimethylsilyl. |

The novel compounds of the present invention can be prepared according to the procedure of the following schemes and examples, using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Application Publication Nos. WO95/32710, published 7 Dec., 1995, and WO95/17397, published 29 Jun., 1995, both of which

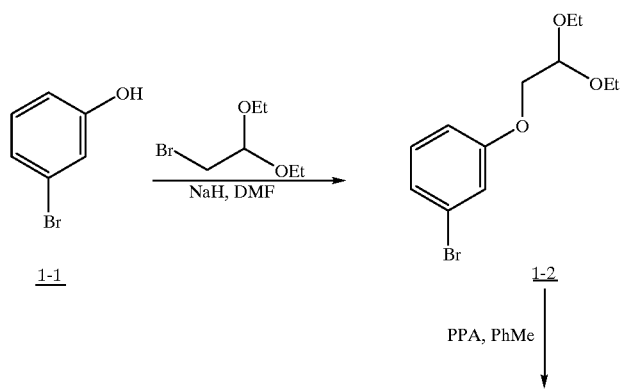

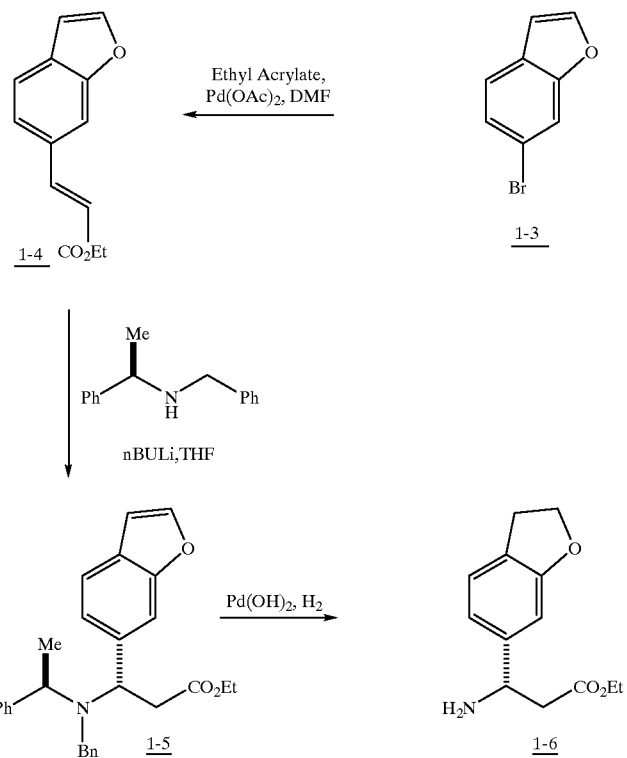

are incorporated by reference herein in their entirety, in conjunction with the disclosure contained herein, one of ordinary skill in the art can readily prepare additional compounds of the present invention claimed herein. Additionally, for a general review describing the synthesis of β-alanines which can be utilized as the C-terminus of the compounds of the present invention, see Cole, D. C., *Recent Stereoselective Synthetic Approaches to β-Amino Acids, Tetrahedron*, 1994, 50, 951714 9582; Juaristi, E, et al., *Enantioselective Synthesis of β-Amino Acids, Aldrichimica Acta*, 1994,27, 3. In particular, synthesis of the 3-methyl-β-alanine is taught in Duggan, M. F. et al., *J. Med. Chem.*, 1995, 38, 3332–3341; the 3-ethynyl-β-alanine is taught in Zablocli, J. A., et al., *J. Med. Chem.*, 1995, 38, 2378–2394; the 3-(pyridin-3-yl)-β-alanine is taught in Rico, J. G. et al., *J. Org. Chem.*, 1993, 58, 7948–7951; and the 2-amino- and 2-tosylamino-β- alanines are taught in Xue, C-B, et al., *Biorg. Med. Chem. Letts.*, 1996, 6, 339–344. The references described in this paragraph are all also incorporated by reference herein in their entirety.

1-Bromo-3-(2,2-diethoxy-ethoxy)-benzene (1-2)

To a suspension of NaH (2.77 g, 115.6 mmol) in DMF (100 mL) at 0° C. was added a solution of 3-bromophenol 1-1 in DMF (40 mL) over 40 min. After the addition was complete, the solution was stirred for an additional 30 min. The solution was then treated with neat bromoacetaldehyde diethyl acetal (17.36 g, 115.6 mmol). The solution was heated at 100° C. for 8 h, cooled to room temperature, and extracted with $Et_2O$ (3×200 mL). The combined organic extracts were washed with 10% aq. NaOH (100 mL) and brine (100 mL), dried over $MgSO_4$, filtered and concentrated to give 1-2 as a yellow oil. TLC Rf=0.4 (10% ethyl acetate/hexanes). $^1$H NMR (300 MHz, $CDCl_3$) δ 7.19–7.05 (m, 3H), 6.85 (d, 1H), 4.81 (t, 1H, J=6.8 Hz), 3.99 (d, 2H, J=6.8 Hz), 3.71 (m, 4H), 1.22 (t, 6H, J=7.1 Hz)

6-Bromo-benzofuran (1-3)

To a solution of the acetal 1-2 in toluene (200 mL) was added polyphosphoric acid (20 g). The biphasic mixture was heated to 100° C. and stirred at this temperature for 4 h. The mixture was cooled to room temperature, poured onto ice, and extracted with $Et_2O$ (2×200 mL). The combined organic extracts were washed with saturated aq. $NaHCO_3$ and brine. The solution was dried over $MgSO_4$, filtered, and concentrated. The residue was purified by flash chromatography (100% hexanes) to give the product 1-3 as a yellow oil. TLC Rf=0.3 (100% hexanes). $^1$H NMR (300 MHz, $CDCl_3$) δ 7.68 (s, 1H), 7.60 (d, 1H, J=2.1 Hz), 7.46 (d, 1H, J=8.4 Hz), 7.36 (dd, 1H, J=8.1, 1.5 Hz), 6.75 (dd, 1H, J=7.1, 0.9 Hz).

3-Benzofuran-6-yl-acrylic acid ethyl ester (1-4)

A mixture of the 6-bromo-benzofuran 1-3 (1.74 g, 8.79 mmol), ethyl acrylate (1.09 g, 10.98 mmol), $Pd(OAc)_2$ (0.099 g, 0.44 mmol), tri-o-tolylphosphine (0.268 g, 0.880 mmol), and sodium acetate (3.60 g, 43.9 mmol) in DMF (10 mL) was heated to 100° C. in a sealed tube for 4 h. The mixture was cooled to room temperature, diluted with water, and extracted with $Et_2O$ (2×40 mL). The combined organic extracts were washed with brine (30 mL), dried over $MgSO_4$, filtered, and concentrated. The residue was purified by flash chromatography (10% ethyl acetate/hexanes) to give the ester 1-4 as an off-white solid. TLC Rf=0.3 (10% ethyl acetate/hexanes). $^1$H NMR (300 MHz, $CDCl_3$) δ 7.78 (d, 1H, J=15.9 Hz), 7.68 (d, 1H, J=2.4 Hz), 7.66 (s, 1H), 7.59 (d, 1H, J=8.4 Hz), 7.43 (dd, 1H, J=9.0, 1.5 Hz), 6.78 (m, 1H), 6.47 (d, 1H, J=15.9 Hz), 4.27 (q, 2H, J=7.2 Hz), 1.34 (t, 3H, J=7.2 Hz).

3(S)-Benzofuran-6-yl-3-[benzyl-(1(R)-phenethyl)-amino]-propionic acid ethyl ester (1-5)

A solution of N-benzyl-α-(R)-methylbenzylamine (1.32 g, 6.30 mmol) in THF (25 mL) at 0° C. was treated with n-BuLi (2.52 mL of a 2.5 M soln in hexanes). The resulting solution was stirred at 0° C. for 30 min and then cooled to −78° C. A solution of acrylate 1-4 (0.681 g, 3.15 mmol) in THF (5 mL) was added. After stirring for 15 min at −78° C., satd. aq. NH$_4$Cl soln (5 mL) was added and the cold bath removed. The mixture was warmed to room temperature and extracted with Et$_2$O (2×40 mL). The combined organic extracts were washed with brine (30 mL), dried over MgSO$_4$, filtered, and concentrated. The residue was purified by flash chromatography (10% ethyl acetate/hexanes) to give the β-aminoester 1-5 as a yellow oil. TLC Rf=0.8 (10% ethanol/dichloromethane). $^1$H NMR (300 MHz, CDCl$_3$) δ 7.58 (m, 3H), 7.41 (m, 2H), 7.22 (m, 9H), 7.59 (s, 1H), 4.58 (m, 1H), 4.05 (m, 1H), 3.91 (q, 2H, J=7.1 Hz), 3.72 (m, 2H), 2.62 (m, 2H), 1.21 (d, 3H, J=7.2 Hz), 1.03 (t, 3H, J=7.1 Hz). 3(S)-Amino-3-(2,3-dihydro-benzofuran-6-yl)-propionic acid ethyl ester (1-6)

A mixture of the dibenzylamine 1-5 (1.19 g, 2.78 mmol) in EtOH/H$_2$O/AcOH (26 mL/3 mL/1.0 mL) was degassed with argon and treated with Pd(OH)$_2$ (1.19 g). The mixture was placed under 1 atm of H$_2$. After stirring for 18 h, the mixture was diluted with EtOAc, and filtered through celite. The filtrate was concentrated and the residue purified by flash chromatography (10% ethyl acetate/dichloromethane) to give the ester 1-6 as a white solid. TLC Rf=0.25 (10% ethanol/dichloromethane). $^1$H NMR (300 MHz, CD$_3$OD) as the trifluoroacetate salt: δ 7.25 (d, 1H, J=8.1 Hz), 6.88 (m, 1H), 7.66 (s, 1H), 6.82 (s, 1H1), 4.58 (m, 3H), 4.12 (m, 2H), 3.30 (m, 1H), 3.19 (m, 2H), 2.98 (m, 2H), 1.11 (t, 3H, J=7.2 Hz).

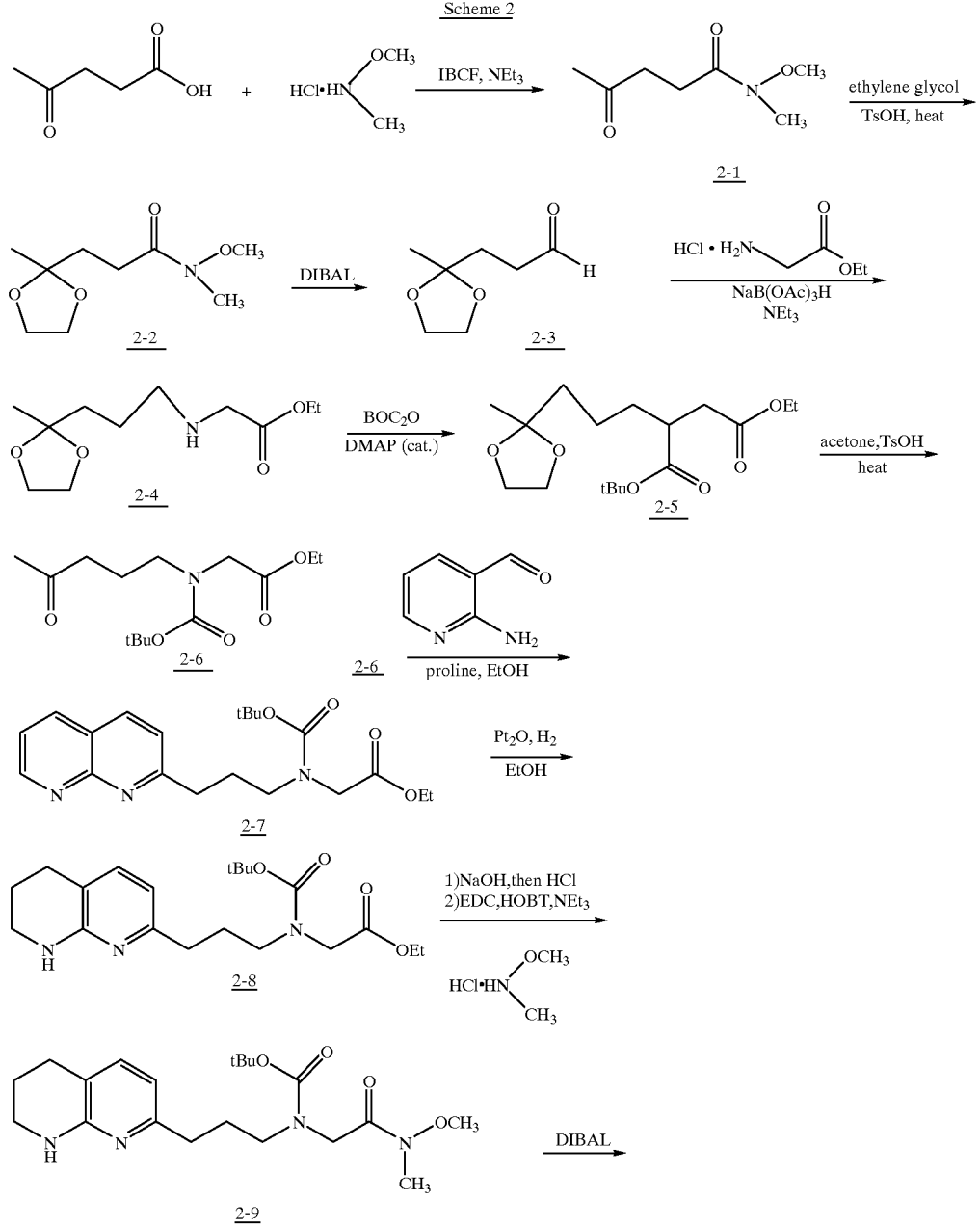

Scheme 2

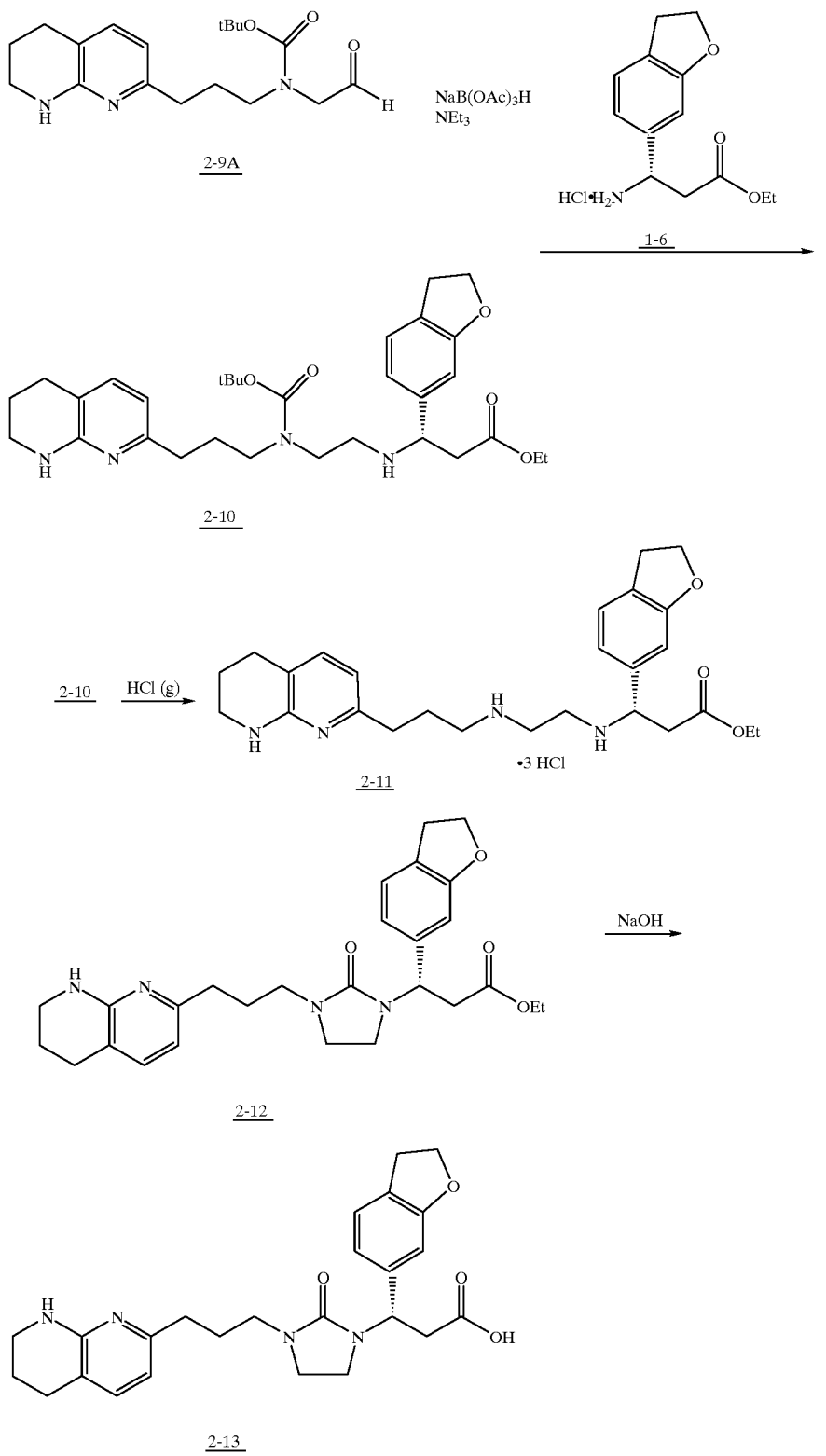

4-Oxo-pentanoic acid methoxy-methyl-amide (2-1)

To a stirred solution of levulinic acid (30 g, 0.258 mol) in CHCl$_3$ (850 mL) at 0° C. was added triethylamine (43.2 mL, 0.310 mol), followed by isobutyl chloroformate (37 mL, 0.284 mol) over 15 minutes. After 30 minutes, triethylamine (57.6 mL, 0.413 mol) was added, followed by N,O-dimethylhydroxylamine hydrochloride (37.8 g, 0.387 mol) in 5 portions over 5 minutes. Vigorous bubbling ensued, and the mixture was allowed to warm to RT and stirred for 1 h. The mixture was reduced to a moist solid by rotary evaporation under reduced pressure, slurried in 500 mL EtOAc, washed with 10% K$_2$CO$_3$, brine, and dried over Na$_2$SO$_4$. Evaporative removal of the solvent gave 2-1 as a yellow oil. TLC R$_f$=0.42 (silica,1:1 chloroform/ethyl acetate). $^1$H MM (300 MHz, CDCl$_3$) δ 3.74 (s, 3H), 3.18 (s, 3H), 2.65–2.95 (m, 4H), 2.21 (s, 3H).

N-methoxy-N-methyl-3-(2-methyl-[1.3]dioxolan-2-yl)-propionamide (2-2)

To a solution of 2-1 (38 g, 0.239 mol) in 500 mL benzene was added ethylene glycol (17.3 mL, 0.310 mol) and p-toluenesulfonic acid (1 g). The mixture was heated at reflux for 2 h with azeotropic removal of water. After cooling, the solution was washed with 200 mL sat. NaHCO$_3$, brine, and dried over Na$_2$SO$_4$. Evaporative removal of the solvent gave 2-2 as a yellow oil. TLC R$_f$=0.62 (silica, ethyl acetate). $^1$H NMR (300 MHz, CDCl$_3$) δ 3.95 (m, 4H), 3.68 (s, 3H), 3.17 (s, 3H), 2.51 (t, 2H, J=8 Hz), 2.00 (t, 3H, J=6 Hz) 1.33 (S, 3H).

3-(2-Methyl-[1,3]dioxolan-2-yl)-propionaldehyde (2-3)

To a solution of 2-2 (44.74 g, 0.22 mol) in 400 mL THF at −78° C. was added DIBAL (264 mL 1 M in hexanes, 0.264 mol) over 10 minutes. After stirring for 1 h, 350 ml of 1.0 M Rochelle's salt and 300 ml ether were added followed by the removal of the cooling bath. After stirring for 1 h, the organic portion was separated and dried over Na$_2$SO$_4$. Evaporative removal of the solvent gave 2-3 as a colorless oil. TLC R$_f$=0.80 (silica, ethyl acetate). $^1$H NMR (300 MHz, CDCl$_3$) δ 9.73 (s, 1H), 3.50 (d, 1H, J=16 Hz), 2.61 (d, 1H, J=21 Hz), 2.48 (m, 1H), 2.07 (t, 1H, J=7H), 1.33 (s, 3H).

[3-(2-Methyl-[1,3]dioxolan-2-yl)-propylamino]-acetic acid ethyl ester (2-4)

To a solution of 2- (31.7 g, 0.22 mol) in 1000 mL 1,2-dichloroethane at 0° C. were added glycine ethyl ester hydrochloride (61.5 g, 0.44 mol), triethylamine (107 mL, 0.77 mol), and NaB(OAc)$_3$H (65.3 g, 0.308 mol). The mixture was allowed to warm to RT and stirred for 15 h. The mixture was evaporated to one-third its initial volume, diluted with EtOAc and then washed with 10% K$_2$CO$_3$, brine, and dried over Na$_2$SO$_4$. Following evaporative removal of the solvent, the residue was chromatographed (silica gel, 1:1 chloroform/ethyl acetate followed by 5% MeOH/ethyl acetate) to give 2-4 as a yellow oil. TLC R$_f$=0.40 (silica, ethyl acetate). $^1$H NMR (300 MHz, CDCl$_3$) δ 6.01 (br s, 1H), 4.21 (m, 3H), 4.03 (d, 1H, J=5 Hz), 3.93 (m, 4H), 2.62 (t, 2H, J=8 Hz), 1.53–1.67 (m, 4H), 1.29 (m, 6H).

{Tert-butoxycarbonyl-[3-(2-methyl-[1,3]dioxolan-2-yl)-propyl]-amino}- acetic acid ethyl ester (2-5)

To a solution of 2-4 (24 g, 0.104 mol) in 100 mL THF were added a trace of DMAP, 20 drops of triethylamine, and BOC$_2$O (23.8 g, 0.109 mol). After 4 h, evaporative removal of the solvent gave 2-5 as a colorless oil. TLC R$_f$=0.38 (silica, 30% ethyl acetate/hexane). $^1$H NMR (300 MHz, CDCl$_3$, mixture of rotamers) δ 4.22 (m, 3H), 3.93 (m, 4H), 3.27 (m, 2H), 1.63 (m, 4H), 1.51 (s, 3H), 1.47 (s, 3H), 1.42 (s, 3H), 1.31 (s, 3H), 1.28 (m, 4H).

[Tert-butoxycarbonyl-(4-oxo-pentyl)-amino]-acetic acid ethyl ester (2-6)

To a solution of 2-5 (35 g, 0.1 mol) in 600 mL acetone was added p-toluenesulfonic acid (1 g). The mixture was heated at reflux for 2 h. After cooling, the mixture was evaporated to one-fifth its initial volume, diluted with EtOAc and then washed with sat. NaHCO$_3$, brine, and dried over Na$_2$SO$_4$. Evaporative removal of the solvent gave 2-6 as a yellow oil. TLC R$_f$=0.31 (silica, 30% ethyl acetate/hexane). $^1$H NMR (300 MHz, CDCl$_3$, mixture of rotamers) δ 4.20 (m, 2H), 3.92 (s, 0.85H), 3.83 (s, 1.15 H), 3.3 (m, 2H), 2.52 (m, 2H), 2.14 (s, 3H), 1.78 (m, 2H), 1.51–1.42 (3s, 9H), 1.28 (m, 3H).

[Tert-butoxycarbonyl-(3-[1,8]naphthyridin-2-yl-propyl)-amino]-acetic acid ethyl ester (2-7)

A solution of 2-6 (28 g, 97.4 mmol), 2-amino-3 formylpyridine (15.5 g, 127 mmol), proline (11.2 g, 97.4 mmol) in ethanol (250 mL) was heated at reflux for 15 h. After cooling and evaporation, the residue was chromatographed (silica gel, 1:1 chloroform/ethyl acetate) to give 2-7 as a yellow oil. TLC R$_f$=0.41 (silica, 70:25:5 chloroform/ethyl acetate/methanol) $^1$H NMR (300 MHz, CDCl$_3$) δ 9.09 (m, 1H), 8.14 (m, 2H), 7.43 (m, 2H), 4.17 (q, 2H, 7 Hz), 3.9 (2s, 2H), 3.43 (q, 2H, J=7 Hz), 3.07 (m, 2H), 2.18 (m, 2H), 1.42 (s, 9H), 1.25 (m, 3H).

{Tert-butoxycarbonyl-[3-(5,6,7,8-tetrahydro-[1,8] naphthyridin-2-yl)- propyl]-amino}-acetic acid ethyl ester (2-8)

A solution of 2-7 (24.3 g, 65.1 mmol), platinum oxide (4 g) and ethanol (130 mL) was stirred under a balloon of hydrogen gas for 6 h. Following filtration and evaporation, the residue was chromatographed (silica gel, ethyl acetate) to give 2-8 as a yellow oil. TLC R$_f$=0.35 (silica, 70:25:5 chloroform/ethyl acetate/methanol) $^1$H NMR (300 MHz, CDCl$_3$) δ 7.05 (d, 1H, J=6 Hz), 6.37 (m, 1H), 4.74 (brs, 1H), 4.18 (q, 2H, J=7 Hz), 3.9 (2s, 2H), 3.32 (m, 4H), 2.63 (m, 2H), 2.51 (m, 2H), 2.72 (m, 4H), 1.43 (m, 9H), 1.26 (m, 3H).

[(Methoxy-methyl-carbamoyl)-methyl]-[3-(5,6,7,8-tetrahydro- [1,8]naphthyridin-2-yl)-propyl]-carbamic acid tert-butyl ester (2-9)

To a solution of 2-8 (1.49 g, 3.96 mmol) in ethanol (8 mL) was added NaOH (4.36 mL 1M solution in water, 4.36 mmol). After stirring for 1 h at 50° C., HCl (4.75 mL of a 1M solution in water, 4.75 mmol) was added, and the mixture evaporated to give an oily residue. The residue was evaporated from ethanol three times, and then from acetonitrile three times, producing a yellow crusty solid which was dried under a vacuum of <2 mm Hg for 2 h. This residue was then slurried in chloroform (15 mL), and triethylamine (2.75 mL, 19.8 mmol), N,O-dimethylhydroxylamine hydrochloride (0.772 g, 7.92 mmol), HOBT (1 g) and EDC (0.91 g, 4.75 mmol) were added. After stirring for 15 h, the mixture was evaporated to dryness, the residue slurried in EtOAc, washed with sat. NaHCO$_3$, brine, and dried over Na$_2$SO$_4$. Evaporative removal of the solvent gave 2-9 as a yellow oil. TLC R$_f$=0.49 (silica, 70:25:5 chloroform /ethyl acetate /methanol) $^1$H NMR (300 MHz, CDCl$_3$) δ 7.05 (m, 1H), 6.38 (m, 1H), 4.81 (br s, 1H), 3.69, m, 3H), 3.37 (m, 4H), 3.18 (s, 3H), 2.64 (m, 2H), 2.53 (m, 2H), 1.88 (m, 4H), 1.44 (m, 9H).

{Tert-butoxycarbonyl-[3-(5,6,7,8-tetrahydro-[1,8] naphthyridin-2-yl)- propyl]-amino}-acetaldehyde (2-9A)

To a stirred solution of 2-9 (11.0 g, 28.0 mmol) and THF (300 ml) at −78° C. was added DIBAL (1.0M/hexanes, 42 ml, 42 mmol) dropwise over 20 minutes. After 1.0 hour, 300 ml of 1.0 M Rochelle's salt was added followed by the removal of the cooling bath. The mixture was stirred for 1.0 hour and then diluted with Et$_2$O. After 30 minutes of stirring, the organic portion was separated and dried over MgSO$_4$. Evaporative removal of the solvent gave crude aldehyde 2-9A as a colorless oil. TLC R$_f$=0.34 (silica,75:25:5 chloroform /EtOAc/MeOH).

3(S)-(2-{Tert-butoxycarbonyl-[3-(5,6,7,8-tetrahydro-[1,8] naphthyridin-2- yl)-propyl]-amino}-ethylamino)-3-(2,3-dihydro-benzofuran-6-yl)-propionic acid ethyl ester (2-10)

A mixture of the crude aldehyde 2-9A (9.1 mmol), 1-6 (3.2 g, 11.8 mmol), powdered molecular sieves (3 g) and DCE (100 mL) was stirred for 30 minutes. The mixture was cooled to 0° C. and then NaB(OAc)$_3$H (2.7 g, 12.7 mmol) was added. After 1 hour, the reaction was diluted with EtOAc and then washed with 10% $K_2CO_3$, brine, and dried over $MgSO_4$. Following evaporative removal of the solvent, the residue was chromatographed (silica gel, 1–3% [10:10:1 EtOH/$NH_4OH$/$H_2O$]1/50:50 chloroform/ethyl acetate) to give 2-10 as a yellow oil. TLC $R_f$=0.23 (silica, 5% [10:10:1 EtOH/NH4OH/H2O]/50:50 chloroform/ethyl acetate) $^1$H NMR (300 MHz, $CDCl_3$) δ 7.10 (d, J=7.6 Hz, 1H), 7.04 (d, J=7.3 Hz, 1H), 6.75 (m, 2H), 6.31 (d, J=7.3 Hz, 1H), 4.76 (s, 1H), 4.55 (t, J=8.6 Hz, 2H), 4.08 (m,2H), 4.00 (t, J=6.1 Hz, 1H), 3.41 (m, 2H), 3.16 (m, 6H), 2.68 (t, J=6.4 Hz, 1H), 2.59 (m, 3H), 2.48 (t, J=7.6 Hz, 2H), 1.81 (m, 4H), 1.39 (s, 9H), 1.21 (m, 3H).

3(S)-(2 3-Dihydro-benzofuran-6-yl)-3-{2-[3-(5,6,7,8-tetrahydro- [1,8]naphthyridin-2-yl)-propylamino]-ethylamino}-propionic acid ethyl ester (2-11)

HCl gas was rapidly bubbled through a solution of 2-10 (4.0 g, 7.2 mmol) in dioxane (160 ml) at 0° C. for 10 minutes. After 30 minutes, the solution was purged with argon for 30 minutes. The solution was concentrated to give the amine 2-11 as a yellow solid. $^1$H NMR (300 MHz, $CDCl_3$) δ 7.91 (s, 1H), 7.40 (d, J=7.0 Hz, 1H), 7.23 (d, J=7.6 Hz, 1H), 7.10 (m,2H), 6.56 (d, J=6.1 Hz, 1H), 4.58 (m, 2H), 4.04 (m,2H), 3.49 (m, 4H), 3.19 (m, 4H), 2.90 (m, 2H), 2.79 (m, 2H), 2.30 (m, 2H), 1.98(m, 2H), 1.85 (m, 5H), 1.15 (t, J=7.1 Hz, 3H).

3(S)-(2,3-Dihydro-benzofuran-6-yl)-3-{2-oxo-3-[3-(5,6,7, 8-tetrahydro- [1,8]naphthyridin-2-yl-)-propyl]-imidazolidin-1-yl}-propionic acid ethyl ester (2-12)

To a stirred mixture of 2-11 (11.8 mmol), $CH_2Cl_2$ (3 mL) and 20% $K_2CO_3$ was added phosgene (1.93 M toluene, 6.7 ml, 13.0 mmol) dropwise over 20 minutes. After stirring for 30 minutes, the organic layer was separated and dried over $MgSO_4$. Following evaporative removal of the solvent, the residue was chromatographed (silica gel, 5–10% methanol/ethyl acetate) to give 2-12 as a yellow oil. TLC $R_f$=0.25 (silica, 70:20:10 chloroform/ethyl acetate/methanol) $^1$H NMR (300 MHz, $CDCl_3$) δ 7.12 (d, J=7.6 Hz, 1H), 7.02 (d, J=7.3 Hz, 1H), 6.80 (d, J=7.6 Hz, 1H), 6.70 (s, 1H), 6.34 (d, J=7.3 Hz, 1H), 5.46 (t, J=7.9 Hz, 1H), 4.74 (s, 1H), 4.55 (t, J=8.9 Hz,2H), 4.10 (q, J=7.3 Hz, 2H), 3.41 (m, 2H), 3.21 (m, 6H), 2.95 (m,3H), 2.67(t, J=6.1 Hz, 2H), 2.52 (t, J=7.6 Hz, 2H), 1.88 (m, 5H), 1.20 (t, J=7.3 Hz, 3H).

3(S)-(2,3-Dihydro-benzofuran-6-yl)-3-{2-oxo-3-[3-(5,6,7, 8-tetrahydro- [1,8]naphthyridin-2-yl)-propyl]-imidazolidin-1-yl}-propionic acid (2-13)

To a solution of 2-12 (2.9 g, 6.06 mmol) in EtOH (15 mL) was added 1N NaOH (7.2 ml,7.2 mmol). After stirring for 2 h, the solvents were evaporated and the residue chromatographed (silica gel, 25:10:1:1 followed by 15:10:1:1 ethyl acetate/EtOH/water/$NH_4OH$) to give 2-13 as a white solid. TLC Rf=0.24 (15:10:1:1 ethyl acetate/EtOH/water/$NH_4OH$). $^1$H NMR (300 MHz, $CD_3OD$) δ 7.55 (d, J=7.3 Hz, 1H), 7.18 (d, J=7.6 Hz, 1H), 6.81 (d, J=6.1 Hz, 1H), 6.72 (s, 1H), 6.62 (d, J=7.3 Hz, 1H), 5.38 (t, J=7.9 Hz, 1H), 4.53 (t, J=8.9 Hz,2H), 3.14–3.53 (9H), 2.97 (m, 3H),2.80 (t, J=6.1 Hz, 2H), 2.67 (t, J=7.3 Hz, 2H), 1.93 (m,4H).

SCHEME 3

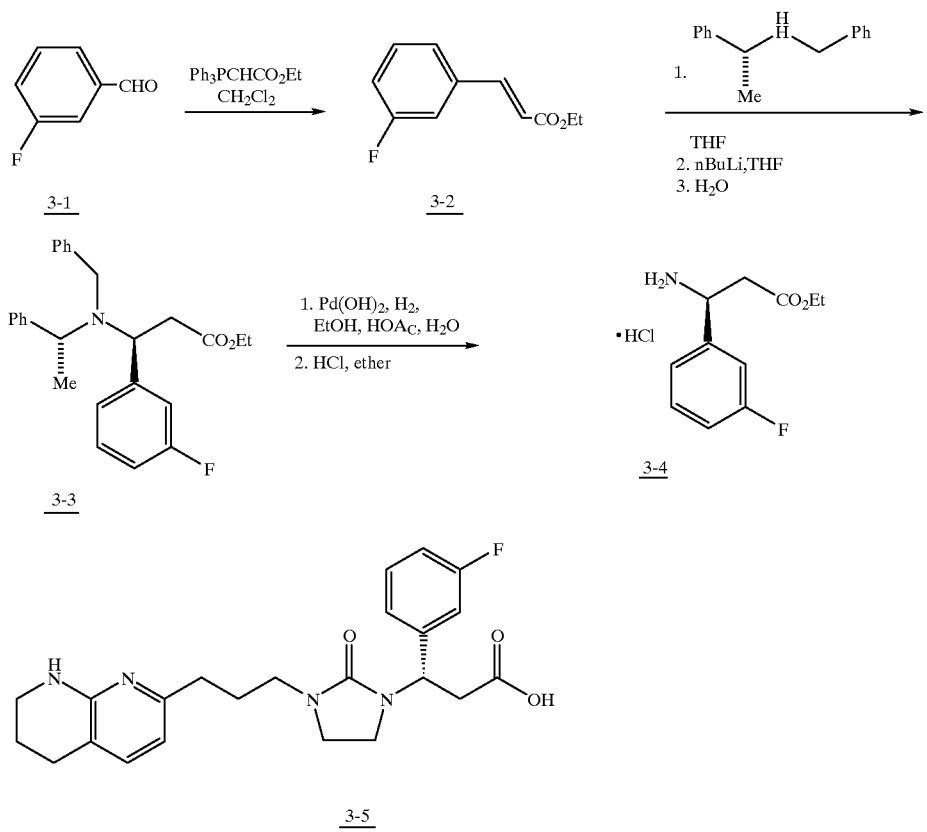

Ethyl 3-fluorocinnamate (3-2)

To a solution of 3-fluorobenzaldehyde 3-1 (18.16 g, 146 mmol) in dichloromethane (500 mL) was added ethyl (triphenylphosphoranylidene)acetate (61.2 g; 176 mmol) and the resulting solution was stirred at room temperature for 18 hr. After evaporation of the solvent, the residue was swirled with ether/hexane and filtered. The filtrate was concentrated and then purified on a plug of silica gel eluting with hexane/EtOAc 9:1. Removal of the solvent afforded the title compound 3-2 as an oil (~95% trans) which was used without further purification in the next step. $^1$H NMR (300 MHz, CDCl$_3$) δ 1.36 (3H, t), 4.28 (2H, q), 6.43 (1H, d), 7.08 (1H, m), 7.2–7.4 (3H, m), 7.64 (1H, d).

N-Benzyl-(R)-α-methylbenzyl-3(S)-fluorophenyl-β-alanine ethyl ester (3-3)

To a solution of N-benzyl-(R)-α-methylbenzylamine (33.4 g, 158 mmol) in THF (450 mL) at 0° C. was added n-butyllithium (1.6M in hexanes; 99 mL, 158 mmol). The dark violet solution was stirred at 0° C. for 30 minutes, cooled to −78° C., and the ester 3-2 (29.2 g, 150 mmol) in THF (100 mL) was added over 5 minutes. The resulting solution was stirred at −78° C. for 1 hr., then warmed to room temperature. After 2 hrs, the mixture was poured into water and extracted with EtOAc, washed with water, then brine, dried and concentrated in vacuo to give an oil. Column chromatography (silica gel; hexane/EtOAc 1:1 then pure EtOAc) gave the title compound 3-3. $^1$H NMR (300 MHz, CDCl$_3$) δ 1.06 (3H, t), 1.28 (3H, d), 2.52 (1H, dd), 2.62 (1H, dd), 3.66 (1H, d), 3.72 (1H, d), 3.95 (2H, q), 4.44 (1H, dd), 6.95 (1H, m), 7.1–7.5 (13H, m).

3(S)-Fluorophenyl-β-alanine ethyl ester hydrochloride (3-4)

A solution of the N-benzyl-(R)-α-methylbenzylamine 3-3 (28.2 g, 69.6 mmol) in ethanol (300 mL), acetic acid (30 mL) and water (3 mL) was degassed with argon for 30 minutes. Pd(OH)$_2$ on carbon (20% dry weight; 2.6 g) was added and the mixture then stirred under a hydrogen atmosphere (balloon) for 2 hours. The mixture was filtered through celite and the solvent removed in vacuo to give an oil. This oil was dissolved in 200 mL ether, and to this solution was added 60 mL 1N HCl in ether to yield a precipitate. Filtration and washing the solid with ether/hexane gave the title compound 3-4 as a white solid. $^1$H NMR (300 MHz, CD$_3$OD) δ 1.21 (3H, t), 3.0–3.2 (2H, m), 4.16 (2H, q), 4.76 (1H, t), 7.2–7.35 (3H, m), 7.5 (1H, m).

3(S)-(3-Fluorophenyl)-3-{2-oxo-3-[3-(5,6,7,8-tetrahydro-[1,8]naphthyridin- 2-yl)-propyl]-imidazolidin-1-yl}-propionic acid (3-5)

Compound 3-5 was prepared from 3-4 using the procedure for the preparation of 2-13. TLC Rf=0.36 (15:10:1:1 ethyl acetate/EtOH/water/NH$_4$OH). $^1$H NMR (300 MHz, CD$_3$OD) δ 7.41 (m, 2H), 7.09 (m, 3H), 6.54 (d, 1H, J=8.2 Hz), 5.48 (m, 1H), 3.51 (m, 2H), 3.46 (m, 3H), 3.23 (m, 2H), 2.94 (m, 2H), 2.81 (m, 4H), 2.63 (m, 2H), 1.93 (m, 2H), 1.19 (m, 2H, J=5.1 Hz).

SCHEME 4

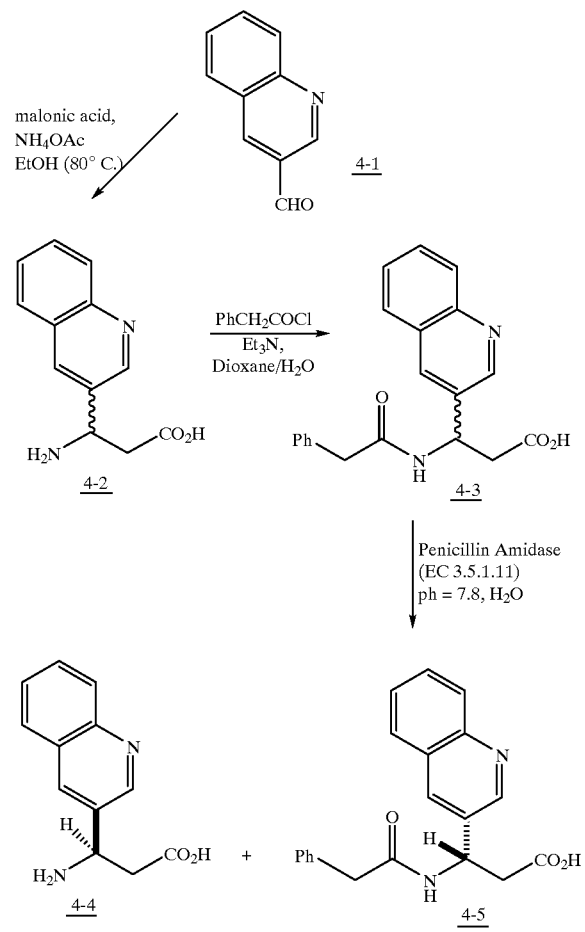

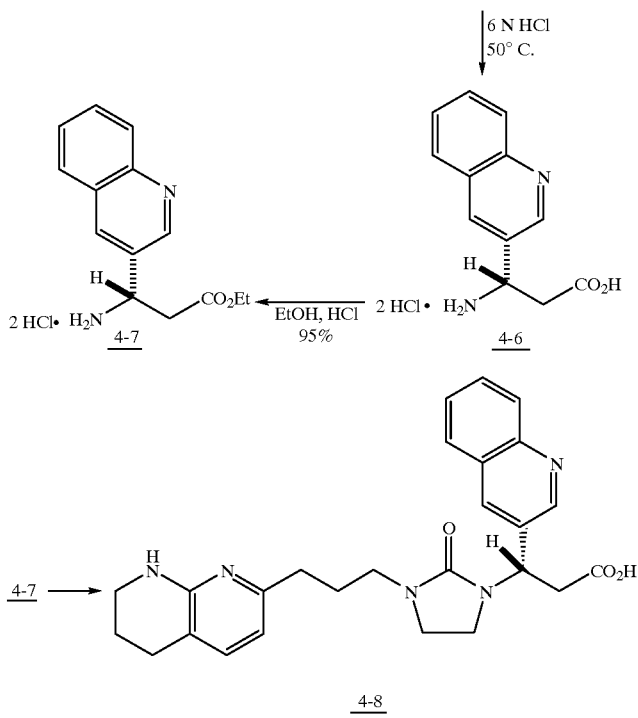

3-Quinolin-3-yl-propionic acid (4-2).

A solution containing quinoline-3-carboxaldehyde 4-1 (5 g, 31.8 mmol), malonic acid (3.6 g, 35.0 mmol), and ammonium acetate (5.0 g, 63.6 mmol) in anhydrous ethanol (125 mL) was heated at reflux for 12 h. After cooling to room temperature, the resulting white solid was collected by filtration and washed with cold ethanol (150 mL) and then dried under vacuum to provide 4-2 as a white solid (3.84 g, 17.8 mmol, 56%). $^1$H NMR (300 MHz, D$_2$O): δ 8.91 (d, J=2 Hz 1H), 8.21 (d, J=2 Hz, 1H), 8.12 (d, J=8 Hz, 1H), 7.84 (d, J=7 Hz, 1H), 7.72 (t, J=7 Hz, H), 7.54 (t, J=7 Hz, 1,H), 4.72 (m, 1H), 2.73 (m, 2H).

3-Phenylacetylamino-3-quinolin-3-yl-propionic (4-3)

A 0° C. solution of 4-2 (3.5 g, 16.2 mmol) and NaHCO$_3$ (2.7 g, 32.4 mmol) in 50% aqueous dioxane (100 mL) was treated dropwise with a solution of phenylacetyl chloride (3.00 g, 19.4 mmol) in 25 mL of dioxane. The resulting solution was stirred at 0° C. for 2.5h., then warmed to room temperature, diluted with H$_2$O (50 mL) and washed with ether (2×100 mL). The aqueous layer was adjusted to pH=3 with 3N HCl and then extracted with CH$_2$Cl$_2$ (3×150 mL). The pooled organic extracts were dried, filtered and concentrated to afford 4-3 as an off-white solid. $^1$H NMR (300 MHz, CD$_3$OD): δ 8.85 (d, J=2 Hz 1H), 8.20 (d, J=2 Hz, 1H), 8.00 (d, J=8 Hz, 1H), 7.86 (d, J=7 Hz, 1H), 7.76 (t, J=7 Hz, 1H), 7.52 (t, J=7 Hz, 1,H), 7.28 (m, 6H), 5.53 (t, J=6.8 Hz, 1H), 3.57 (s, 2H), 2.96 (m, 2H).

3-(S)-Quinolin-3-yl-propionic acid dihydrochloride (4-6)

Acid 4-3 (5.0 g, 15 mmol) was suspended in water (3.5 L), then treated with 1N NaOH (15 mL) to afford a clear solution. Penicillin amidase (Sigma, EC 3.5.1.11, 10,000 U) in 0.1 M phosphate buffer was added. The pH of the mixture was adjusted to 7.8 with 1N NaOH, and the solution was stirred at room temperature for 4 days. The reaction was monitored periodically by HPLC and the reaction stopped once the 50% conversion was reached. Next, the reaction solution was cooled to 0° C. and adjusted to pH=3 with 3N HCl. An oily yellow precipitate formed and was collected by filtration then washed with water to afford crude 4-5 (1.8 g, 5.3 mmol). The filtrate was extracted with CH$_2$Cl$_2$ (3×500 mL) to afford additional 4-5 contaminated by phenylacetic acid. Both batches of crude 4-5 were combined and stirred in 3 N HCl (200 mL) at 50° for 12 h., then cooled, washed with ether (2×100 mL) and evaporated to afford 4-6.

3-(S)-Quinolin-3-yl-propionic acid ethyl ester dihydrochloride (4-7).

The resolved acid 4 was converted to 4-7 by refluxing in ethanolic HCl. $^1$H NMR (300 MHz CD$_3$OD): δ 9.25 (d, J=2 Hz 1H), 8.31 (d, J=2 Hz, 1H), 8.15 (d, J=8 Hz, 1H), 7.84 (d, J=7 Hz, 1H), 7.72 (t, J=7 Hz, 1H), 7.54 (t, J=7 Hz, 1,H), 4.72 (m, 1H), 4.15 (q, J=6 Hz, 2H), 2.73 (m, 2H) 1.18 (t, J=6 Hz, 3H).

3(S)-(Quinolin-3-yl)-3-{2-oxo-3-[3-(5,6,7,8-tetrahydro-[1,8]naphthyridin-2-yl)-propyl]-imidazolidin-1-yl}-propionic acid (4-8).

Compound 4-8 was prepared from 4-7 using the procedure for the preparation of 2-13. $^1$H NMR (300 MHz, CD$_3$OD) δ 8.83 (m, 1H), 8.32 (m, 1H), 8.02 (m, 2H), 7.78 (m, 1H), 7.63 (m, 1H), 7.43 (d, 1H, J=7.3 Hz), 6.57 (d, 1H, J=7.3 Hz), 5.76 (m, 1H), 3.73 (q, 1H, J=8.2 Hz), 3.48 (m, 3H), 3.32 (m, 4H), 3.17 (m, 2H), 2.95 (m, 1H), 2.84–2.62 (,6H), 2.10 (m, 1H), 1.88 (m, 3H).

SCHEME 5
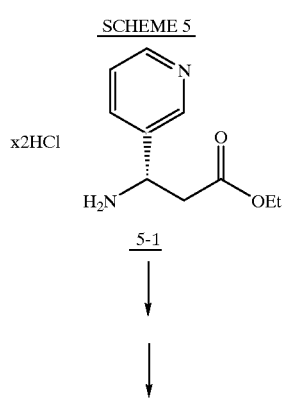
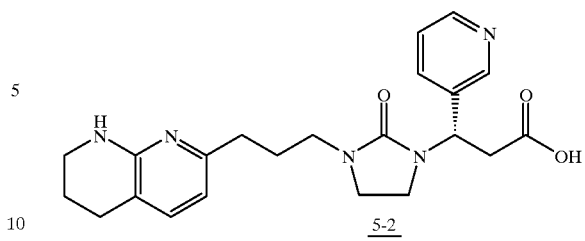
3(S)-(Pyridin-3-yl)-3-{2-oxo-3-[3-(5,6,7,8-tetrahydro-[1,8] naphthyridin-2- yl)-propyl]-imidazolidin-1-yl}-propionic acid (5-2)
Compound 5-2 was prepared from 5-1 (for preparation, see Zablocki et al., *J. Med. Chem.* 1995, 38, 2378) using the procedure for the preparation of 2-13. $^1$H NMR (300 MHz, CD$_3$OD) δ 8.54 (m, 1H), 8.47 (m, 1H), 7.85 (d, 1H, J=7.9 Hz), 7.46 (m, 2H), 6.55 (d, 1H, J=7.3 Hz), 5.57 (m, 1H), 3.63 (m, 2H), 3.46 (m, 3H), 3.18 (m, 2H), 3.01 (m, 2H), 2.77 (m, 4H), 2.60 (m, 2H), 2.05 (m, 1H), 1.93 (m, 3H). TLC (silica): Rf=0.09 (15 EtOAc/10 EtOH/1 NH$_4$OH/H$_2$O)
SCHEME 6

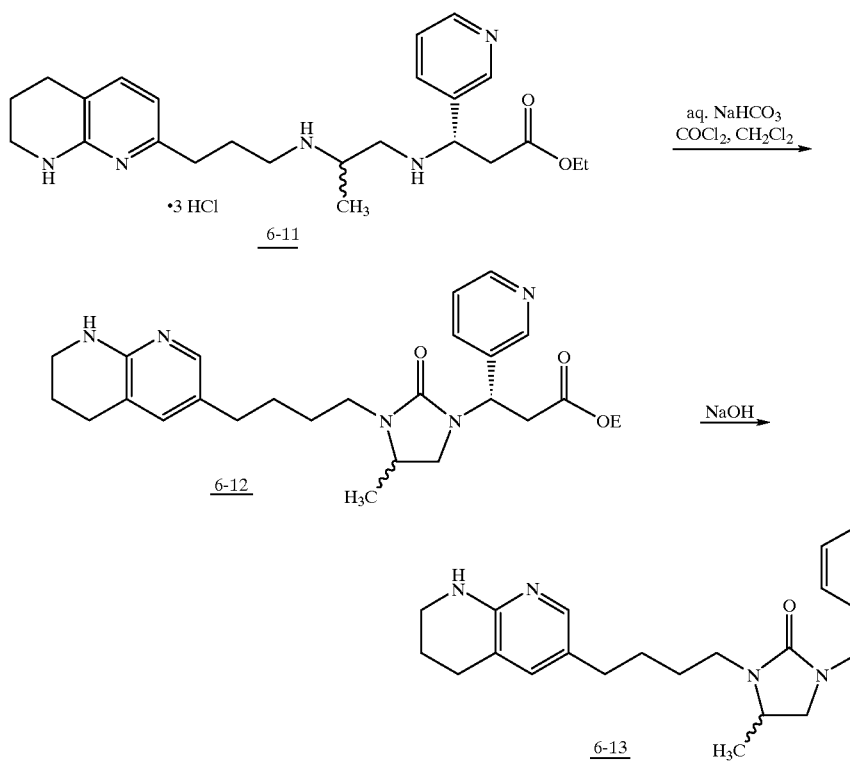

The imidazolidine-ring methylated compound 6-13 was prepared using the procedure described in Scheme 2 by replacing the glycine ethyl ester with alanine ethyl ester.

In further embodiments, other imidazolidine-ring substituted systems are prepared using the procedure described in Scheme 2 by employing the desired naturally-occurring or non- naturally-occurring amino acid.

SCHEME 7

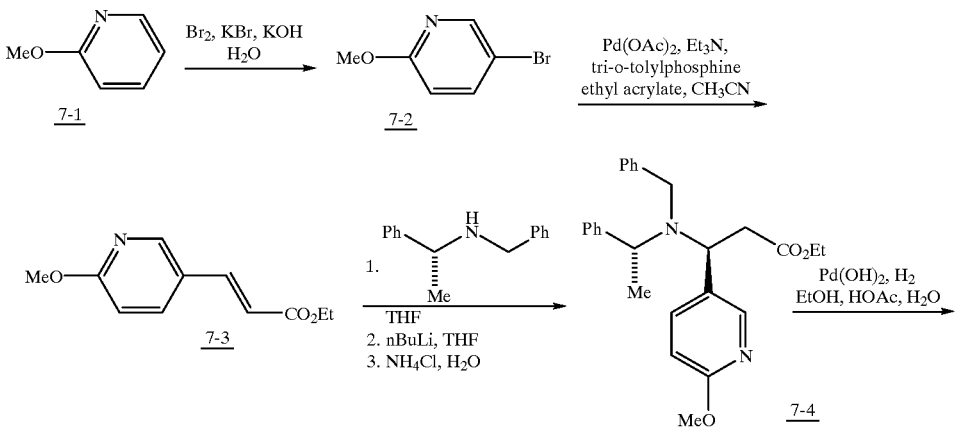

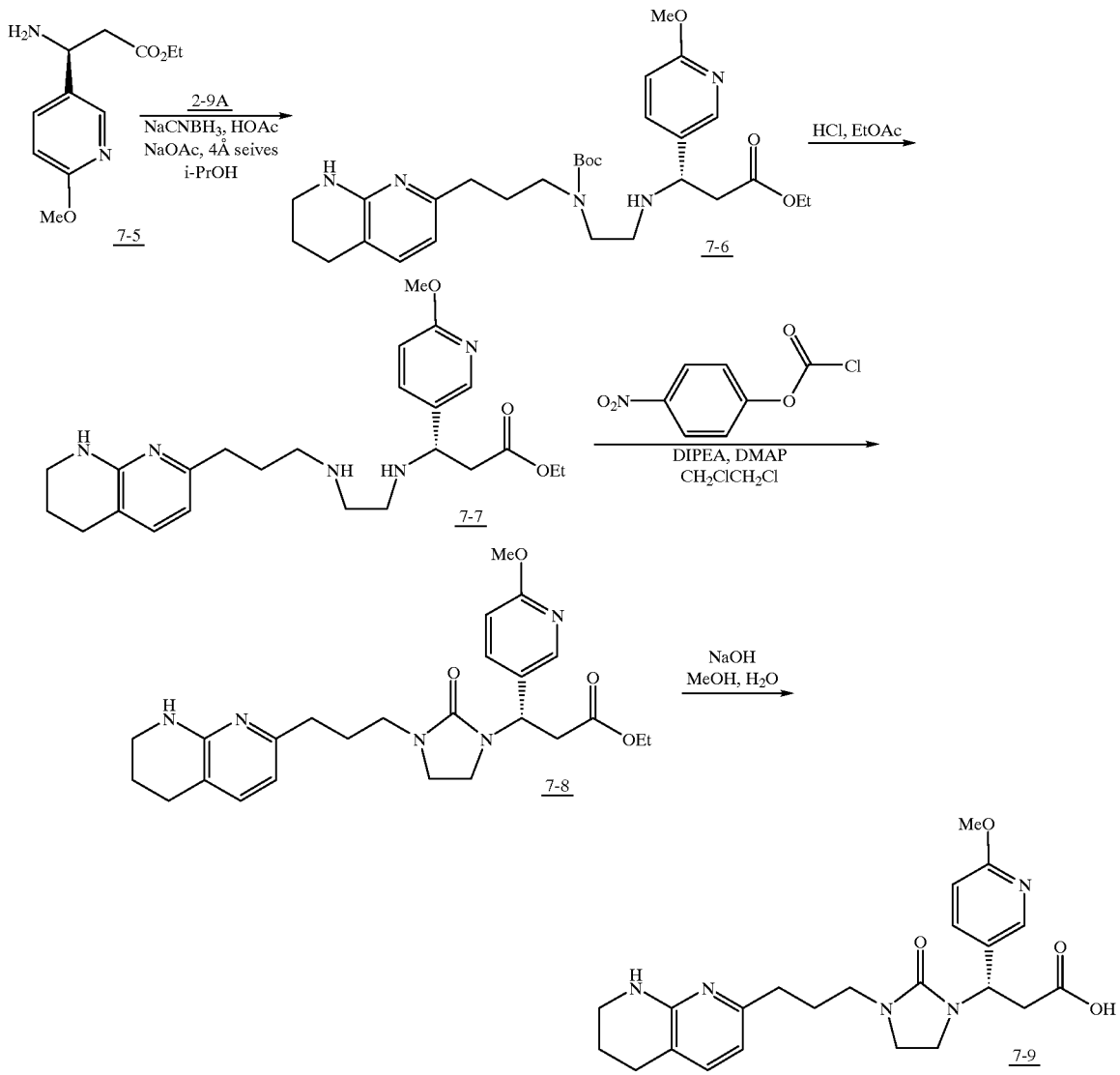

5-Bromo-2-methoxypyridine (7-2)

To a solution of KOH (4.2 g, 0.075 mol) in water (750 mL) was added 2-methoxypyridine 7-1 (16.4 g, 0.15 mol) followed by a dropwise addition of bromine (24 g, 0.15 mol) in 1N aqueous KBr (750 mL), and the resulting solution was stirred at room temperature for 5 hr. Solid NaHCO$_3$ was added until basic, and the solution was extracted with CHCl$_3$ (3×500 mL). The organic layer was washed with 10% NaHSO$_3$, then brine, dried over Na$_2$SO$_4$, filtered and the solvent removed in vacuo. The resulting dark brown oil was predominantly the desired compound 7-2 and was used as such in the next step. $^1$H NMR (300 MHz, CDCl$_3$) δ 3.91 (3H, s), 6.66 (1H, d), 7.62 (1H, dd), 8.20 (1H, d).

Ethyl 3-(6-methoxypyridin-3-yl)acrylate (7-3)

A solution of the 5-bromo-2-methoxypyridine 7-2 (74.3 g, 0.4 mol), ethyl acrylate (150 mL, 1.4 mol), triethylamine (150 mL, 1.08 mol), palladium acetate (10 g, 0.045 mol) and tri-o-tolylphosphine (20 g, 0.066 mol) in 100 mL acetonitrile was degassed with argon for 10 minutes. The mixture is heated at 90° C. for 12 hr, then the volatiles were removed in vacuo. Toluene (300 mL) was added and the mixture concentrated again. Diethyl ether (300 mL) was added and the mixture filtered through a pad of silica gel eluting with 800 mL of diethyl ether. After removal of the diethyl ether, the residue was chromatographed on silica gel eluting with EtOAc/hexane 1:19 then 1:14 then 1:9 to give 7-3 as a yellow solid. $^1$H NMR (300 MHz, CDCl$_3$) δ 1.34 (3H, t), 3.97 (3H, s), 4.26 (2H, q), 6.34 (1H, d),6.76 (1H, d), 7.63 (1H, d), 7.77 (1H, dd),8.27 (1H, d).

N-Benzyl-(R)-α-methylbenzyl-3(S)-(6-methoxypyridin-3-yl)-β-alanine ethyl ester (7-4)

To a solution of N-benzyl-(R)-α-methylbenzylamine (97.5 g, 462 mmol) in THF (750 mL) at 0° C. was added n-butyllithium (2.5M in hexanes; 178.5 mL, 446 mmol). The dark violet solution was stirred at 0° C. for 20 minutes, cooled to −78° C. and the ester 7-3 (63.7 g, 308 mmol) in THF (250 mL) was added over 60 minutes. The resulting solution was stirred at −78° C. for 1 hr., then cannulated into saturated NH$_4$Cl and extracted with EtOAc, washed with water then brine, dried and concentrated in vacuo to give an oil. Column chromatography (silica gel; hexane/EtOAc 9:1 then 4:1) gave 7-4 as an oil contaminated with N-benzyl-(R)-α-methylbenzylamine. This oil was taken up in 5% AcOH in water and extracted with diethyl ether (4×). The organic layers were dried over MgSO$_4$ and the solvent removed to give the title compound 7-4. $^1$H NMR (300 MHz, CDCl$_3$) δ 1.08 (3H, t), 1.27 (3H, d), 2.52 (1H, dd), 2.62 (1H, dd), 3.66 (1H, d), 3.70 (1H, d), 3.93 (3H, s), 3.95 (2H, m), 4.41 (1H, dd), 6.74 (1H, d), 7.15–7.45 (10H, m), 7.64 (1H, dd), 8.15 (1H, d).

3(S)-(6-methoxypyridin-3-yl)-β-alanine ethyl ester (7-5)

To a degassed (argon) solution of the ester 7-4 (70 g) in EtOH (250 mL), HOAc (25 mL) and water (2 mL) was added 20% Pd(OH)$_2$ on carbon. The mixture was placed under hydrogen using a balloon and the resulting mixture was stirred for 24 hr. After filtration through celite (washing with EtOAc), the solvent was removed in vacuo to afford a waxy solid. This was dissolved in 200 mL water and extracted with diethyl ether (2×200 mL). The aqueous layer was then treated with solid K$_2$CO$_3$ until fully saturated and extracted with EtOAc (4×200 mL). After drying over MgSO$_4$, the solvent was removed in vacuo to give the title compound 7-5 as an oil which solidified in the freezer. $^1$H NMR (300 MHz, CDCl$_3$) δ 1.23 (3H, t), 2.61 (1H, dd), 2.68 (1H, dd), 3.92 (3H, s), 4.15 (2H, q), 4.41 (1H, dd), 6.93 (1H, d), 7.62 (1H, dd), 8.13 (1H, d).

3(S)-(2-{tert-Butoxycarbonyl-[3-(5,6,7,8-tetrahydro-[1,8]naphthyridin-2-yl)- propyl]-amino}-ethylamino)-3-(2-methoxypyridin-5-yl)-propionic acid ethyl ester (7-6)

To a solution of the amine 7-5 (6.85 g, 30.5 mmol) in 2-propanol (300 mL) at room temperature was added acetic acid (1.75 mL, 30.5 mmol), NaOAc (24.6 g, 0.3 mol) and 4 Å molecular sieves (5 g). The aldehyde 2-9A (8.1 g, 24.3 mmol) in 2-propanol (150 mL,) was added and the mixture stirred for 15 minutes, then cooled to 0° C. and NaCNBH$_3$ (5.66 g, 90 mmol) added in one lot. The resulting mixture was allowed to warm to room temperature and stirred for 16 hr before being filtered through celite. After removal of the solvent in vacuo, the residue was treated with 10% aqueous KHSO$_4$ for 30 minutes, basified with solid K$_2$CO$_3$ (to pH ~10) and extracted with 3×200 mL EtOAc. The EtOAc layers were washed with brine, dried (Na$_2$SO$_4$) and concentrated in vacuo to give an oil. Column chromatography (silica gel; 5% MeOH in CHCl$_3$) gave 7-6 as an oil contaminated with ~7% of the β-alanine. $^1$H NMR (300 MHz, CDCl$_3$) δ 1.20 (3H, t), 1.42 (9H, s), 1.7–2 (4H, br m), 2.5–2.8 (8H, m), 3.2 (4H, m), 3.42 (2H, m), 3.92 (3H, s), 4.06 (2H, q), 5.0–5.4 (1H, bs), 6.36 (1H, br s), 6.72 (1H, d), 7.12 (1H, br s), 7.58 (1H, dd), 8.07 (1H, d).

3(S)-(6-Methoxypyridin-3-yl)-3-{2-[3-(5,6,7,8-tetrahydro-[1,8]naphthyridin- 2-yl)-propylamino]-ethylamino}-propionic acid ethyl ester (7-7)

A solution of the ester 7-6 (14.1 g, 26 mmol) in EtOAc (350 mL) cooled to −20° C. was treated with HCl (gas) for 10 minutes then stoppered and stirred at 0° C. for 1.5 hr. The volatiles were removed in vacuo, the residue taken up in 150 mL of water and treated with solid K$_2$CO$_3$ to pH~10. This solution was extracted with EtOAc (3×150 mL), washed with brine, dried (Na$_2$SO$_4$) and concentrated to give an oil. Column chromatography (silica gel; 5% MeOH in CHCl$_3$) gave the β-alanine 7-5; further elution with 5% MeOH in CHCl$_3$ saturated with NH$_3$ gave 7-7 as a viscous oil. $^1$H NMR (300 MHz, CDCl$_3$) δ 1.20 (3H, t), 1.8–1.95 (4H, m), 2.5–2.8 (12H, m), 3.39 (2H, m), 3.92 (3H, s), 4.09 (2H, q), 5.01 (1H, bs), 6.34 (1H, d), 6.72 (1H, d), 7.06 (1H, d), 7.59 (1H, dd), 8.07 (1H, d).

3(S)-(6-Methoxypyridin-3-yl)-3-{2-oxo-3-[3-(5,6,7,8-tetrahydro- [1,8]naphthyridin-2-yl)-propyl]-imidazolidin-1-yl}-propionic acid ethyl ester (7-8)

To a solution of the diamine 7-7 (8.03 g, 18.2 mmol), DIPEA 9.5 mL, 54.6 mmol) and DMAP (250 mg) in 1,2-dichloroethane (150 mL) cooled to −20° C. was added p-nitrophenyl chloroformate (3.85 g, 19.1 mmol) in 1,2-dichloroethane (25 mL) dropwise such that the internal temperature remains below −15° C. The resulting mixture was allowed to warm to 0° C. and stirred for 45 minutes, then heated to reflux for 4 hr. After cooling, the solvent was evaporated in vacuo, the residue taken up in EtOAc and washed successively with 10% K$_2$CO$_3$ (6×150 mL) and brine. The EtOAc layer was dried (Na$_2$SO$_4$) and concentrated in vacuo to give an oil (6.27 g). Column chromatography (silica gel; 5% EtOH in CH$_2$Cl$_2$) gave 7-8 as an oil. $^1$H NMR (300 MHz, CDCl$_3$) δ 1.20 (3H, t), 1.8–1.95 (4H, m), 2.52 (2H, dd), 2.68 (1H, dd), 2.9–3.1 (3H, m), 3.15–3.3 (5H, m), 3.39 (2H, m), 3.92 (3H, s), 4.11 (2H, q), 4.8 (1H, bs), 5.42 (1H, t), 6.34 (1H, d), 6.72 (1H, d), 7.03 (1H, d), 7.60 (1H, dd), 8.08 (1H, d).

3(S)-(6-Methoxypyridin-3-yl)-3-{2-oxo-3-[3-(5,6,7,8-tetrahydro- [1,8]naphthyridin-2-yl)-propyl]-imidazolidin-1-yl}-propionic acid (7-9)

To a solution of the ester 7-8 (3.48 g, 7.4 mmol) in MeOH (50 mL) and water (30 mL) at room temperature was added 1N NaOH solution (22.3 mL, 22.3 mmol) and the mixture stirred for 16 hr. After removal of the solvent in vacuo, the residue was treated with 25 mL 1N HCl and the solvent removed again. Column chromatography of the residue (silica gel;EtOAC/EtOH/aq. NH$_4$OH/H$_2$O 20:10:1:1 then 15:10:1:1) gave a gum which was crystallized from a minimum amount of water and filtered to give 7-9 as a white solid. $^1$H NMR (300 MHz, CD$_3$OD) δ 1.75–2.1 (4H, m), 2.55–3.1 (8H, m), 3.28 (1H, q), 3.3 (1H, m), 3.4–3.55 (3H, m), 3.63 (1H, q), 3.85 (3H, s), 5.47 (1H, dd), 6.55 (1H, d), 6.80 (1H, d), 7.48 (1H, d), 7.68 (1H, d), 8.09 (1H, d).

In a further embodiment, the R-enantiomer, i.e. 3(R)-(6-methoxypyridin-3-yl)-3-{2-oxo-3-[3-(5,6,7,8-tetrahydro-[1,8]naphthyridin- 2-yl)-propyl]-imidazolidin-1-yl}-propionic acid was prepared by substituting N-benzyl-(S)-α-methylbenzylamine for the N-benzyl-(R)-α-methylbenzylamine in preparing intermediate 7-4.

In yet a further embodiment, the racemate, i.e. 3-(6-methoxypyridin-3-yl)-3-{2-oxo-3-[3-(5,6,7,8-tetrahydro-[1,8]naphthyridin- 2-yl)-propyl]-imidazolidin-1-yl}-propionic acid was prepared by substituting racemic N-benzyl-α-methylbenzylamine for the N-benzyl-(R)-α-methylbenzylamine in preparing intermediate 7-4.

SCHEME 8

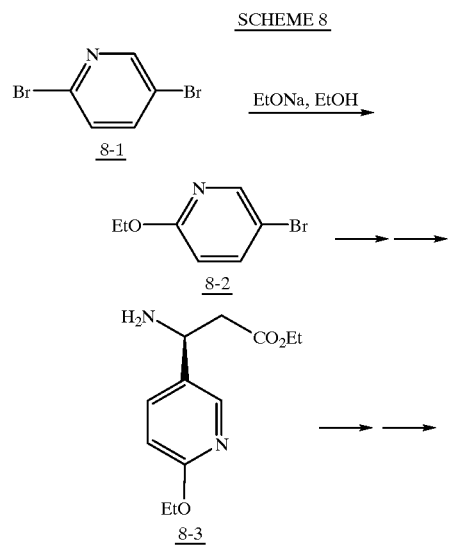

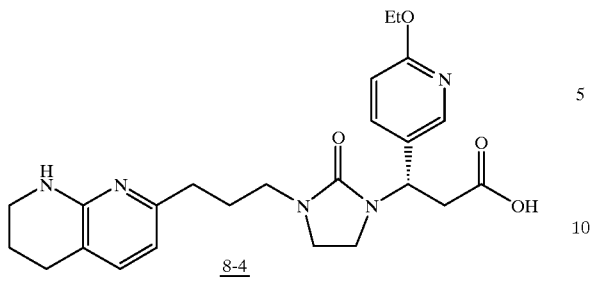

8-4

5-Bromo-2-ethoxypyridine (8-2)

Sodium metal (4.87 g, 0.212 mol) was added to ethanol (200 mL) and stirred until completely dissolved. To this solution was added 2,5-dibromopyridine 8-1 (Aldrich; 10 g, 0.0424 mol) and the resulting mixture was stirred at reflux for 16 hr. The solvent was removed in vacuo and the residue partitioned between water and EtOAc. After extraction with EtOAc (2×), the organic layer was washed with brine, dried (MgSO$_4$) and concentrated to give 8-2 as a red-brown solid which was used as such in the next step. $^1$H NMR (300 MHz, CDCl$_3$): δ 1.4 (3H, t), 4.33 (2H, q), 6.63 (1H, d), 7.62 (1H, dd), 8.19 (1H, d).

3(S)-(6-Ethoxypyridin-3-yl)-β-alanine ethyl ester (8-3)

The title compound 8-3 was prepared from 8-2 using the procedure described for the synthesis of 7-5. $^1$H NMR (300 MHz, CDCl$_3$): δ 1.25 (3H, t), 1.39 (3H, t), 2.61 (1H, dd), 2.67 (1H, dd), 4.15 (2H, q), 4.34 (2H, q), 4.40 (1H, dd), 6.71 (1H, d), 7.62 (1H, dd), 8.11 (1H, d).

3(S)-(6-Ethoxypyridin-3-yl)-3-{2-oxo-3-[3-(5,6,7,8-tetrahydro- [1,8]naphthyridin-2-yl)-propyl]-imidazolidin-1-yl}-propionic acid (8-4)

The title compound 8-4 was prepared from 2-9A and 8-3 using the procedure described in Scheme 2. $^1$H NMR (300 MHz, CD$_3$OD) δ 1.37 (3H, t), 1.8–2.0 (4H, m), 2.65 (2H, t), 2.82 (2H, t), 2.95–3.10 (2H, m), 3.15 (2H, m), 3.23 (2H, dt), 3.46 (2H, m), 3.51 (2H, t), 4.32 (2H, q), 5.41 (1H, t), 6.62 (1H, d), 6.84 (1H, d), 7.57 (1H, d), 7.76 (1H, dd), 8.13 (1H, d).

SCHEME 9

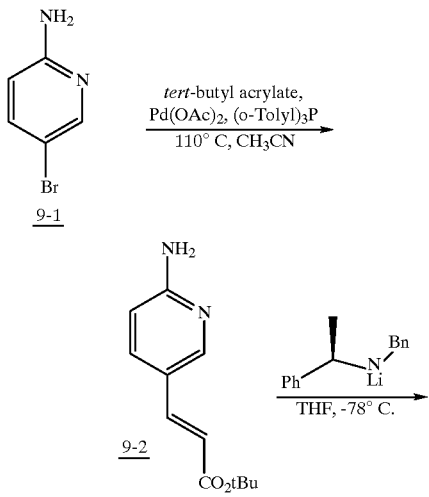

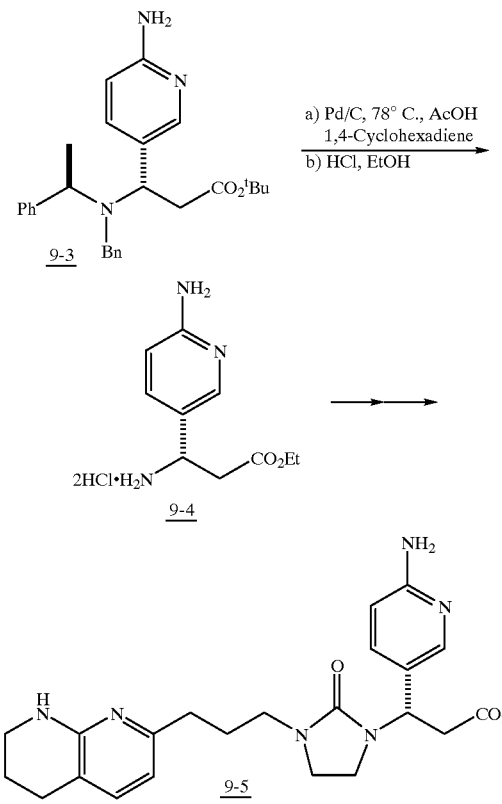

a) Pd/C, 78° C., AcOH
1,4-Cyclohexadiene
b) HCl, EtOH

3-(6-Amino-pyridin-3-yl)-acrylic acid tert-butyl ester (9-2)

A mixture of 2-amino-5-bromo-pyridine (9-1) (10 g, 58 mmol), tert-butyl acrylate (50 mL, 344 mmol), triethylamine (50 mL, 359 mmol), tri-o-tolylphosphine (3.0 g, 9.8 mmol) and Pd(OAc)$_2$ (1.0 g, 4.5 mmol) in 150 mL CH$_3$CN was purged with argon for 5 min and subsequently refluxed at 110° C. for 20 hr. The mixture was then cooled and concentrated. The residue was purified using silica gel flash chromatography (EtOAc/hexanes 1:1) to afford the desired product 9-2 as a solid.

Rf (silica, EtOAc/hexanes 1:1)=0.26

3(S)-(6-Amino-pyridin-3-yl)-3-[benzyl-( 1(R)-phenylethyl)-amino]-propionic acid tert-butyl ester (9-3)

To a cooled (0° C.) solution of (R)-(+)-N-benzyl-α-methylbenzylamine (4.0 g, 19 mmol) in 50 mL THF was gradually added n-butyllithium (11.3 mL, 2.5 M, 28.2 mmol) over 5 min. The mixture was stirred for 30 min at 0° C. and cooled to −78° C. A solution of 9-2 (2.0 g, 9.4 mmol) in 20 mL THF was gradually added. After stirring for 40 min at −78° C., it was treated with NH$_4$Cl (sat.) at −78° C., warmed to room temperature and extracted three times with EtOAc. The combined organic layers were washed with brine and dried over Na$_2$SO$_4$. After solvent evaporation, the residue was purified using silica gel flash chromatography (EtOAc/hexanes, 1:2) to afford the desired product 9-3 as an oil.

Rf (silica, EtOAc/hexanes 1:1)=0.28

3(S)-Amino-3-(6-amino-pyridin-3-yl)-propionic acid ethyl ester.2 HCl (9-4)

A mixture of 9-3 (0.5 g, 1.2 mmol) and 10% Pd/C (0.4 g) in 10 mL AcOH was purged with argon for 5 min and then heated at 78° C. 1,4-Cyclohexadiene (2 mL. 21.1 mmol) was then gradually added. The reaction mixture was stirred for 3 hr and filtered through a celite pad. The solution was concentrated and the residue was purified using silica gel flash chromatography (EtOAc/MeOH/NH$_4$OH 1:1:0.04) to afford an oil. To the oil (1.2 g) in 20 mL EtOH was introduced HCl gas for 10 min. The mixture was stirred 24 hr and then concentrated to afford the desired product 9-4 as the HCl salt.

$^1$H NMR (400 MHz, CD$_3$OD) δ 8.11 (d, J=9.6 Hz, 1H), 8.08 (s, 1H), 7.13 (d, J=9.6 Hz, 1H), 4.77 (m, 1H), 4.18 (q, J=6.8 Hz, 2H), 3.22–3.02 (m, 2H), 1.24 (t, J=6.8 Hz, 3H).

3(S)-(6-Amino-pyridin-3-yl)-3-{2-oxo-3-[3-(5,6,7,8-tetrahydro-[1,8]naphthyridin-2-yl)-propyl]-imidazolidin-1-yl}-propionic acid (9-5)

The title compound 9-5 was prepared as the TFA salt from 2-9A and 9-4 using the procedure described in Scheme 2.

$^1$H NMR (300 MHz, CD$_3$OD) δ 7.90 (d, J=2.1 Hz, 1H), 7.46 (dd, J=8.7, 2.1 Hz, 1H), 7.03 (d, J=8.7 Hz, 1H), 6.47 (d, J=8.7 Hz, 1H), 6.34 (d, J=8.7 Hz, 1H), 5.38–5.30 (m, 1H), 3.40–3.37 (m, 2H), 3.26–3.16 (m, 4H), 3.03–2.86 (m, 2H), 2.70–2.66 (m. 2H), 2.55–2.50 (m, 2H), 2.14–2.02 (m, 2H), 1.93–1.79 (m, 4H).

SCHEME 10

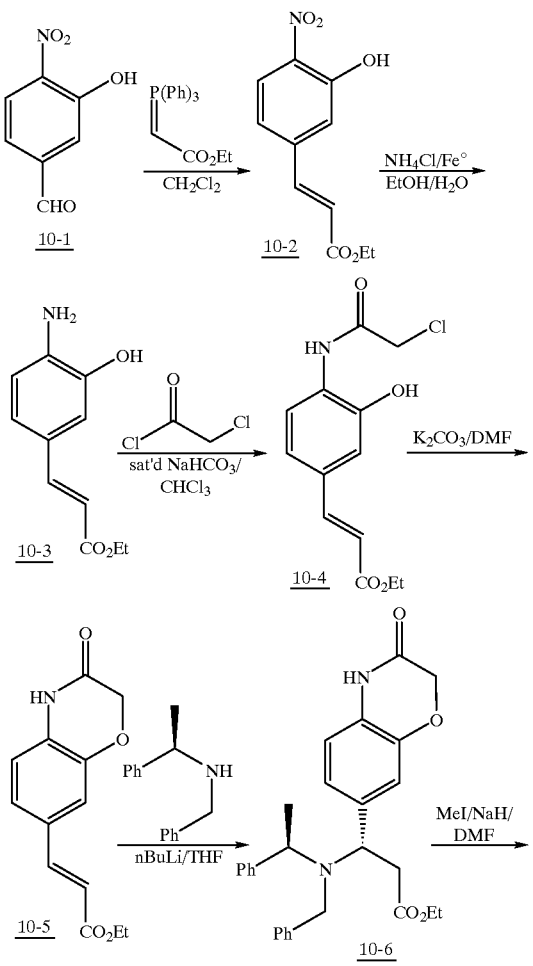

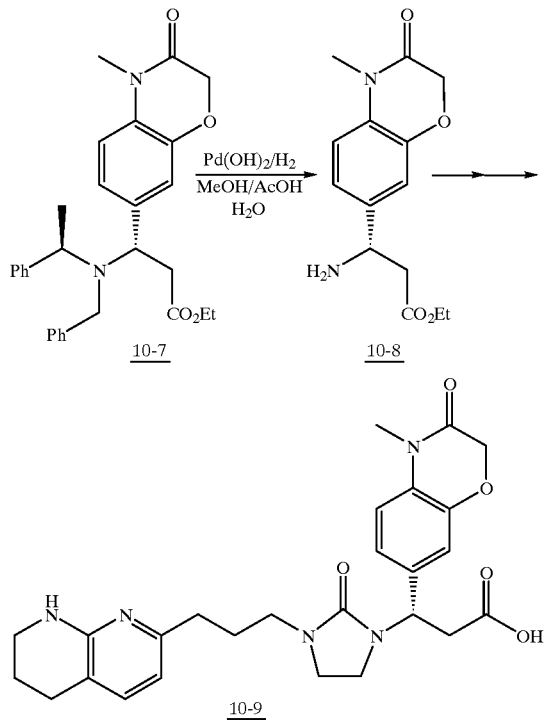

3-(3-Hydroxy-4-nitrophenyl)-acrylic acid ethyl ester (10-2)

To a stirred solution of aldehyde 10-1 (20.28 g, 132.5 mmol) in CH$_2$Cl$_2$ (400 mL) at room temperature was added (carbethoxymethylene)triphenylphosphorane (46.12 g, 132.5 mmol) over a 10 min period. The resulting orange solution was stirred at room temperature for 2 h. The solution was concentrated to one-fourth its volume. Flash chromatography (silica gel; 30:70 EtOAc/hexanes) gave the title compound 10-2 as a bright yellow solid.

TLC Rf=0.75 (25:75 EtOAc/hexanes)

$^1$H NMR (300 MHz, CDCl$_3$) δ 8.14 (d, 1H), 7.60 (d, 1H), 7.15 (dd, 1H), 6.54 (d, 1H), 4.30 (q, 2H), 1.36 (t, 3H).

3-(4-Amino-3-hydroxyphenyl)-acrylic acid ethyl ester (10-3)

To a stirred suspension of 10-2 (4.64 g, 19.6 mmol), NH$_4$Cl 524 mg, 9.8 mmol), EtOH (140 mL) and H$_2$O (70 mL) was added iron dust 2.72 g, 48.9 mmol). The resulting yellow suspension was refluxed for 1.5 h. and then the solution was filtered while hot through celite. The filtrate was concentrated and the residue was partitioned between EtOAc and brine. The layers were separated and the EtOAc layer dried (Na$_2$SO$_4$) and concentrated to give 10-3 which was used without further purification in the next step.

TLC Rf=0.2 (25:75 EtOAc/hexanes)

$^1$H NMR (300 MHz, CDCl$_3$) δ 7.57 (d, 1H), 7.00 (m, 2H), 6.68 (d, 1H, 6.20 (d, 1H), 4.26 (q, 2H), 4.10 (bs, 2H), 1.33 (t, 3H).

3-[4-(2-Chloroacetylamino)-3-hydroxyphenyl] acrylic acid ethyl ester (10-4)

To a stirred solution of 10-3 (3.38 g, 16.3 mmol) in CHCl$_3$ (80 mL) was added saturated NaHCO$_3$ (50 mL) and it was then chilled to 0° C. A solution of chloroacetyl chloride (1.94 mL, 24.4 mmol) in CHCl₃ (30 mL) was added dropwise to the chilled biphase. Upon addition completion, the reaction was stirred at 0° C. for 1 h. The layers were separated and the aqueous layer was extracted twice with EtOAc. The combined organic layers were washed with brine, dried (Na$_2$SO$_4$) and concentrated to give 10-4 which was used without further purification in the next step.

TLC Rf=0.4 (25:75 EtOAc/hexanes)
$^1$H NMR (300 MHz, CDCl$_3$): δ 10.33 (s, 1H), 9.58 (s, 1H), 8.02 (d, 1H), 7.51 (d, 1H), 7.19 (d, 1H), 7.12 (s, 1H), 6.39 (d, 1H), 4.42 (s, 2H), 4.17 (q, 2H), 1.25 (t, 3H).

3-(3-Oxo-3,4-dihydro-2H-benzo[1,4]oxazin-7-yl) acrylic acid ethyl ester (10-5)

To a stirred solution of 10-4 (4.28 g, 15.0 mmol) in DMF (50 mL) was added K$_2$CO$_3$ (4.50 g, 32.6 mmol). The resulting suspension was heated to 50° C. for 12 h., after which time the reaction was concentrated. The residue was partitioned between saturated NaHCO$_3$ and EtOAc and extracted twice with EtOAc. The combined organic layers were washed with brine, dried (Na$_2$SO$_4$), and concentrated. Flash chromatography (silica gel; 25:75 EtOAc/hexanes) yielded 10-5 as a beige solid.

TLC Rf=0.5 (25:75 EtOAc/hexanes).
$^1$H NMR (300 MHz, CDCl$_3$) δ 10.91 (s, 1H), 7.54 (d, 1H), 7.37 (s, 1H), 7.31 (d, 1H), 6.90 (d, 1H), 6.51 (d, 1H), 4.60 (s, 2H), 4.16 (q, 2H), 1.24 (t, 3H).

3(R)-[Benzyl-(1-phenylethyl)-amino]-3-(S)-(3-oxo-3,4-dihydro-2H-benzo[1,4]oxazin-7-yl) propionic acid ethyl ester (10-6)

To a stirred solution of (R)-(+)-N-benzyl-α-methylbenzylamine (5.43 g, 25.7 mmol) and anhydrous THF (75 mL) at 0° C. was added butyllithium (10.3 mL, 2.5 M/hexanes, 25.7 mmol) via syringe. The violet-red solution was stirred at 0° C. for 15 minutes and then cooled to −78° C. A solution of 10-5 (2.12 g, 8.6 mmol) in anhydrous THF (50 mL) was added via syringe, and the resulting brown solution was stirred at −78° C. for 30 minutes. The brown solution was quenched with saturated NH$_4$Cl, the mixture then warmed to room temperature and extracted twice with Et$_2$O. The combined organic layers were washed with brine, dried (Na$_2$SO$_4$), and concentrated. Flash chromatography (silica gel; 15:85 to 25:75 EtOAc/hexanes) yielded 10-6 as a white foam.

TLC Rf=0.25 (25:75 EtOAc/hexanes)
$^1$H NMR (300 MHz, CDCl$_3$) δ 10.89 (s, 1H), 7.32 (m, 10H), 7.10 (m, 2H), 6.91 (d, 1H), 4.62 (s, 2H), 4.39 (m, 1H), 4.13 (q, 2H) 3.96 (m, 1H), 3.68 (s, 2H), 2.56 (m, 2H), 1.28 (m, 6H).

3(R)-[Benzyl-(1-phenylethyl)-amino]-3-(S)-(4-methyl-3-oxo-3,4dihydro-2H-benzo[1,4]oxazin-7-yl) propionic acid ethyl ester (10-7)

To a stirred suspension of NaH (65 mg, 60%, 1.6 mmol) in DMF (5 mL) under argon was added a solution of 10-6 (650 mg, 1.4 mmol) in DMF (10 mL) via syringe. This yellow solution was stirred at room temperature for 30 minutes. Iodomethane (0.5 mL, 8.0 mmol) was added and the solution then stirred at room temperature for an additional 30 minutes. The reaction was quenched with saturated NaHCO$_3$. The aqueous layer was extracted three times with CH$_2$Cl$_2$. The combined organic layers were washed with brine, dried (Na$_2$SO$_4$) and concentrated. Flash chromatography (silica gel; 25:75 EtOAc/hexanes) afforded 10-7 as a clear oil.

TLC Rf=0.6 (25:75 EtOAc/hexanes)
$^1$H NMR (300 MHz, CDCl$_3$) δ 7.30 (m, 10H), 7.06 (m, 2H), 6.91 (d, 1H), 4.62 (s, 2H), 4.39 (m, 1H), 4.13 (q, 2H) 3.96 (m, 1H), 3.68 (s, 2H), 3.35 (s, 3H), 2.56 (m, 2H), 1.26 (m, 6H).

3(S)-Amino-3-(4-methyl-3-oxo-3,4-dihydro-2H-benzo[1,4]oxazin-7-yl) propionic acid ethyl ester (10-8)

A stirred solution of 10-7 (581 mg, 1.2 mmol), MeOH (10 mL), AcOH (1.0 mL), and H$_2$O (0.3 mL) was degassed with argon for 5 minutes. Pd(OH)$_2$ (581 mg) was added and the reaction was placed under 1 atm of H$_2$ for 2.5 h. The reaction was diluted with EtOAc and filtered through celite. The filtrate was concentrated to yield 10-8 as a clear oil.

TLC Rf=0.3 (5:95 MeOH/CH$_2$Cl$_2$)
$^1$H NMR (300 MHz, CDCl$_3$) δ 7.04 (m, 2H), 6.93 (dd, 1H), 4.61 (s, 2H), 4.39 (m, 1H), 4.13 (q, 2H), 3.37 (b, 2H), 3.35 (s, 3H), 2.69 (m, 2H), 1.24 (t, 3H).

3-(S)-(4-Methyl-3-oxo-3,4-dihydro-2H-benzo[1,4] oxazin-7-yl)-3-{2-oxo-3-[3-(5,6,7,8-tetrahydro-[1,8] naphthyridin-2-yl)-propyl]-imidazolidin-1-yl}-propionic acid (10-9)

The title compound 10-9 was prepared from 2-9A and 10-8 using the procedure described in Scheme 2.

$^1$H NMR (400 MHz, d$_6$-DMSO) δ 7.83 (bs, 1H), 7.60 (d, 1H), 7.11 (d, 1H), 6.99 (d, 1H), 6.93 (s, 1H), 6.63 (d, 1H), 5.20 (t, 1H), 4.64 (s, 2H), 3.3–2.8 (m, 10H), 3.25 (s, 3H), 2.72 (m, 2H), 2.59 (m, 2H), 1.81 (m, 2H), 1.74 (m, 2H).

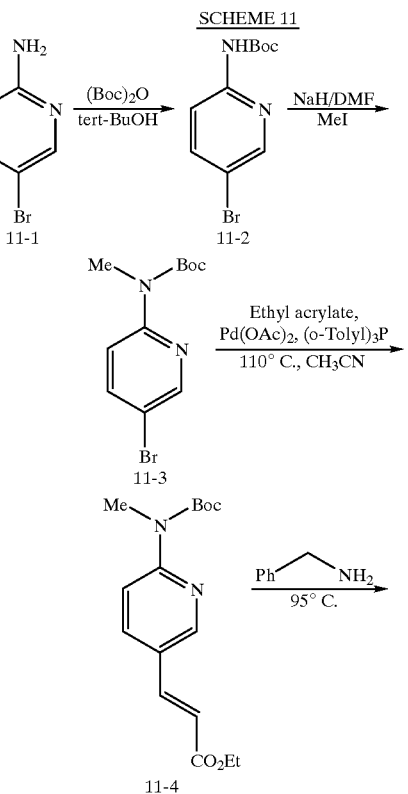

SCHEME 11

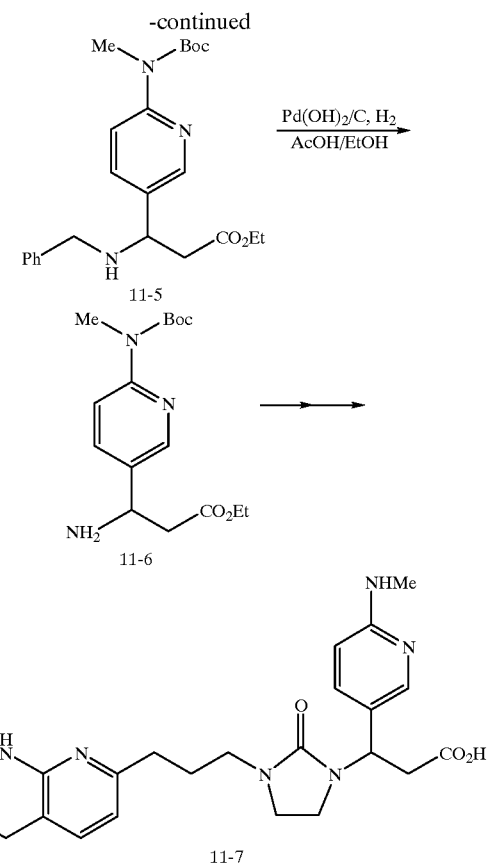

2-tert-Butoxycarbonylamino-5-aminopyridine (11-2)

A solution of 2-amino-4-bromopyridine 11-1 (10.1 g, 58.4 mmol) in 150 mL of melted t-BuOH was treated with di-tert-butyl dicarbonate (14.0 g, 64.2 mmol). After the solution was stirred for 12 hr, the solvent was evaporated. The residue was purified using silica gel flash chromatography (CHCl₃/hexanes, 5:1) to afford the desired product 11-2 as a solid.
Rf (silica, 100% CHCl₃)=0.56
¹H NMR (300 MHz, CDCl₃) δ 8.82 (bs, 1H), 8.38 (d, 1H), 8.78 (d, 1H), 7.78 (dd, 1H), 1.55 (s, 9H).

2-(tert-Butoxycarbonyl-methyl-amino)-5-aminopyridine (11-3)

To a solution of 11-2 (6.0 g, 22.0 mmol) in 50 mL DMF at 0° C. was added NaH gradually. After the mixture was stirred for 40 min, CH₃I (3.4 g, 24.0 mmol) was added in one portion. The reaction mixture was stirred for 5 hr, treated with 300 mL water and extracted three times with ethyl ether. The combined organic layers were washed with brine and dried over Na₂SO₄. After solvent removal, the residue was purified by silica gel flash chromatography (CHCl₃/hexanes 6:1) to afford the desired product 11-3 as a solid.
Rf (silica, 100% CHCl₃)=0.40
¹H NMR (300 MHz, CDCl₃) δ 8.40 (dd, 1H), 7.68 (m, 2H), 3.36 (s, 3H), 1.55 (s, 9H).

3-[6-(tert-Butoxycarbonyl-methyl-amino)-pyridin-3-yl]-acrylic acid ethyl ester (11-4)

A mixture of 11-3 (6.0 g, 20.9 mmol), ethyl acrylate (6.3 mL, 62.7 mmol), triethylamine (17 mL, 125.5 mmol), tri-o-tolylphosphine (1.3 g, 6.2 mmol) and Pd(OAc)₂ (0.5 g, 2.1 mmol) in 50 mL CH₃CN was purged with argon for 5 min and subsequently refluxed at 110° C. for 20 hr. The mixture was cooled and concentrated. The residue was purified using silica gel flash chromatography (EtOAc/hexanes 1:3) to afford the desired product 11-4 as an oil.
¹H NMR (300 MHz, CDCl₁₃) δ 8.47 (bs, 1H), 7.82 (m, 2H), 7.64 (d, 1H), 6.42 (d, 1H), 4.27 (q, 2H), 3.43 (s, 3H), 1.54 (s, 9H), 1.34 (t, 3H).

3-Benzylamino-3-[6-(tert-butoxycarbonyl-methyl-amino)-pyridin-3-yl]-propionic acid ethyl ester (11-5)

A mixture of 11-4 (1.7 g, 5.6 mmol) and benzylamine (8 mL, 73.2 mmol) was heated in a sealed-tube at 95° C. for 24 hr. The crude reaction mixture was purified using silica gel flash chromatography (EtOAc/hexanes 1:3 to 1:1) to afford the desired product 11-5 as an oil.
Rf (silica, EtOAc/hexanes 1:1)=0.63.

3-Amino-3-[6-(tert-butoxycarbonyl-methyl-amino)-pyridin-3-yl]-propionic acid ethyl ester (11-6)

A mixture of 11-5 (1.5 g 3.6 mmol), 20% Pd(OH)₂/C (0.3 g), AcOH (5.5 mL) and EtOH (50 mL) was purged with argon 3 times under vacuum. The reaction mixture was stirred under balloon hydrogenation condition for 16 hr and filtered through a celite pad. After solvent removal, the desired product 11-6 was obtained as the acetate salt.
¹H NMR (300 MHz, CDCl₃) δ 8.38 (d, 1H), 7.70 (m, 2H), 4.50 (dd, 1H), 4.15 (q, 2H), 3.40 (s, 3H), 2.80 (m, 2H), 1.25 (t, 3H).

3-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid (11-7)

The title compound 11-7 was prepared as the TFA salt from 2-9A and 11-6 using the procedure described in Scheme 2.
¹H NMR (300 MHz, CD₃OD) δ 7.92 (dd, J=9.6, 1.6 Hz, 1H), 7.79 (d, J=1.6 Hz, 1H), 7.57 (d, J=7.6 Hz, 1H), 7.03 (d, J=9.6 Hz, 1H), 6.63 (d, J=7.6 Hz, 1H), 5.28 (m, 1H), 3.51–3.36 (m, 5H), 3.28–3.17 (m, 3H), 3.05 (m, 2H), 3.02 (s. 3H), 2.82 (m, 2H), 2.67 (m, 2H), 1.98–1.84 (m, 4H).

SCHEME 12

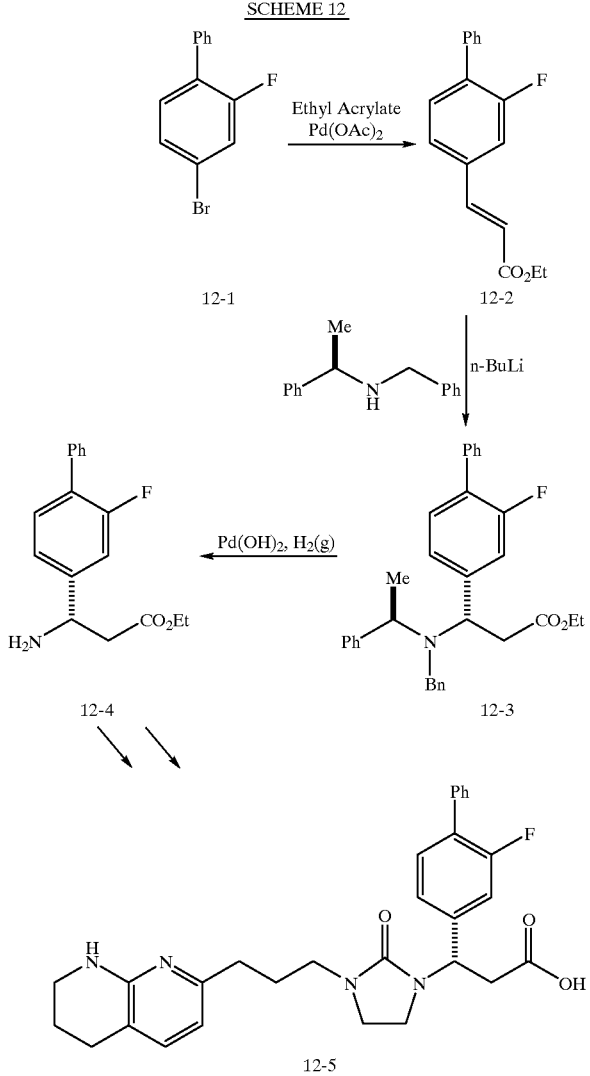

3-(2-Fluoro-biphenyl-4-yl)-acrylic acid ethyl ester (12-2)

A solution of 2-fluoro-4-bromobiphenyl 12-1 (7.5 gm, 31.8 mmol), ethyl acrylate (4.3 mL), Pd(OAc)$_2$ (0.714 gm, 3.2 mmol), tri-o-tolylphosphine (1.94 gm, 1.5 mmol), and triethylamine (12 mL) was heated to 100° C. in a sealed tube for 12 h. The reaction was cooled to room temperature and diluted with dichloromethane (40 mL). The organic solution was washed with 10% aq. citric acid (20 mL), satd. aq. NaHCO$_3$, and brine (20 mL). The organic solution was dried over MgSO$_4$, filtered, and concentrated. The residue was purified by flash chromatography (95:5 to 90:10 hexanes/EtOAc) to give the acrylate ester 12-2 as a white solid. TLC Rf=0.44 (10% ethyl acetate/hexanes).

3-[Benzyl-(1(R)-phenylethyl)-amino]-3-(2-fluoro-biphenyl-4yl)-propionic acid ethyl ester (12-3)

A cooled (0° C.) solution of (R)-(+)-N-benzyl-α-methylbenzylamine (8.9 mL, 42.6 mmol) in THF (100 mL) was treated with n-butyllithium (26.6 mL of a 1.6 M soln in hexanes; 42.6 mmol). After stirring for 10 min, the purple solution was cooled to −78° C. and treated with a solution of ester 12-2 (5.76 g, 21.3 mmol) in THF (10 mL). After stirring for 20 min, the solution was quenched with satd aq NH$_4$Cl soln (5 mL), and the cold bath removed. The reaction mixture was diluted with Et$_2$O (100 mL), and washed with 10% aq citric acid (50 mL), satd aq NaHCO$_3$ (50 mL), 5% aq acetic acid (30 mL), 10% aq K$_2$CO$_3$ (50 mL), and brine (50 mL). The solution was dried over MgSO$_4$, filtered and concentrated. The residue was purified by flash chromatography (90:10 hexanes/EtOAc) to give adduct 12-3. TLC Rf=0.48 (10% ethyl acetate/hexanes).

3-Amino-3-(2-fluoro-biphenyl4-yl)-propionic acid ethyl ester (12-4)

A solution of the dibenzylamine 12-3 (5.65 gm, 11.75 mmol) in EtOH/HOAc (90/10 mL) was purged with argon and treated with Pd(OH)$_2$ (3 g) and placed under 1 atm of H$_2$ gas for 12 h. Additional portions (2.5 g) of Pd(OH)$_2$ were added after 24 h, 48 h and 144 h. The reaction mixture was purged with argon, filtered through Celite, and the filtrate dissolved in aq HCl (pH=1). The aqueous solution was washed with EtOAc, neutralized with satd aq NaHCO$_3$, and extracted with EtOAc (3×30 mL). The combined organic solutions were washed with brine, dried over MgSO$_4$, filtered and concentrated to give the desired product 12-4.

¹H NMR (300 MHz, CD₃OD) δ 7.41 (m, 8H), 4.10 (m, 1H), 4.06 (m, 2H), 2.73 (m, 2H), 1.18 (m, 3H) ppm.

3(S)-(2-Fluoro-biphenyl-4yl)-3-{2-oxo-3-[3-(5,6,7,8-tetrahydro-[1,8]napthyridin-2-yl)-propyl]-imidazolidin-1-yl} propionic acid (12-5)

The title compound 12-5 was prepared from 2-9A and 12-4 using the procedure described in Scheme 2.

¹H NMR (300 MHz, CD₃OD) δ 7.49 (m, 9H), 6.64 (d, J=7.3 Hz, 1H), 5.49 (m, 1H), 3.31 (m, 9H), 2.83 (m, 2H), 2.74 (m, 2H), 1.97 (m, 4H) ppm.

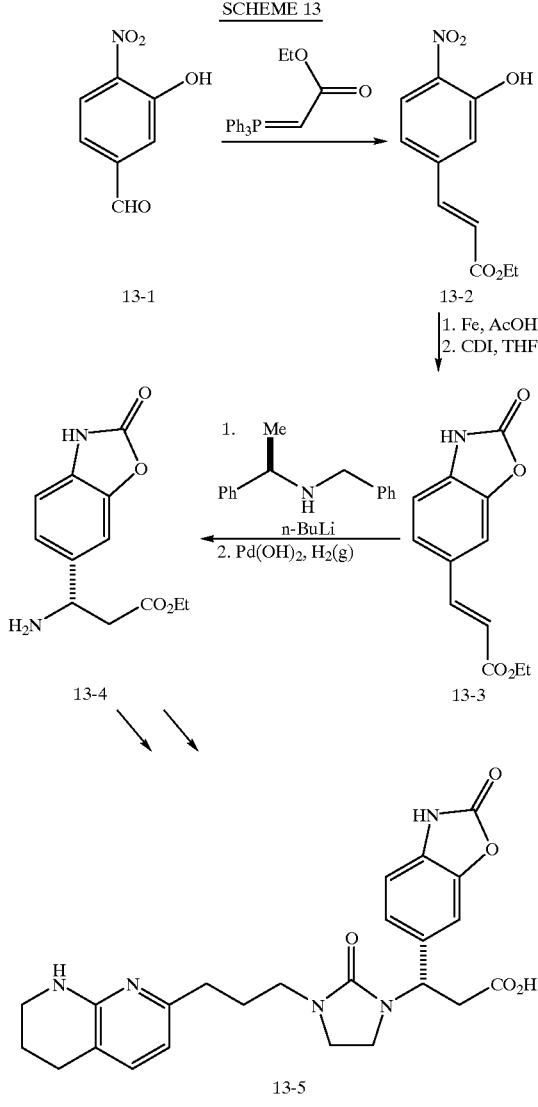

3-(3-Hydroxy-4-nitro-phenyl)-acrylic acid ethyl ester (13-2)

To a solution of aldehyde 13-1 (15.0 g, 98.0 mmol) in CH₂Cl₂ (300 mL) was slowly added carboethoxymethylenetriphenylphosphorane (34.1 g, 98.0 mmol). The orange solution was stirred for 12 h at ambient temperature. The solution was concentrated to a paste and purified by flash chromatography (10% EtOAc/(CH₂Cl₂) to give 13-2 as a yellow solid.

TLC Rf=0.51 (30% ethyl acetate/hexanes).
¹H NMR (300 MHz, CD₃OD) δ 8.08 (d, J=8.4 Hz, 1H), 7.63 (d, J=16.2 Hz, 1H), 7.35 (d, J=1.5 Hz, 1H), 7.27 (dd, J=8.4, 1.5 Hz, 1H), 6.65 (d, J=15.9 Hz, 1H), 4.25 (q, J=7.2 Hz, 2H), 1.32 (t, J=6.9 Hz, 3H) ppm.

3-(2-Oxo-2,3-dihydro-benzoxazol-6-yl)-acrylic acid ethyl ester (13-3)

To a solution of the nitrophenol 13-2 (12.0 g, 57.4 mmol) in warm (70° C.) AcOH/H₂O (200 mL) was added iron dust (9.61 g, 172.2 mmol). The brown heterogeneous mixture was stirred for 30 min at 70–80° C. The mixture was filtered hot through Celite, and the Celite bed washed with EtOAc (2×200 mL). The filtrate was cautiously neutralized with satd aq NaHCO₃ (3×100 mL). The solution was dried over MgSO₄, filtered, and concentrated. The residue was purified by flash chromatography (5% MeOH in CH₂Cl₂) to give an orange solid (9.6 g, 81%). A portion of this solid (4.5 g, 21.7 mmol) was dissolved in THF (150 mL) and treated with 1,1-carbonyldiimidazole (3.87 g, 23.8 mmol), and the solution was stirred at ambient temperature for 24 h. The solution was diluted with EtOAc (100 mL) and washed with 10% HCl (50 mL) and brine (50 mL). The solution was dried over MgSO₄, filtered, and concentrated. The residue was purified by flash chromatography (5% MeOH in CH₂Cl₂) to give 13-3 as a yellow solid.

TLC Rf=0.49 (5% MeOH/CH₂Cl₂).
¹H NMR (300 MHz, CD₃OD) δ 7.77 (d, J=15.9 Hz, 1H), 7.55 (s, 1H), 7.41 (d, J=8.4 Hz, 1H), 7.09 (d, J=8.1 Hz, 1H), 6.47 (d, J=15.9 Hz, 1H), 4.22 (q, J=7.2 Hz, 2H), 1.31 (t, J=7.2 Hz, 3H) ppm.

3(S)-Amino-3-(2-oxo-2,3-dihydro-benzoxazol-6-yl)-propionic acid ethyl ester (13-4)

A solution of (R)-(+)-N-benzyl-α-methylbenzylamine (4.08 g, 19.3 mmol) in THF (120 mL) at 0° C. was treated with n-BuLi (7.72 mL of a 2.5 M soln in hexanes). The resulting solution was stirred at 0° C. for 30 min and then cooled to −78° C. A solution of acrylate 13-3 (1.5 g, 6.43 mmol) in THF (20 mL) was added. After stirring for 15 min at −78° C., satd aq NH₄Cl soln (25 mL) was added and the cold bath removed. The mixture was warmed to room temperature and extracted with Et₂O (2×40 mL). The combined organic extracts were washed with brine (30 mL), dried over MgSO₄, filtered, and concentrated. The residue was purified by flash chromatography (30% ethyl acetate/hexanes) to give 2.74 g of the β-aminoester as a yellow oil. The aminoester was dissolved in EtOH/H₂O/AcOH (54 mL/4.8 mL/1.2 mL), degassed with argon, and treated with Pd(OH)₂ (2.74 g). The mixture was placed under 1 atm of H₂. After stirring for 18 h, the mixture was diluted with EtOAc and filtered through Celite. The filtrate was concentrated to give ester 13-4 as an off-white solid.

TLC Rf=0.10 (5% MeOH/CH₂Cl₂).
¹H NMR (300 MHz, CD₃OD) δ 7.34 (s, 1H), 7.26 (dd, J=1.2, 8.1 Hz, 1H), 7.12 (d, J=8.1 Hz, 1H), 4.65 (t, J=7.2 Hz, 1H), 4.13 (q, J=6.9 Hz, 2H), 2.98 (m, 2H), 1.20 (t, J=7.2 Hz, 3H) ppm.

3(S)-(2-Oxo-2,3-dihydro-benzoxazol-6-yl)-3-{2-oxo-3-[3-(5,6,7,8-tetrahydro-[1,8]napthyridin-2-yl)-propyl]-imidazolidin-1-yl} propionic acid (13-5)

The title compound 13-5 was prepared from 2-9A and 13-4 using the procedure described in Scheme 2.

¹H NMR (300 MHz, CD₃OD) δ 7.57 (d, J=7.3 Hz, 1H), 7.28 (s, 1H), 7.19 (d, J=8.2 Hz, 1H), 6.63 (d, J=7.3 Hz, 1H), 5.47

(m, 1H), 3.30 (m, 9H), 2.82 (m, 2H), 2.66 (m, 2H), 1.96 (m, 6H) ppm.

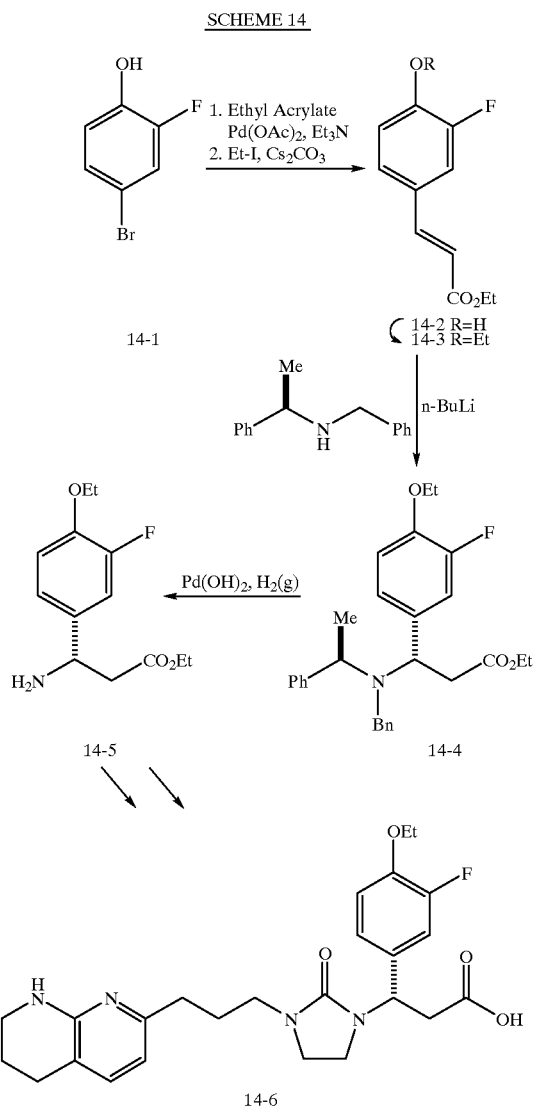

SCHEME 14

3-(4-Hydroxy-3-fluorophenyl)-acrylic acid ethyl ester (14-2)

A solution of 2-fluoro-4-bromophenol 14-1 (50 g, 261.8 mmol), ethyl acrylate (34 mL), Pd(OAc)$_2$ (2.5 g), tri-o-tolylphosphine (5 g) and triethylamine (83 mL) was heated to 100° C. in a sealed tube for 12 h. The reaction was cooled to room temperature and diluted with dichloromethane (100 mL). The organic solution was washed with 10% aq. citric acid (40 mL), satd aq NaHCO$_3$, and brine (40 mL). The organic solution was dried over MgSO$_4$, filtered and concentrated. The residue was purified by flash chromatography (50:50 hexanes/EtOAc to 100% EtOAc) to give acrylic acid 14-2 as a white solid.
TLC Rf=0.45 (50% ethyl acetate/hexanes).

3-[Benzyl-(1(R)-phenylethyl)-amino]-3-(4-ethoxy-3-fluorophenyl)-propionic acid ethyl ester (14-4)

To a stirred solution of 14-2 (49.25 gm, 234.5 mmol) in DMF (600 mL) was added Cs$_2$CO$_3$ (84.1 gm, 257.9 mmol) and ethyl iodide (18.8 mL, 234.5 mmol). After stirring for 12 h at room temperature, the reaction mixture was diluted with EtOAc (1L) and washed with water (6×300 mL), 10% aq. citric acid (200 mL), satd. aq. NaHCO$_3$ (200 mL), and brine (300 mL). The organic solution was dried over MgSO$_4$, filtered, and concentrated to give 52.9 g (95%) of the product 14-3 as an orange oil which crystallized upon standing. A cooled (0° C.) solution of (R)-(+)-N-benzyl-α-methylbenzylamine (71 mL, 339.4 mmol) in THF (650 mL) was treated with n-butyllithium (212 mL of a 1.6 M soln in hexanes; 339.4 mmol). After stirring for 10 min, the purple solution was cooled to −78° C. and treated with a solution of ester 14-3 (53.8 g, 226.3 mmol) in THF (100 mL). After stirring for 20 min, the solution was quenched with satd aq NH$_4$Cl soln (50 mL), and the cold bath removed. The reaction mixture was diluted with Et$_2$O (1000 mL), and washed with 10% aq citric acid (300 mL), satd aq NaHCO$_3$ (300 mL), 5% aq acetic acid (300 mL), 10% aq K$_2$CO$_3$ (300 mL), and brine (200 mL). The solution was dried over MgSO$_4$, filtered and concentrated. The residue was purified by flash chromatography (85:15 hexanes/EtOAc) to give the adduct 14-4.

TLC Rf=0.39 (25% ethyl acetate/hexanes).

3-Amino-3-(4-Ethoxy-3-fluorophenyl)-propionic acid ethyl ester (14-5)

A solution of the dibenzylamine 14-4 (30.0 gm, 66.8 mmol) in EtOH/HOAc (340/30 mL) was purged with argon and treated with Pd(OH)$_2$ (6 g) and placed under 1 atm of H$_2$ for 12 h. Additional portions (2.5 g) of Pd(OH)$_2$ were added after 24 h and 48 h. The reaction mixture was purged with argon, filtered through Celite, and the filtrate collected. The filtrate was concentrated to yield the desired amine 14-5.

$^1$H NMR (300 MHz, CD$_3$OD) δ 7.19 (m, 3H), 4.62 (m, 1H), 4.07 (m, 4H), 2.99 (m, 2H), 1.39 (m, 3H) 1.18 (m, 3H) ppm.

3-(S)-(4-Ethoxy-3-fluorophenyl)-3-{2-oxo-3-[3-(5,6,7,8-tetrahydro-[1,8]napthyridin-2-yl)-propyl]-imidazolidin-1-yl} propionic acid (14-6)

The title compound 14-6 was prepared from 2-9A and 14-5 using the procedure described in Scheme 2.

$^1$H NMR (300 MHz, CD$_3$OD) δ 7.45 (d, J=7.3 Hz, 1H), 7.04 (m, 3H), 6.53 (d, J=7.3 Hz, 1H), 5.43 (m, 1H), 4.06 (q, J=7.0 Hz, 2H), 3.48 (m, 6H), 3.15 (m, 1H), 2.78 (m, 6H), 2.55 (m, 2H), 1.96 (m, 3H), 1.38 (t, J=7.0 Hz, 3H) ppm.

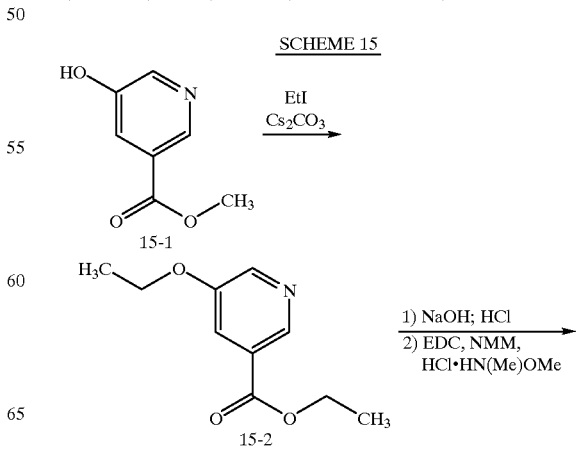

SCHEME 15

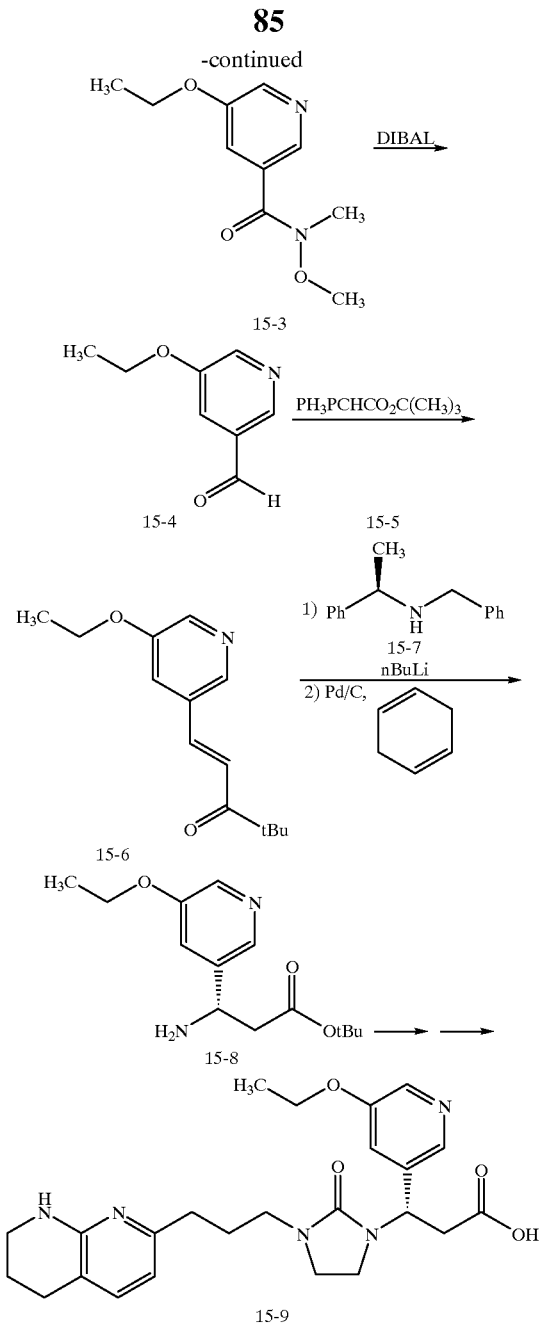

h, the solvents were evaporated and the residue was dissolved in 1N HCl (80 ml, 80 mmol) and then concentrated, azeotroped with $CH_3CN$ to give the crude acid. The crude acid was suspended in DMF (200 mL) and then treated with HCl.HN(Me)OMe (13.9 g, 144 mmol), EDC (15.1 g, 79.2 mmol), HOBT (9.6 g, 72 mmol) and NMM (60 mL, 576 mmol). The mixture was stirred for 18 hours and then concentrated. The residue was dissolved in ethyl acetate, washed with 10% $K_2CO_3$, brine, dried ($MgSO_4$), and concentrated to give amide 15-3 as a brown oil.

TLC $R_f$=0.30 (silica, 70:25:5 chloroform/ethyl acetate/MeOH)

5-Ethoxy-pyridine-3-carbaldehyde (15-4)

To a stirred solution of 15-3 (14.0 g, 66.5 mmol) and $CH_2Cl_2$ (200 mL) at -78° C. under argon was added DIBAL (1.0M hexanes, 90 ml) dropwise over 30 minutes. After 30 minutes, the solution was warmed to 0° C. for 1 hour. The reaction was quenched with 100 ml 1.0M Rochelle's salt, stirred for 1.0 hour and then extracted with $Et_2O$. The organic layer was dried ($MgSO_4$), and then concentrated to give the aldehyde 15-4 as a brown oil.

TLC $R_f$=0.32 (silica, 70:25:5 chloroform/ethyl acetate/MeOH)

$^1$H NMR (300 MHz, $CDCl_3$) δ 10.10 (s, 1H),8.65 (s,1H), 8.55 (s,1H), 7.59 (s, 1H), 4.14 (q, 2H, J=7 Hz), 1.43 (t, 3H, J=7 Hz).

3-(5-Ethoxy-pyridin-3-yl)-acrylic acid tert-butyl ester (15-6)

A mixture of 15-4 (8.0 g, 51.6 mmol), 15-5 (20 g, 54.2 mmol), and benzene (150 mL) was heated to reflux for 30 minutes. The mixture was diluted with $Et_2O$ and then washed with 10% $K_2CO_3$, brine and dried ($MgSO_4$). Following evaporative removal of the solvent, the residue was chromatographed (silica gel, 30% EtOAc/hexanes) to give 15-6 as a yellow solid.

TLC $R_f$=0.41 (silica, 70:25:5 chloroform/ethyl acetate/MeOH)

$^1$H NMR (300 MHz, $CDCl_3$) δ 8.31 (m, 2H),7.55 (d, 1H, J=6 Hz), 7.27 (s, 1H), 6.40 (d, 1H, J=16 Hz), 4.10 (q, 2H, J=7 Hz), 1.54 (s, 9H), 1.44 (m, 3H).

3(S)-Amino-3-(5-ethoxy-pyridin-3-yl)-propionic acid tert-butyl ester (15-8)

To a stirred solution of 15-7 (500 mg, 2.38 mmol) and THF at 0° C. was added nBuLi (2.5 M THF, 0.95 ml) dropwise. After 20 minutes, the solution was cooled to -78° C. and 15-6 (500 mg, 1.98 mmol), dissolved in 3 ml THF, was added. After 15 minutes, the reaction was quenched with sat. $NH_4Cl$ followed by the removal of the cooling bath. The solution was extracted with ethyl acetate. The organic portion was washed with brine, dried ($MgSO_4$) and concentrated. The residue was dissolved in acetic acid (14 ml), and the solution was purged with argon for 30 minutes. 10% Pd/C (1.0 g) was added and the mixture was heated to 80° C. 1,4-Cyclohexadiene (6 ml) was added dropwise maintaining an internal temperature between 80° C. and 90° C. After 5.0 hours, the mixture was filtered through a celite pad, concentrated and then azeotroped with toluene. The residue was chromatographed (silica gel, 5% [10:10:1 EtOH/$NH_4OH/H_2O$]/70:25:5 chloroform/ethyl acetate/MeOH) to give 15-8 as a yellow solid.

$^1$H NMR (300 MHz, $CDCl_3$) δ 8.18 (m, 2H),7.25 (s,1H,), 4.41 (m,1H,), 4.08 (q, 2H, J=7 Hz), 2.59 (m, 2H, ), 1.87 (s, 2H), 1.40 (m, 12H).

5-Ethoxy-nicotinic acid ethyl ester (15-2)

A mixture of 3-hydroxy-nicotinic acid methyl ester 15-1 (15 g, 90.8 mmol), ethyl iodide (14.5 ml, 181.6 mmol), cesium carbonate (29.5 g, 90.8 mmol) and DMF (150 mL) was stirred at ambient temperture for 3 hours. The reaction mixture was diluted with $Et_2O$ and then washed with 10% $K_2CO_3$, brine, dried ($MgSO_4$), and concentrated to give the ester 15-2 as a red oil.

TLC $R_f$=0.52 (silica,75% EtOAc/hexanes)

$^1$H NMR (300 MHz, $CDCl_3$) δ 8.82 (s, 1H), 8.46 (s,1H), 7.75 (s, 1H), 4.40 (q, 2H, J=7 Hz), 4.12 (q, 2H, J=7 Hz), 1.43 (m, 6H).

5-Ethoxy-N-methoxy-N-methyl-nicotinamide (15-3)

To a solution of 15-2 (15 g, 72 mmol) in EtOH (100 mL) was added 1N NaOH (80 ml, 80 mmol). After stirring for 1

3(S)-(5-Ethoxy-pyridin-3-yl)-3-{2-oxo-3-[3-(5,6,7,8-tetrahydro-[1,8]naphthyridin-2-yl)-propyl]-imidazolidin-1-yl}-propionic acid (15-9)

The title compound 15-9 was prepared from 2-9A and 15-8 using the procedure described in Scheme 2.
TLC Rf=0.27 (silica, 10:10:1:1 ethyl acetate/EtOH/water/NH$_4$OH).
$^1$H NMR (300 MHz, CD$_3$OD) δ 8.13 (m, 2H), 7.48 (d, 1H, J=7 Hz), 7.35 (s, 1H), 6.55 (d, J=8 Hz, 1H,), 5.53 (m, 1H), 4.13 (q, 2H, 7 Hz), 3.31–3.70 (m, 7H), 3.06 (m, 2H), 2.55–2.85 (m, 6H), 1.88–2.15 (m,5H), 1.42 (t, 3H, J=7 Hz).

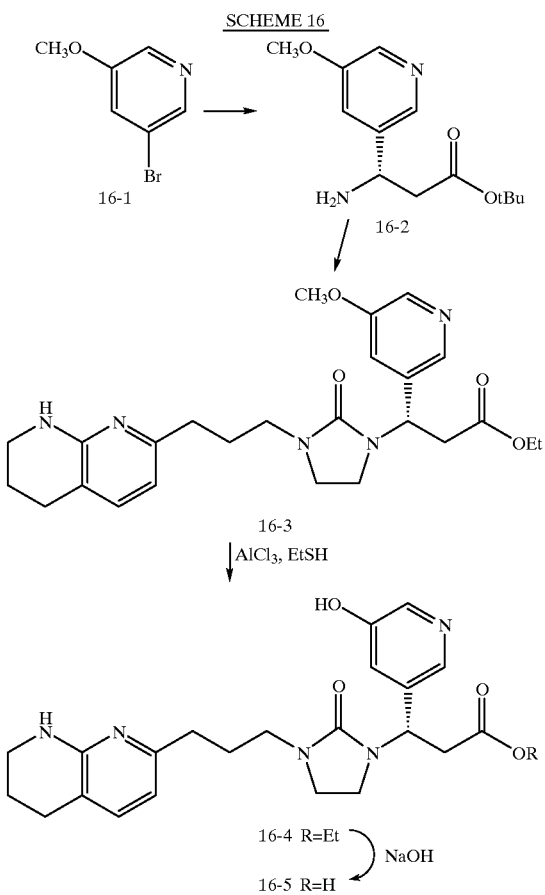

3(S)-Amino-3-(5-methoxy-pyridin-3-yl)-propionic acid tert-butyl ester (16-2)

3-Bromo-5-methoxy-pyridine 16-1 (prepared as described in *J. Org. Chem.* 1990, 55, 69) was converted into 16-2 utilizing the procedure previously described for the conversion of 1-4 to 1-6.
$^1$H NMR (300 MHz, CD$_3$OD) δ 8.20 (d, 1H, J=3 Hz), 8.18 (d, 1H, J=2 Hz),7.50 (s, 1H,), 4.51 (m,1H,), 3.90 (s, 3H), 2.87 (m, 2H, ), 1.37 (m, 9H).

3(S)-(5-Methoxy-pyridin-3-yl)-3-{2-oxo-3-[3-(5,6,7,8-tetrahydro-[1,8]naphthyridin-2-yl)-propyl]-imidazolidin-1-yl}-propionic acid ethyl ester (16-3)

The title compound 16-3 was prepared from 2-9A and 16-2 using the procedure described in Scheme 2.
TLC R$_f$=0.27 (silica, 70:20:10 chloroform/ethyl acetate/MeOH)
$^1$H NMR (300 MHz, CDCl$_3$) δ 8.23 (d, 1H, J=3 Hz), 8.15 (s, 1H), 7.22 (s,1H), 7.02 (d, 1H, J=7 Hz), 6.33 (d, 1H, 7 Hz), 5.46 (t, 1H, J=8 Hz), 4.78 (s, 1H), 4.11 (m, 2H), 3.84 (s, 3H), 3.30 (m, 6H), 3.00 (m, 2H), 2.67 (t, 2H, J=6 Hz), 2.52 (m, 2H), 1.85 (m, 6H),1.23 (m, 3H).

3(S)-(5-Hydroxy-pyridin-3-yl)-3-{2-oxo-3-[3-(5,6,7,8-tetrahydro-[1,8]naphthyridin-2-yl)-propyl]-imidazolidin-1-yl}-propionic acid ethyl ester (16-4)

To a stirred solution of 16-3 (200 mg, 0.4278 mmol) and ethanethiol (0.5 ml) and CH$_2$Cl$_2$ (3 ml) was added AlCl$_3$ (570 mg, 4.28 mmol). After 1.0 hour, the reaction was quenched with sat. NaHCO$_3$. Ethyl acetate was added, and the reaction mixture was then purged with argon for 1.0 hour. The organic layer was separated, washed with brine, dried (MgSO$_4$) and then concentrated to give the phenol 16-4 as a yellow oil.
TLC R$_f$=0.22 (silica, 70:20:10 chloroform/ethyl acetate/MeOH)

3(S)-(5-Hydroxy-pyridin-3-yl)-3-{2-oxo-3-[3-(5,6,7,8-tetrahydro-[1,8]naphthyridin-2-yl)-propyl]-imidazolidin-1-yl}-propionic acid (16-5)

The title compound 16-5 was prepared from 16-4 by basic hydrolysis using the procedure described in Scheme 2.
TLC Rf=0.39 (silica, 10:1:1 EtOH/water/NH$_4$OH).
$^1$H NMR (300 MHz, CD3OD) δ 8.01 (m, 2H), 7.46 (d, 1H, J=7 Hz), 7.20 (s, 1H), 6.53 (d, J=8 Hz, 1H,), 5.49 (m, 1H), 3.51–3.68 (m, 2H), 3.46 (t, 2H, 5 Hz), 3.19 (m, 2H), 3.00 (m, 2H), 2.52–2.78 (m, 6H), 1.92 (m,4H).

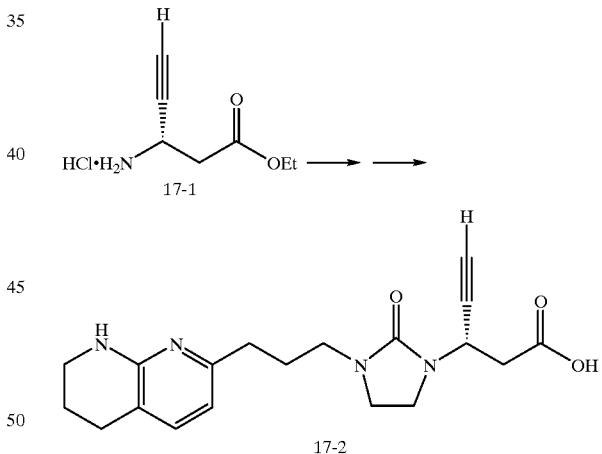

3(S)-(Ethynyl)-3-{2-oxo-3-[3-(5,6,7,8-tetrahydro-[1,8]naphthyridin-2-yl)-propyl]-imidazolidin-1-yl}-propionic acid (17-2)

The title compound 17-2 was prepared from 2-9A and 17-1 (for preparation see J. A. Zablocki, et.al., *J. Med. Chem.* 1995, 38, 2378–2394) using the procedure described in Scheme 2.
TLC Rf=0.32 (silica, 15:10:1:1 ethyl acetate/EtOH/water/NH$_4$OH).
$^1$H NMR (300 MHz, CD$_3$OD) δ 7.45 (d, J=7 Hz, 1H), 6.53 (d, J=8 Hz, 1H), 5.15 (m, 1H), 3.31–3.70 (m, 7H), 2.55–2.85 (m, 7H), 2.35 (m, 1H), 1.88–2.15 (m, 4H).

SCHEME 18

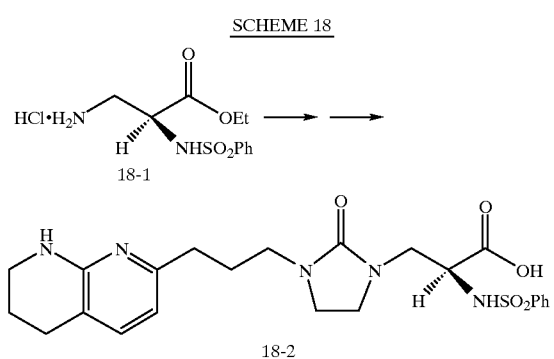

2(S)-Benzenesulfonylamino-3-{2-oxo-3-[3-(5,6,7,8-tetrahydro-[1,8]naphthyridin-2-yl)-propyl]-imidazolidin-1-yl}-propionic acid (18-2)

The title compound 18-2 was prepared from 2-9A and 18-1 (for preparation, see Scheme A substituting phenylsulfonyl chloride for 4-iodophenylsulfonyl chloride) using the procedure described in Scheme 2.
TLC Rf=0.23 (silica,15:10:1:1 ethyl acetate/EtOH/water/NH$_4$OH).
$^1$H NMR (300 MHz, CD$_3$OD) δ 7.81 (m, 2H,), 7.36 (m, 3H), 7.10 (d, 1H, J=8 Hz), 6.37 (d, 1H, J=7 Hz), 3.61 (m, 1H,), 3.36 (m, 2H), 3.02 Æ3.18 (m, 6H), 3.00 (m, 2H), 2.68 (t, 2H, J=6 Hz), 2.50 (m, 2H), 1.79 Æ1.90 (m, 4H).

Scheme 19

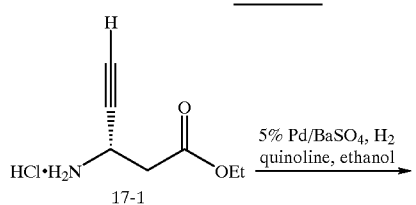

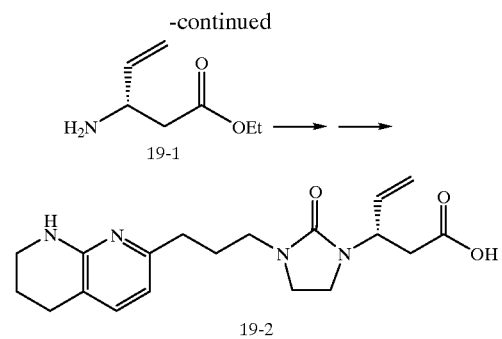

3-Amino-pent-4-enoic acid ethyl ester (19-1)

A mixture of 5% Pd/BaSO$_4$ (0.025 g) and quinoline (0.30 mL) was stirred under a ballon of hydrogen for 30 minutes. 3-Amino-pent-4-ynoic acid ethyl ester 17-1 (1.77 g, 10.0 mmol) in EtOH (15 mL) was added and the solution stirred for an additional 2.5 hours. The solution was filtered through a pad of celite and concentrated in vacuo to provide 2.65 g of crude product 19-1.
$^1$H NMR (CDCl$_3$, 300 MHz): δ 8.40–7.60 (br s, 2H), 6.11–5.96 (m, 1H), 5.58–5.53 (d, 1H), 5.44–5.41 (d, 1H), 4.31–4.16 (m, 3H), 3.12–2.86 (m, 2 H), 1.29–1.25 t, 3H).

3(S)-{2-Oxo-3-[3-(5,6,7,8-tetrahydro-[1,8]naphthyridin-2-yl)-propyl]-imidazolidin-1-yl}-pent-4-enoic acid (19-2)

The title compound 19-2 was prepared from 2-9A and 19-1 using the procedure described in Scheme 2.
$^1$H NMR (CDCl$_3$, 300 MHz): δ 11.1 (s, 1H), 7.21–7.19 (d, 1H), 6.26–6.23 (d, 1H), 5.91–5.78 (m, 1H), 5.22–5.00 (m, 3H), 3.79–3.16 (m, 10H), 2.77–2.33 (m, 5H), 2.06–1.80 (m, 4H).
MS (FAB) 359 (M+1)

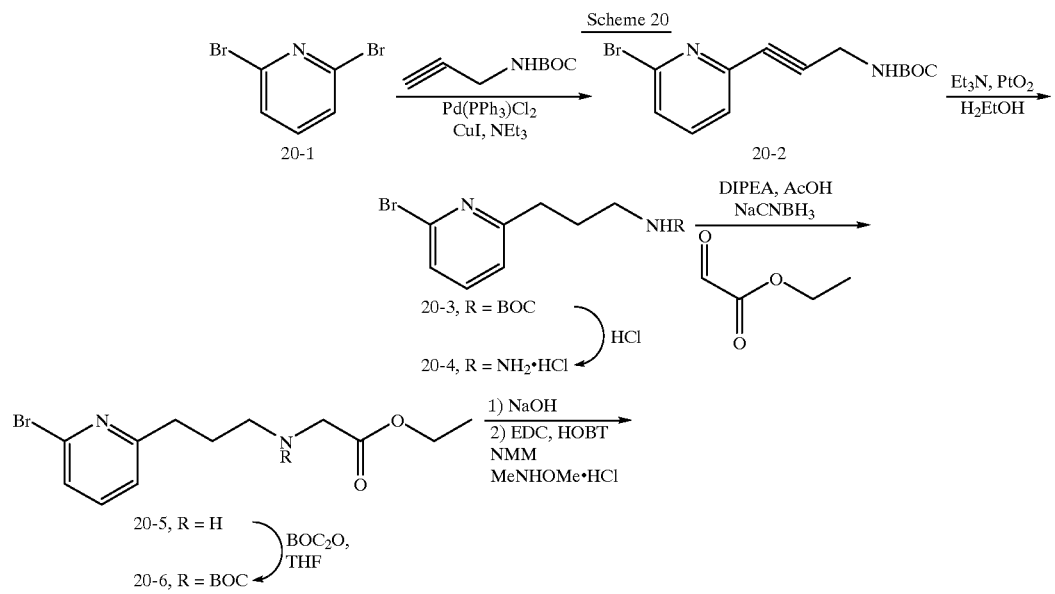

-continued
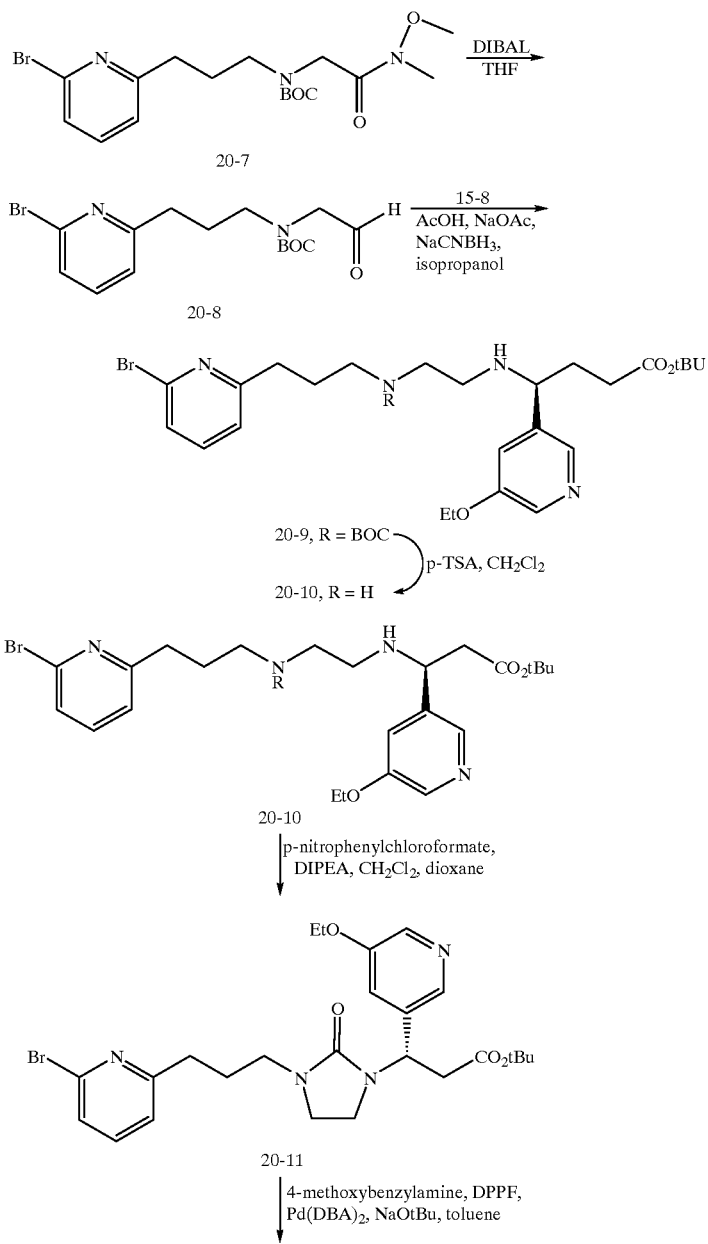

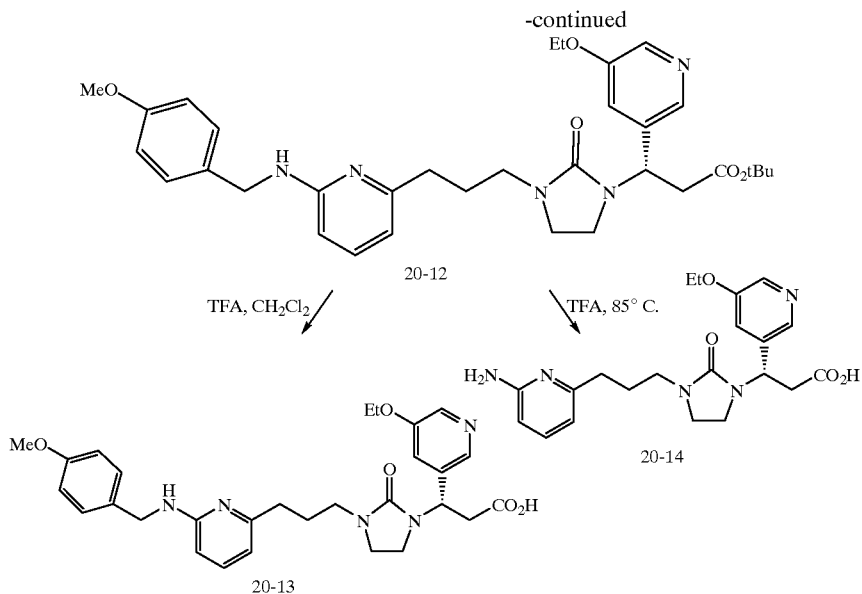

[3-(6-Bromo-pyridin-2-yl)-propyl]-(2-oxo-ethyl)-carbamic acid tert-butyl ester (20-2)

A solution of 2,6-dibromopyridine 20-1 (111 g, 468 mmol) and N-BOC-propargylamine (80.0 g, 515 mmol) in 500 ml of triethylamine at 0° C. was treated with copper(I) iodide (2.23 g, 11.7 mmol). The mixture was purged with argon and then dichlorobis(triphenylphosphine)-palladium (II) 8.22 g, 11.7 mmol) was added. The solution was stirred at 0° C. for one hour, then at room temperature for 16 hours. The solution was diluted with 250 mL ether and washed with $H_2O$ (4×100 mL). The organic extract was washed with brine and dried over $Na_2SO_4$. The solvents were removed in vacuo and the crude product was purified by silica gel chromatography (25% EtOAc/hexane) to afford 20-2.
$^1H$ NMR ($CDCl_3$, 300 MHz): δ 7.53–7.34 (m, 3 H), 4.82–4.80 (br s, 1 H), 4.18–4.17 (d, 2 H), 1.46 s, 9 H).

3-(2-{[3-(6-Bromo-pyridin-2-yl)-propyl]-tert-butoxycarbonyl-amino}-ethylamino) (20-3)

To a solution of 20-2 (79.8 g, 257 mmol) in 350 mL of ethanol and triethylamine (26.8 mL, 193 mmol) was added platinum(IV) oxide (2.91 g, 12.8 mmol). After stirring under a hydrogen atmosphere for 4 hours, the solution was filtered through a pad of celite and concentrated in vacuo. The crude product was dissolved in EtOAc (200 mL) and washed with $H_2O$ (4×250 mL) and brine (250 mL), dried over $Na_2SO_4$, filtered, and concentrated in vacuo. The crude material was purified by silica gel chromatography (10% EtOAc/$CHCl_3$) to afford 20-3.
$^1H$ NMR ($CDCl_3$, 400 MHz): δ 7.48–7.42 (t, 1 H), 7.32–7.29 (d, 1H), 7.13–7.10 (d, 1H), 4.71–4.70 (br s, 1 H), 3.18–3.09 (m, 2 H), 2.82–2.77 (t, 2 H), 1.96–1.85(m, 2 H), 1.44 (s, 9 H).

3-(6-Bromo-pyridin-2-yl)-propylamine.hydrochloride (20-4)

A solution of 20-3 (3.33 g, 10.5 mmol) in EtOAc (150 mL) was saturated with HCl gas and stirred at room temperature for 2 hours. The solvent was removed in vacuo to provide 20-4. The crude product was used in the next step wihout further purification.

[3-(6-Bromo-pyridin-2-yl)-propylamino]-acetic acid ethyl ester (20-5)

A solution of 3-(6-bromo-pyridin-2-yl)propylamine 20-4 (25.6 g, 89.1 mmol), diisopropylethylamine (46.5 mL, 267 mmol), acetic acid (28 mL, 490 mmol), and ethyl glyoxylate (10.9 g, 107 mmol) in 200 ml of methanol was stirred at room temperature for one hour. A 1M solution of $NaCNBH_3$ in THF (98.0 mL, 98.0 mmol) was added slowly with a syringe pump over 4 hours. The resulting solution was stirred for 12 hours, after which the solvent was removed in vacuo and the residue taken up in chloroform and filtered. The solution was then washed with 10% $Na_2CO_3$, dried over $Na_2SO_4$, and the solvent removed in vacuo to give the crude amine. The crude product was purified by silica gel chromatography (7% MeOH/$CHCl_3$) to give 20-5 in a 3:2 mixture of ethyl and methyl esters.
$^1H$ NMR ($CDCl_3$, 300 MHz) δ 7.47–7.42 (t, 1H), 7.31–7.27, (t, 1H), 7.13–7.10 (d, 1H), 4.20–4.14, (m, 2H), 3.39 (s, 2H), 2.85–2.75 (m, 2H), 2.68–2.63 (t, 2H), 1.96–1.88 (m, 2H), 1.29–1.24 (m, 3H).

{[3-(6-Bromo-pyridin-2-yl)-propyl]-tert-butoxycarbonyl-amino}-acetic acid ethyl ester (20-6)

To a solution of [3-(6-bromo-pyridin-2-yl)-propylamino]-acetic acid ethyl ester 20-5 (17.6 g, 58.6 mmol) in THF (200 mL) was added di-tertbutyldicarbonate (15.3 g, 70.3 mmol). After stirring at room temperature for 16 hours, the solvents were removed in vacuo. The product was purified by silica gel chromatography (5% MeOH/$CHCl_3$) to give 20-6.
$^1H$ NMR ($CDCl_3$, 300 MHz) δ 7.47–7.42 (m, 1H), 7.32–7.28 (t, 1H), 7.16–7.10 (t, 1H), 4.22–4.15, (q, 2H), 3.95–3.85 (d, 2H), 3.38–3.29 (m, 2H), 2.80–2.75 (t, 2H), 2.03–1.91 (m, 2H), 1.46–1.44 (m, 9H), 1.31–1.23 (m, 3H).

[3-(6-Bromo-pyridin-2-yl)-propyl]-[(methoxy-methyl-carbamoyl)-methyl]-carbamic acid tert-butyl ester (20-7)

To a solution of 20-6 (23.4 g, 58.4 mmol) in ethanol (200 mL) was added NaOH (100 mL 1M solution in water, 100 mmol). After stirring for 1 h at 50° C., HCl (10.3 mL 12 M, 4.75 mmol) was added in 50 mL EtOH, and the mixture evaporated to give an oily residue. The residue was evaporated from ethanol three times, and then from acetonitrile three times, producing a yellow crusty solid which was dried under a vacuum of <2 mm Hg for 2 h. This residue was then slurried in acetonitrile (180 mL) and chloroform (180 mL), and NMM (41.7 mL, 379 mmol), N,O-dimethylhydroxylamine hydrochloride (11.9 g, 122 mmol), HOBT (10.2 g, 75.9 mmol), and EDC (14.5 g, 75.9 mmol) were added. After stirring for 15 h, the mixture was evaporated to dryness, the residue slurried in EtOAc, washed with sat. $NaHCO_3$, brine, and dried over $Na_2SO_4$. Evaporative removal of the solvent followed by evaporation from toluene to remove the residual NMM gave 20-7 as a yellow oil.
TLC $R_f$=0.49 (silica, 70:25:5 chloroform/ethyl acetate/methanol)
$^1$H NMR ($CDCl_3$, 300 MHz) δ 7.48–7.41 (m, 1H), 7.32–7.28 (t, 1H), 7.17–7.11 (t, 1H), 4.14 (s, 2H), 3.73–3.70 (d, 3H), 3.39–3.30 (m, 2H), 3.18 (s, 3H), 2.80–2.75 (t, 2H), 2.02–1.91 (m, 2H), 1.45 (m, 9H).

[3-(6-Bromo-pyridin-2-yl)-propyl]-(2-oxo-ethyl)-carbamic acid tert-butyl ester (20-8)

To a stirred solution of 20-7 (14.9 g, 35.7 mmol) and THF (100 ml) at −78° C. was added DIBAL (1.0M/hexanes, 53.6 ml, 53.6 mmol) dropwise over 20 minutes. After 1 h, the mixture was warmed to RT and quenched by the careful addition of 20 mL MeOH. 200 ml of 1.0 M Rochelle's salt was then added followed by the removal of the cooling bath. The mixture was stirred for 1.0 hour and then diluted with $Et_2O$. After another 30 minutes of stirring, the organic portion was separated and dried over $MgSO_4$. Evaporative removal of the solvent gave the crude aldehyde 20-8 as a colorless oil.
$^1$H NMR ($CDCl_3$, 300 MHz) δ 9.59–9.56 (d, 1H), 7.48–7.43 (t, 1H), 7.32–7.26 (m, 1H), 7.14–7.07 (m, 1H), 3.53–3.26 (m, 4H), 2.80–2.72 (m, 2H), 2.00–1.93 (m, 2H), 1.44 (s, 9H).

3-(5-Ethoxy-pyridin-3-yl)-propionic acid tert-butyl ester (20-9)

A mixture of the crude aldehyde 20-8 (0.671 g, 1.88 mmol), amine 15-8 (0.651 g, 2.44 mmol), acetic acid (0.107 mL, 1.88 mmol), NaOAc (1.54 g, 18.8 mmol), and powdered molecular sieves (1.20 g) in 2-propanol (15 mL) was stirred for 20 minutes. The mixture was cooled to 0° C. and then $NaBH_3CN$ (0.354 g, 5.64 mmol) was added. After stirring 6 hours, the pH of the mixture was adjusted to ~2 with 1N HCl. The solution was stirred for an additional 10 minutes, ethyl acetate (20 mL) was added, and the pH was adjusted to ~11 with 10% potassium carbonate. The organics were extracted with ethyl acetate, dried over $Na_2SO_4$, and removed in vacuo. The residue was chromatographed (silica gel, [70:25:5 $CHCl_3$/EtOAc/MeOH]) to give 20-9 as a yellow oil in 95% yield.
$^1$H NMR ($CDCl_3$, 300 MHz): δ 8.19–8.18 (d, 1H), 8.14–8.13 (d, 1H), 7.48–7.42 (t, 1H), 7.32–7.26 (m, 1H), 7.23–7.20 (m, 1H), 7.11–7.08 (m, 1H), 4.16–4.02 (m, 3H), 3.30–3.18 (m, 4H), 2.74–2.45 (m, 7H), 1.92–1.86 (t, 2H), 1.45–1.38 (m, 21H).

3-{2-[3-(6-Bromo-pyridin-2-yl)-propylamino]-ethylamino}-3(S)-(5-ethoxy-pyridin-3-yl)-propionic acid tert-butyl ester (20-10)

To a solution of 3-(5-ethoxy-pyridin-3-yl)-propionic acid tert-butyl ester 20-9 (0.085 g, 0.141 mmol) in dichloromethane (5 mL) was added p-toluenesulfonic acid (0.161 g, 0.847 mmol). The mixture was stirred for 2 hours at room temperature and was then neutralized with 1N NaOH. The organic layer was extracted (3×25 mL) with $CHCl_3$, dried, and concentrated in vacuo. The crude product 20-10 was not purified (0.069 g, 96% yield).
$^1$H NMR ($CDCl_3$, 300 MHz): δ 8.23–8.21 (m, 2H), 7.45 (s, 1H), 7.40–7.35 (m, 1H), 7.28–7.25 (t, 1H), 7.04–7.01 (d, 1H), 6.28 (br s, 2H) 4.39–4.33 (t, 1H), 4.00–3.92 (q, 2H), 3.40–3.35 (m, 2H), 3.28–3.22 (m, 1H), 3.15–2.90 (m, 4H), 2.79–2.71 (m, 3H), 2.14–2.01 (m, 2H), 1.34–1.26 (m, 12H).

3-{3-[3-(6-Bromo-pyridin-2-yl)-propyl]-2-oxo-imidazolidin-1-yl}-3(S)-(5-ethoxy-pyridin-3-yl)-propionic acid tert-butyl ester (20-11)

To a stirred solution of 20-10 (0.80 g, 1.57 mmol) and diisopropylethylamine (0.823 mL, 4.72 mmol) in dichloromethane (10 mL) at 0° C. was added p-nitrophenyl chloroformate (0.333 g, 1.65 mmol). The solution stirred for 30 minutes and dioxane (10 mL) was added, then refluxed for 4 hours. EtOAc (100 mL) was added and the organics were washed with 10% $K_2CO_3$, dried, and concentrated in vacuo. The residue was chromatographed (silica gel, [70:20:10 $CHCl_3$/EtOAc/MeOH]) to give 20-11.
$^1$H NMR ($CDCl_3$, 400 MHz) δ 8.22–8.18 (dd, 1H), 8.14–8.13 (t, 1H), 7.46–7.37 (m, 1H), 7.31–7.24 (m, 1H), 7.20–7.16 (m, 1H), 7.11–7.09 (d, 1H), 4.09–4.04 (q, 2H), 3.34–3.16 (m, 5H), 2.99–2.87 (m, 2H), 2.77–2.69 (m, 2H), 2.63–2.46 (m, 2H), 1.97–1.88 (m, 2H), 1.44–1.37 (m, 12H).
MS M+1=533.3

3(S)-(5-Ethoxy-pyridin-3-yl)-3-(3-{3-[6-(4-methoxy-benzylamino)-pyridin-2-yl]-propyl}-2-oxo-imidazolidin-1-yl)-propionic acid tert-butyl ester (20-12)

To a stirred solution of 20-11 (0.075 g, 0.142 mmol) in toluene (3 mL) was added $Pd(DBA)_2$ (0.0041 g, 0.0071 mmol), DPPF (0.0039 g, 0.0071 mmol), and NaOt-Bu (0.0163 g, 0.170 mmol) followed by p-methoxybenzylamine (0.0204 mL, 0.156 mmol). The resulting solution was heated at 110° C. for 2 hours. The solution was cooled and the solvent was removed in vacuo. The product was purified by silica gel chromatography (10% EtOH/EtOAc) to give (20-12).
$^1$H NMR ($CDCl_3$, 400 MHz) δ 8.21–8.20 (d, 1H), 8.14–8.13 (d, 1H), 7.33–7.25 (m, 3H), 7.19–7.17 (t, 1H), 6.87–6.84 (d, 2H), 6.45–6.43 (d, 1H), 6.21–6.18 (d, 1H), 5.48–5.42 (t, 1H), 5.26 (br s, 1H), 4.38–4.37 (d, 2H), 4.09–4.01 (q, 2H), 3.79 (s, 3H), 3.31–3.18 (m, 5H), 3.07–2.87 (m, 3H), 2.63–2.58 (t, 2H), 1.95–1.84 (m, 2H), 1.49–1.39 (m, 12H).

3(S)-(5-Ethoxy-pyridin-3-yl)-3-(3-{3-[6-(4-methoxy-benzylamino)-pyridin-2-yl]-propyl}-2-oxo-imidazolidin-1-yl)-propionic acid (20-13)

To a stirred solution of 20-12 (0.028 g, 0.047 mmol) in dichloromethane (10 mL) was added TFA (1 mL). After 1 hour, the solvent was removed in vacuo and azeotroped twice with toluene (15 mL). The residue was chromatographed (silica gel, 25:10:1:1 followed by 15:10:1:1 ethyl acetate/EtOH/water/$NH_4OH$) to give 20-13 as a white solid.
$^1$H NMR ($CDCl_3$, 400 MHz): δ 8.21–8.20 (d, 2H), 7.50–7.46 (t, 1H), 7.31–7.26 (m, 2H), 7.19 ( s, 1H), 6.88–6.85 (d, 2H), 6.42–6.40 (d, 1H), 6.34–6.32 (d, 1H), 5.69–5.63 (m, 1H), 5.30 (s, 1H), 4.43–4.41 (d, 2H), 4.09–4.01 (q, 2H), 3.77 (s, 3H), 3.75–3.44 (m, 3H), 3.24–2.86 (m, 4H), 2.79–2.67 (m, 3H), 2.03–1.90 (m, 2H), 1.44–1.41 (t, 3H).

MS (FAB) 534 (M+1)

3-{3-[3-(6-Amino-pyridin-2-yl)-propyl]-2-oxo-imidazolidin-1-yl}-3(S)-(5-ethoxy-pyridin-3-yl)-propionic acid (20-14)

To a stirred solution of 20-13 (0.031 g, 0.052 mmol) in dichloromethane (10 mL) was added TFA (1 mL). The solution was stirred for 16 hours at 85° C. after which the solvent was removed in vacuo and azeotroped twice with toluene (15 mL). The residue was chromatographed (silica gel, 15:10:1:1 followed by 10:10:1:1 ethyl acetate/EtOH/water/NH₄OH) to give 20-14 as a white solid.

$^1$H NMR (CD$_3$OD, 400 MHz): δ 8.13–8.10 (m, 2H), 7.59–7.54 (t, 1H), 7.38–7.35 (m, 1H), 6.60–6.57 (d, 2H), 5.53–5.47 (q, 1H), 4.15–4.09 (q, 2H), 3.64–3.57 (m, 1H), 3.47–3.41 (m, 1H), 3.28–3.21 (m, 2H), 3.07–2.90 (m, 3H), 2.76–2.61 (m, 3H), 2.02–1.83 (m, 2H), 1.42–1.38 (t, 3H).

MS (FAB) 414 (M+1)

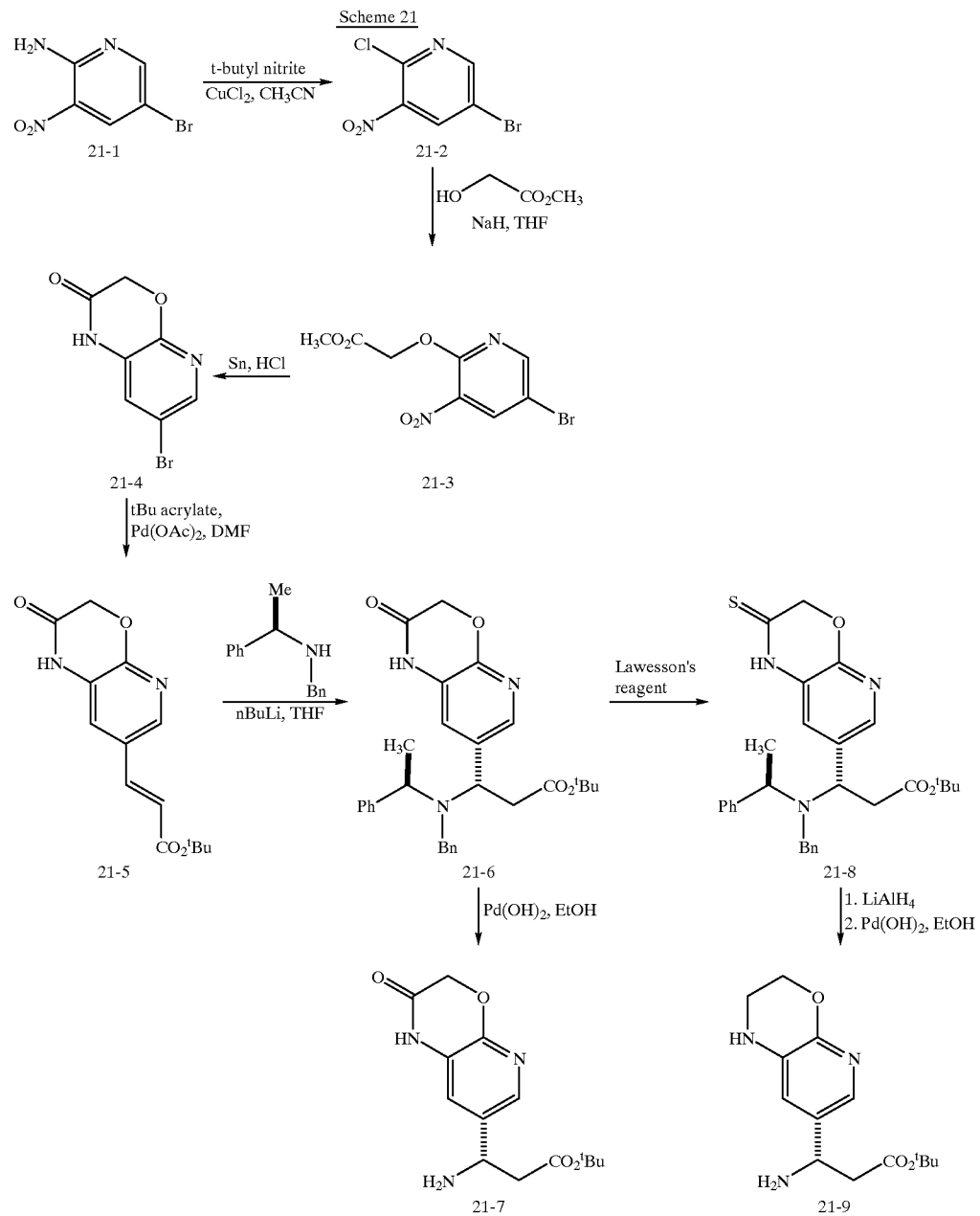

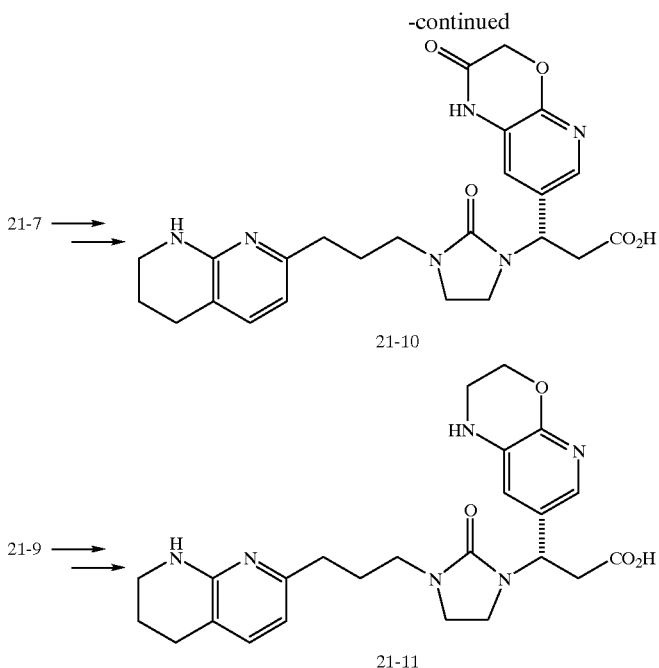

3-Bromo-6-chloro-5-nitropyridine (21-2)

A suspension of $CuCl_2$ (3.33 g, 24.8 mmol) in anhydrous $CH_3CN$ (200 mL) at 65° was treated with tert-butylnitrite (3.13 mL, 26.3 mmol), followed by the dropwise addition of a solution of 21-1 in 60 ml of $CH_3CN$. The resulting mixture was stirred under an argon atomsphere at 65° for 2 h and concentrated at reduced pressure. The residue was partitioned between EtOAc (150 mL) and 3% HCl (60 ml), and the organic layer washed successively with 3% HCl, water, and brine (60 mL), then dried, filtered and concentrated to afford a brown solid which was chromatographed on silica (25% EtOAc/Hexane) to afford 21-2 as a yellow crystaline solid.
TLC Rf=0.60 (25% EtOAc/Hexane)
$^1$H NMR (300 MHz, $CDCl_3$) δ 8.70 (d, J=2.4 Hz, 1H), 8.37 (d, J=2.4 Hz, 1H).

(3-Nitro-5-bromo-pyridin-2-yloxy)-acetic acid methyl ester (21-3)

Methyl glycolate (450 mg, 5.05 mmol) was added to a suspension of 60% NaH (131 mg, 55 mmol) in THF (20 mL) at 0°. The resulting solution was stirred under argon for 0.5 h, then treated with a solution of 21-2. After stirring at 0° for 0.5 h, the reaction was diluted with ethyl acetate, and washed with successively with sat. $NaHCO_3$, water and brine (80 mL each), then dried, filtered and concentrated to afford 21-3 as a yellow solid.
TLC Rf=0.70 (25% EtOAc/Hexane)
$^1$H NMR (300 MHz, $CDCl_3$) δ 8.46 (d, J=2.4 Hz, 1H), 8.37 (d, J=2.4 Hz, 1H) 5.15 (s, 2H), 3.78 (s, 3H).

2-Oxo-2,3-dihydro-1H-4-oxa-1,5-diaza-7-bromo-naphthalene (21-4)

A mixture of 21-3 (1.5 g, 5.12 mmol) and powdered tin (1.37 g, 11.5 mmol) was treated with conc. HCl (10 mL). The mixture was heated to 80° for 2 h, then cooled and concentrated. The residue was partitioned betwen $CHCl_3$ and sat. $NaHCO_3$, washed with brine, then dried, filtered and concentrated to afford a yellow solid.

Chromatography on silica gel (50% hexane/EtOAc) gave 21-4 as a yellow solid.
TLC Rf=0.65 (50% EtOAc/Hexane)
$^1$H NMR (300 MHz, DMSO-$d_6$) δ 10.81 (br,s, 1H), 7.88 (d, J=2.4 Hz, 1H), 7.25 (d, J=2.4 Hz, 1H), 4.81 (s, 2H).

3-(2-Oxo-2,3-dihydro-1H-4-oxa-1,5-diaza-naphthalen-7-yl)-acrylic acid tert-butyl ester (21-5).

A mixture of 21-4 (1.12 g, 4.89 mmol), (o-tol)$_3$P (298 mg, 1.0 mmol), Pd(OAc)$_2$ (110 mg, 0.49 mmol), and triethylamine (0.86 mL, 5.87 mmol) in DMF (20 mL) was placed in a 100-mL flask. The mixture was degassed with argon, then tert-butyl acrylate (752 mg, 5.87 mmol) was added and the tube sealed and heated to 100° for 12 h. The reaction mixture was diluted with ethyl acetate, filtered and washed with $NaHCO_3$, water, and brine, dried, filtered and concentrated.
Chromatography on silica gel (25% hex/EtOAc) gave 21-5 as a yellow solid.
TLC Rf=0.60 (25% EtOAc/Hexane)
$^1$H NMR (300 MHz, DMSO-$d_6$) δ 10.91 (br,s, 1H), 8.15 (d, J=2.4 Hz, 1H), 7.54 (d, J=16 Hz, 1 H), 7.42 (d, J=2.4 Hz, 1H), 6.35 (d, J=16 Hz, 1 H), 4.84 (s, 2H), 1.48 (s, 9H).

3(S)-[Benzyl-(1(R)-phenylethyl)-amino]-3-(2-oxo-,2,3-dihydro-1H-4-oxa-1,5-diaza-naphthalen-7-yl)-propionic acid tert-butyl ester (21-6)

A solution of N-benzyl-α-(R)-methylbenzylamine (0.82 g,3.87 mmol) in THF (25 mL) at 0° C. was treated with n-BuLi (1.6 mL of a 2.5 M soln in hexanes). The resulting solution was stirred at 0° C. for 30 min and then cooled to −78° C. A solution of acrylate 21-5 (0.485 g, 1.76 mmol) in THF (5 mL) was added. After stirring for 15 min at −78° C., satd aq $NH_4Cl$ soln (5 mL) was added and the cold bath removed. The mixture was warmed to room temperature, and extracted with $Et_2O$ (2×40 mL). The combined organic extracts were washed with brine (30 mL), dried over $MgSO_4$, filtered, and concentrated. The residue was purified by flash chromatography (40% ethyl acetate/hexanes) to give the β-aminoester 21-6 as a yellow oil.

TLC Rf=0.3 (40% ethyl acetate/hexanes)
¹H NMR (300 MHz, CDCl₃) δ 1H NMR 8.70 (br, s, 1H), 7.91 (d, J=1.8 Hz, 1H),7.4–7.2 (10H), 7.12 (d, J=1.8 Hz, 1H), 4.80 (s, 2 H), 4.42 (m, 1H), 3.91 (q, J=6.7 Hz, 1 H), 3.69 (d, J=7.2 Hz, 1H, ), 3.62 (d, J=7.2 Hz, 1H,), 2.46 (m, 2H), 1.34 (d, J=7.0 Hz, 3H), 1.29 (s, 9H).

3(S)-Amino-3-(2-oxo-2,3-dihydro-1H-4-oxa-1,5-diaza-naphthalen-7-yl)-propionic acid tert-butyl ester (21-7)

A mixture of the dibenzylamine 21-6 (0.22 g, 0.44 mmol) in EtOH/H₂O/AcOH (26 mL/3 mL/1.0 mL) was degassed with argon and treated with Pd(OH)₂ (100 mg). The mixture was placed under 1 atm of H₂. After stirring for 18 h, the mixture was diluted with EtOAc and filtered through celite. The filtrate was concentrated and the residue purified by flash chromatography (20% 20:1:1 EtOH/NH₄OH/H₂O-80% EtOAc) to give the tert-butyl ester 21-7 as a white solid.
TLC R$_f$=0.5 (20% 20:1:1 EtOH/NH₄OH/H₂O-80% EtOAc)
¹H NMR (300 MHz, CD₃OD) δ 7.89 (d, J=1.7 Hz, 1H), 7.31 (d, J=1.7 Hz, 1H), 4.81 (s, 2H), 4.38 (m, 1H), 2.6, (m, 2H), 1.41 (s, 9H).

3(R)-[Benzyl-(1-phenylethyl)-amino]-3(S)-(2-thioxo-2,3-dihydro-1H-4-oxa-1,5-diaza-naphthalen-7-yl)-propionic acid tert. butyl ester (21-8)

A solution of 21-6 (0.22 g, 0.44 mmol ) in anhydrous THF was treated with Lawesson's reagent (0.098 g, 0.243 mmol) and stirred at room temperature for 1.5 h. Silica gel (500 mg) was added to the reaction mixture and the solvent was removed at reduced pressure and the product was eluted from silica using 25% EtOAc/hexane to afford 21-8 as a yellow solid.
TLC R$_f$=0.7 (40% EtOAc/hexane)
¹H NMR (300 MHz, CD₃OD) δ 9.82 (br, s, 1H), 7.95 (d, J=1.8 Hz, 1H),7.4–7.2 (11H), 5.08 (s, 2 H), 4.42 (m, 1H), 3.91 (q, J=6.7 Hz, 1 H), 3.69(d, J=7.2 Hz, 1H,), 3.62 (d, J=7.2 Hz, 1H), 2.46 (m, 2H), 1.34 (d, J=7.0 Hz, 3H), 1.29 (s, 9H).

3(S)-Amino-3-(2,3-dihydro-1H-4-oxa-1,5-diaza-naphthalen-7-yl)-propionic acid tert-butyl ester (21-9)

A solution of 21-8 (1.0 g, 1.9 mmol) in anhydrous Et₂O (10 mL) at 0° was treated dropwise with LiAlH₄ (2.09 ml of a 1.0 M solution in Et₂O). The resulting solution was stirred at 0° C. for 30 min and then quenched by the sequential addition of H₂O (0.3 mL), 15% NaOH (0.08 mL). Celite (1 g) was added and the mixture filtered through a Celite pad. The filtrate was evaporated and the residue was purified by flash chromatography (65% ethyl acetate/hexanes) to give the dibenzylamine intermediate as a yellow oil.
TLC Rf=0.4 (65% ethyl acetate/hexanes)
¹H NMR (300 MHz, CDCl₃) δ 1H NMR 7.61 (d, J=1.8 Hz, 1H),7.4–7.2 (10H), 6.87 (d, J=1.8 Hz, 1H), 4.41 (m, 2 H), 4.36 (m, 1H), 3.91 (q, J=6.7 Hz, 1 H), 3.8 (brs, 1H), 3.69 (m, 2H), 3.42 (m, 2H), 2.46 (m, 2H), 1.34 (d, J=7.0 Hz, 3H), 1.29 (s, 9H).
This material was deprotected with Pd(OH)₂ in ethanol to afford 21-9 as a white solid. TLC R$_f$=0.5 (20% 20:1:1 EtOH/NH₄OH/H₂O-80% EtOAc)
¹H NMR (300 MHz, CD₃OD) δ 7.59 (d, J=1.7 Hz, 1H), 6.92 (d, J=1.7 Hz, 1H), 4.41 (m, 2H), 4.30 (m, 1H), ), 3.41 (m, 2H), 2.6, (m, 2H), 1.41 (s, 9H).

3(S)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid (21-10)

The title compound 21-10 was prepared from 2-9A and 21-7 using the procedure described in Scheme 2.
High resolution MS Calc'd.=418.2198, Obs'd=481.2193.

3(S)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid (21-11)

The title compound 21-11 was prepared from 2-9A and 21-8 using the procedure described in Scheme 2.
High resolution MS Calc'd.=467.2417, Obs'd=467.2401.

Scheme 22

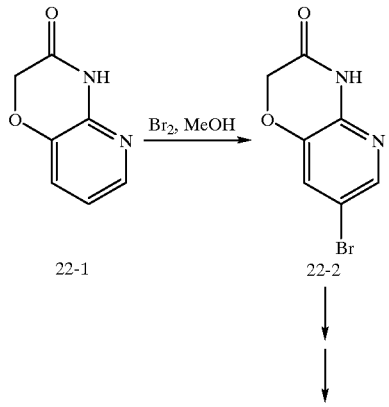

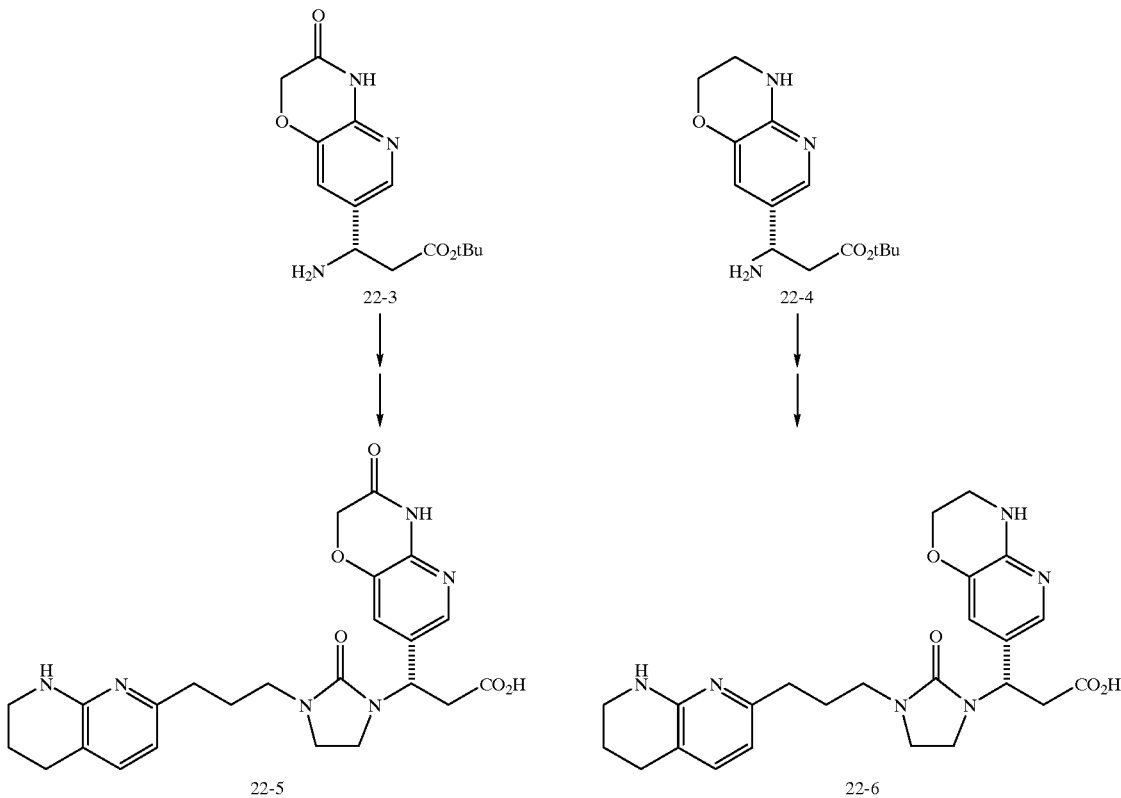

3-Oxo-3,4-dihydro-2H-1-oxa-4,5-diaza-7-bromo-naphthalene (22-2)

A solution of 22-1 (4.8 g, 32 mmol) in MeOH (160 mL) at −15° was treated dropwise with bromine (25.7 g, 161 mmol). After stirring at −15° for 0.5 h, the mixture was warned to ambient temperature and stirred overnight. The resulting white precipitate was filtered and washed with cold MeOH to afford 22-2 as a white solid.

TLC Rf=0.65 (50% EtOAc/Hexane)
$^1$H NMR (300 MHz,DMSO-$d_6$) δ 11.2 (br s, 1H), 8.05 (d, J=2.4 Hz, 1H), 7.66 (d, J=2.4 Hz, 1H), 4.76 (s, 2H).

3(S)-Amino-3-(3-oxo-3,4-dihydro-2H-1-oxa-4,5-diaza-naphthalen-7-yl)-propionic acid tert-butyl ester (22-3)

Bromide 22-2 was converted to amino ester 22-3 as illustrated in Scheme 21.

TLC $R_f$=0.5 (12% 20:1:1 EtOH/NH$_4$OH/H$_2$O-88% EtOAc)
$^1$H NMR (300 MHz, CD$_3$OD) δ 8.04 (d, J=1.7 Hz, 1H), 7.34 (d, J=1.7 Hz, 1H), 4.76 (s, 2H), 4.38 (m, 1H), 2.6, (m, 2H), 1.41 (s, 9H).

3(S)-Amino-3-(3-oxo-3,4-dihydro-2H-1-oxa-4,5-diaza-naphthalen-7-yl)-propionic acid tert-butyl ester (22-4)

Bromide 22-2 was converted to amino ester 22-4 as illustrated in Scheme 21.

TLC $R_f$=0.5 (20% 20:1:1 EtOH/NH$_4$OH/H$_2$O-80% EtOAc)
$^1$H NMR (300 MHz, CD$_3$OD) δ 8.04 (d, J=1.7 Hz, 1H), 7.34 (d, J=1.7 Hz, 1H), 4.76 (s, 2H), 4.38 (m, 1H), 2.6, (m, 2H), 1.41 (s, 9H).

3(S)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid (22-5)

The title compound 22-5 was prepared from 2-9A and 22-3 using the procedure described in Scheme 2.
High resolution MS Calc'd.=481.2198, Obs'd=481.2194.

3(S)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid (22-6)

The title compound 22-6 was prepared from 2-9A and 22-4 using the procedure described in Scheme 2.
High resolution MS Calc'd.=467.2417, Obs'd=467.2411.

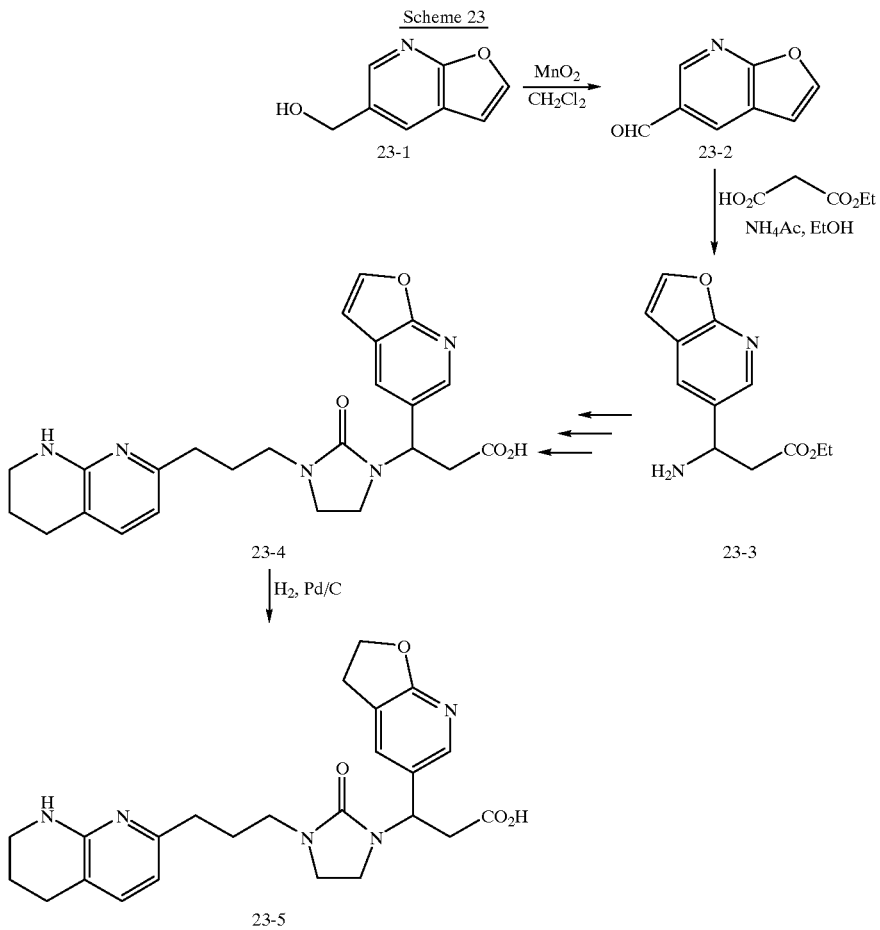

Scheme 23

Furo-[2,3-b]pyridine-5-carboxaldehyde (23-2)

A solution of alcohol 23-1 (M. Bhupathy, et al., *J. Heterocycl. Chem.* 1995, 32, 1283–1287) was treated with excess $MnO_2$ (10 eq) and the mixture stirred at room temperature for 16 h, then filtered through Celite and evaporated to afford 23-2 as a white solid.
TLC Rf=0.40 (25% EtOAc/Hexane)
$^1$H NMR (300 MHz, $CDCl_3$) δ 10.22 (s, 1H), 9.05 (d, J=1.8 Hz, 1H), 8.27 (d, J=1.7 Hz, 1H) 8.08 (d, J=1.8 Hz, 1H), 7.10 (d, J=1.7 Hz, 1H).

3-Amino-3-(furo[2,3-b]pyridin-5-yl)-propionic acid ethyl ester (23-3)

A solution containing aldehyde 23-2 (1.5 g, 10 mmol), ethyl hydrogen malonate (1.6 g, 20 mmol), and ammonium acetate (3.8 g, 50 mmol) in anhydrous ethanol (125 mL) was heated at reflux for 8 h. After cooling to room temperature, the solvent was evaporated and the residue partitioned between sat. sodium bicarbonate and EtOAc, the organic layer removed, dried, and concentrated. Chromatography of the residue afforded the amino ester 23-3 as a waxy solid.
TLC $R_f$=0.5 (20% 20:1:1 EtOH/$NH_4OH$/$H_2O$-80% EtOAc)
$^1$H NMR (300 MHz, $CD_3OD$) δ 8.34 (d, J=1.7 Hz, 1H), 8.04 (d, J=1.7 Hz, 1H), 7.72 ( d, J-1.7 Hz, 1H), 6.78 (d, J=1.7 Hz, 1H), 4.62 (m, 1H), 4.13 (q, J=7.5 Hz, 2H), 3.20 (br, s, 2H), 2.76 (m, 2H), 1.23 (t, J=7.5 Hz, 3H).

3-Furo[2,3-b]pyridin-6-yl-3-{2-oxo-3-[3-(5,6,7,8-tetrahydro-[1,8]naphthyridin-2-yl)propyl] imidazolidin-1-yl}propionic acid (23-4)

The title compound 23-4 was prepared from 2-9A and 23-3 using the procedure described in Scheme 2.
TLC $R_f$=0.30 (50% 20:1:1 EtOH/$NH_4OH$/$H_2O$-50% EtOAc).
FAB MS Obs'd 450.1 (M+H).

3-(2,3-Dihydrofuro[2,3-b]pyridin-6-yl)-3-{2-oxo-3-[3-(5,6,7,8-tetrahydro-[1,8]naphthyridin-2-yl)propyl] imidazolidin-1-yl}propionic acid (23-5)

A solution of 23-4 (360 mg, 0.80 mmol) in MeOH (10 mL) was treated with 10% Pd/C (100 mg) and stirred under a hydrogen atmosphere for 18 h. The catalyst was removed by filtration through celite and the residue chromatographed (75% 20:1:1 EtOH/$NH_4OH$/$H_2O$-25% EtOAc) to afford 23-5 as a colorless glass.
TLC $R_f$=0.30 (50% 20:1:1 EtOH/$NH_4OH$/$H_2O$-50% EtOAc)
FAB MS Obs'd 452.2 (M+H).

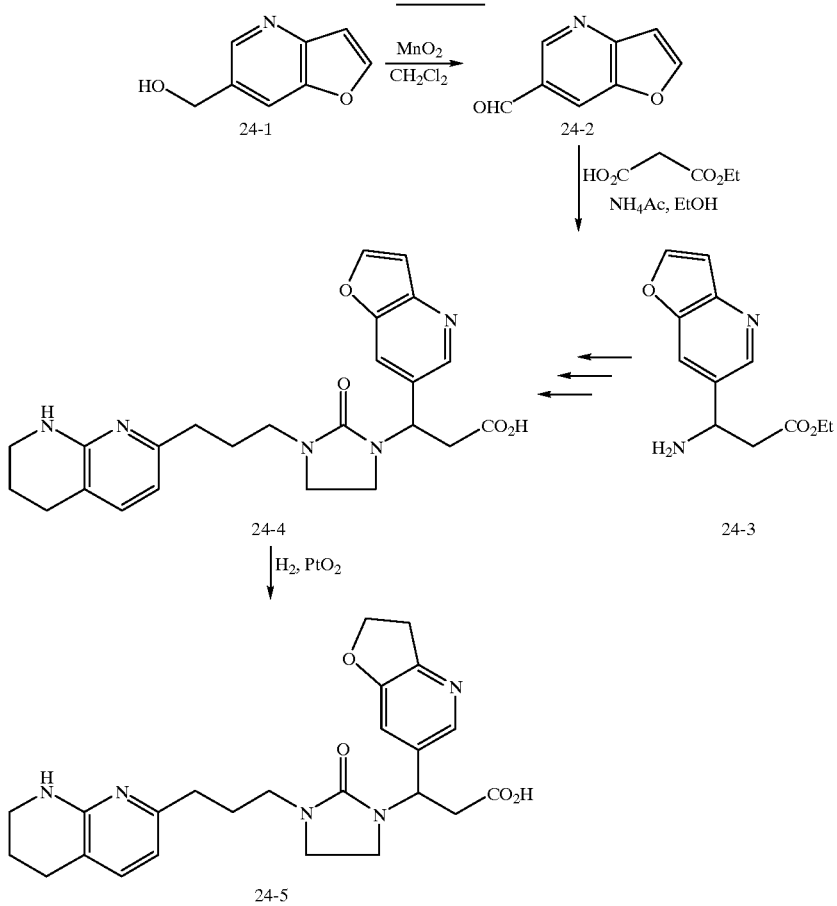

Scheme 24

Furo[3,2-b]pyridine-5-carboxaldehyde (24-2)

A solution of alcohol 24-1 (J. M. Hoffman, Jr., U.S. Pat. No. 4,808,595) was treated with excess $MnO_2$ (10 eq) and the mixture stirred at room temperature for 16 h, then filtered through Celite and evaporated to afford 24-2 as a white solid.

$^1$H NMR (300 MHz, $CDCl_3$) δ 10.18 (s, 1H), 8.92 (d, J=1.8 Hz, 1H), 8.17 (d, J=1.7 Hz, 1H) 7.89 (d, J=1.8 Hz, 1H), 7.10 (d, J=1.7 Hz, 1H).

3-Amino-3-(furo[3,2-b]pyridin-5-yl)-propionic acid ethyl ester (24-3)

A solution containing aldehyde 24-2 (1.5 g, 10 mmol), ethyl hydrogen malonate (1.6 g, 20 mmol), and ammonium acetate (3.8 g, 50 mmol) in anhydrous ethanol (125 mL) was heated at reflux for 8 h. After cooling to room temperature, the solvent was evaporated and the residue partitioned between sat. sodium bicarbonate and EtOAc, the organic layer removed, dried, and concentrated. Chromatography of the residue afforded the amino ester 24-3 as a waxy solid. TLC $R_f$=0.5 (20% 20:1:1 EtOH/$NH_4$OH/$H_2$O-80% EtOAc)
$^1$H NMR (300 MHz, $CD_3$OD) δ 8.58 (d, J=1.7 Hz, 1H), 7.89 (d, J=1.7 Hz, 1H),7.85( d, J-1.7 Hz, 1H), 6.98 (d, J=1.7 Hz, 1H), 4.62 (t, J=7.2 Hz, 1H), 4.09 (q, J=7.5 Hz, 2H), 2.76 (m, 2H), 2.20 (br, s, 2H), 1.21 (t, J=7.5 Hz, 3H).

3-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid (24-4)

The title compound 24-4 was prepared from 2-9A and 24-3 using the procedure described in Scheme 2.

TLC $R_f$=0.56 (75% 20:1:1 EtOH/$NH_4$OH/$H_2$O-25% EtOAc)

High resolution MS Calc'd.=450.2117, Obs'd=450.2136.

3-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid (24-5)

A solution of 24-4 (181 mg, 0.38 mmol) in acetic acid (5 mL) was treated with $PtO_2$ (100 mg) and stirred under a hydrogen atmosphere for 1 h. The catalyst was removed by filtration through celite and the residue chromatographed (75% 20:1:1 EtOH/$NH_4$OH/$H_2$O-25% EtOAc) to afford 24-5 as a colorless glass.

TLC $R_f$=0.50 (75% 20:1:1 EtOH/$NH_4$OH/$H_2$O-25% EtOAc)

High resolution MS Calc'd.=452.2298, Obs'd=452.2238

Scheme 25

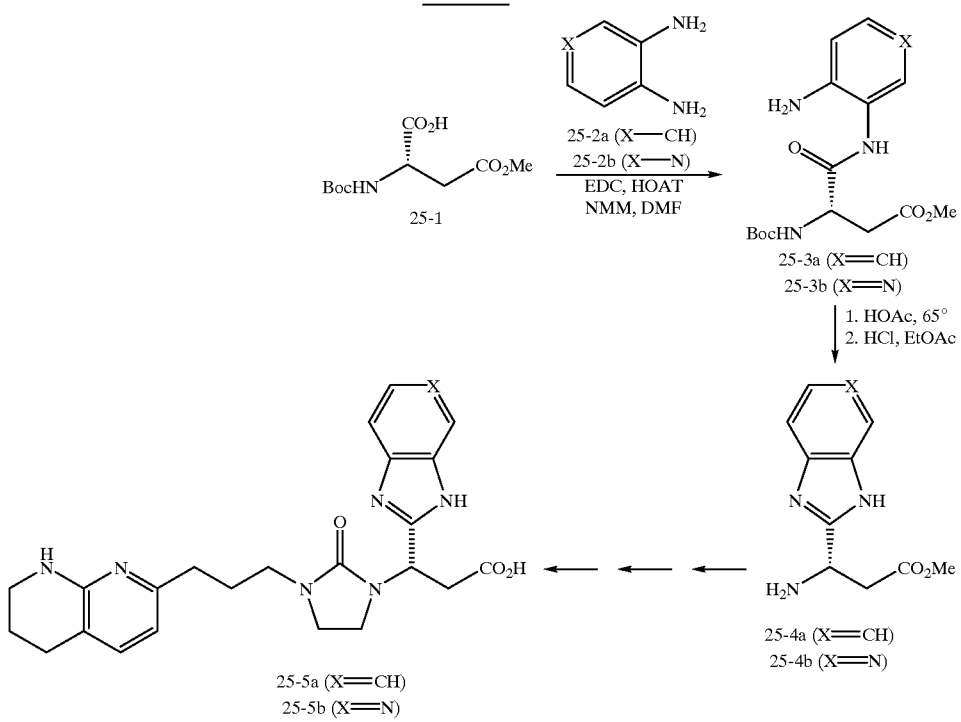

N-(S)-(2-Amino-phenyl)-3-tert-butoxycarbonylamino-succinamic acid methyl ester (25-3a)

A mixture of Boc-L-aspartic acid-β-methyl ester 25-1 (5.0 g, 20.2 mmol), o-phenylenediamine 25-2a (2.2 g, 20.2 mmol), EDC (3.9 g, 20.2 mmol), HOAT (0.28 g, 2.02 mmol), and NMM (6.7 mL, 60.7 mmol) in DMF (50 mL) was stirred for 18 h at ambient temperature. The solution was diluted with EtOAc (250 mL) and washed with sat. sodium bicarbonate, water, and brine (50 mL each), then dried and evaporated to afford 25-3a as a yellow solid.
TLC $R_f$=0.50 (95% CHCl$_3$/5% isopropanol)
$^1$H NMR (300 MHz, CDCl$_3$) δ 8.10 (br,s, 1H), 7.23 (d, J=7.8 Hz, 1H), 7.08 (t, J=7.8 Hz, 1H) 6.78 (m, 1H),5.8 (br d, 1H), 4.65 (m, 1 H), 3.76 (s, 3H), 3.15 (dd, J=4.6, 16 Hz, 1H), 2.90 (dd, J=5.1, 16 Hz, 1H), 1.48 (s, 9H).

3(S)-Amino-3-(benzimidazol-2-yl)-propionic acid methyl ester (25-4a)

Ester 25-3a (1.0 g, 3 mmol) was dissolved in acetic acid (50 mL) and heated to 65° for 2 h. The solvent was removed to afford the Boc-protected intermediate as a white solid. The crude material (920 mg, 2.43 mmol) was dissolved in EtOAc, cooled to 0°, and treated with HCl gas to give 25-4a as a tan solid.

$^1$H NMR (300 MHz, CD$_3$OD) δ 7.80 (m, 2H), 7.35 (m,2H), 5.98 (m, 1H), 3.80 (m, 2H), 3.76 (s, 3H).

3(S)-(Benzimidazol-2-yl)-3-(2-oxo-3-[3-(5,6,7,8-tetrahydro-[1,8]naphthyridin-2-yl)propyl] imidazolidin-1-yl)propionic acid (25-5a)

The title compound 25-5a was prepared from 2-9A and 25-4a using the procedure described in Scheme 2.
TLC $R_f$=0.30 (50% 20:1:1 EtOH/NH$_4$OH/H$_2$O-50% EtOAc).
FAB MS Obs'd 449.2 (M+H).

3(S)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid (25-5b)

The title compound 25-4b was prepared as described above substituting 3,4-diaminopyridine for o-phenylenediamine.
TLC $R_f$=0.25 (50% 20:1:1 EtOH/NH$_4$OH/H$_2$O-50% EtOAc).
FAB MS Obs'd 450.2 (M+H).

Scheme 26

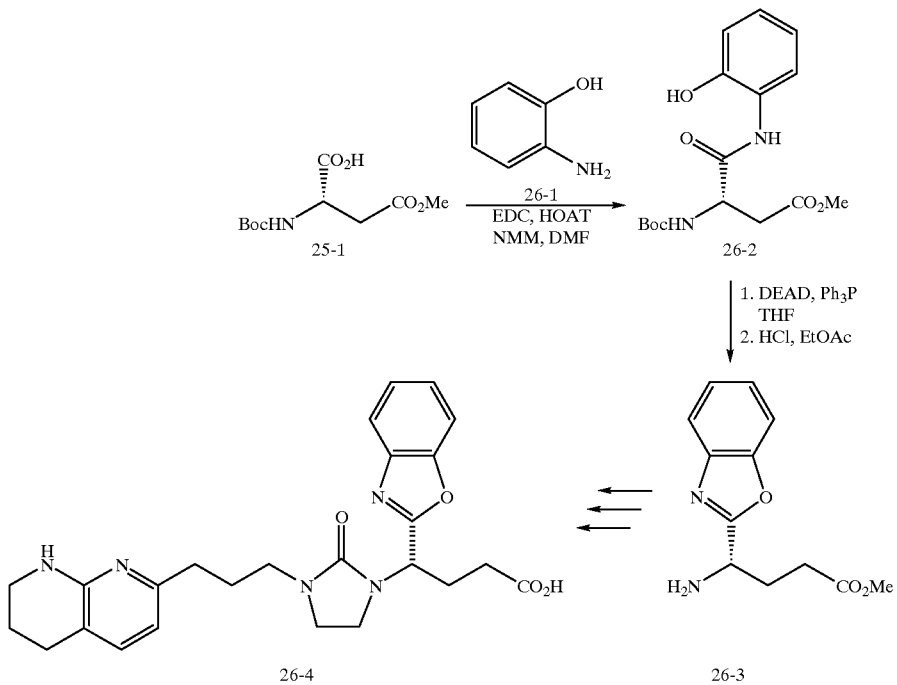

N-(S)-(2-Hydroxy-phenyl)-3-tert-butoxycarbonylamino-succinamic acid methyl ester (26-2)

A mixture of Boc-L-aspartic acid-β-methyl ester (21-1) (5.0 g, 20.2 mmol), 2-amino phenol (26-1) (2.2 g, 20.2 mmol), EDC (3.9 g, 20.2 mmol), HOAT (0.28 g, 2.02 mmol), and NMM (6.7 mL, 60.7 mmol) in DMF (50 mL) was stirred for 18 h at ambient temperature. The solution was diluted with EtOAc (250 mL) and washed with sat. sodium bicarbonate, water, and brine (50 mL each), then dried, and evaporated and chromatographed on silica (EtOAc) to afford 26-2 as a white solid.
TLC $R_f$=0.55 (EtOAc)
$^1$H NMR (300 MHz, CDCl$_3$) δ 7.23 (d, J=7.8 Hz, 1H ), 6.89 (t, J=7.8 Hz, 1H), 6.78 (m, 1H), 5.68 (br d, 1H), 4.65 (m, 1 H), 3.76 (s, 3H), 3.15 (dd, J=4.6, 16 Hz, 1H), 2.90 (dd, J=5.1, 16 Hz, 1H), 1.48 (s, 9H).

3(S)-Amino-(3-benzoxazol-2-yl)-propionic acid methyl ester (26-3)

Ester 26-2 (2.0 g, 6.0 mmol) was dissolved in anhydrous THF (150 mL) along with Ph$_3$P (1.58 g, 6.0 mmol). The resulting solution was cooled to 0°, and a solution of diethyl azodicarboxylate (1.53 g, 6.2 mmol) in THF (25 mL) was added dropwise. The cooling bath was removed and the solution stirred overnight at ambient temperature. The solution was concentrated and the residue chromatographed (75% EtOAc/Hexane) to afford the Boc-protected ester as a colorless glass. The crude material (1.8 g, 5.0 mmol) was dissolved in EtOAc, cooled to 0° and treated with HCl gas to give 26-3 as a tan solid.
$^1$H NMR (300 MHz, CD$_3$OD) δ 7.81 (m, 2H), 7.40 (m,2H), 5.05 (t, J=7.4 Hz, 1H), 3.72 (s, 3H), 3.30 (m, 2H).

3(S)-(Benzoxazol-2-yl)-3-(2-oxo-3-[3-(5,6,7,8-tetrahydro-[1,8]naphthyridin-2-yl)propyl] imidazolidin-1-yl)propionic acid (26-4)

The title compound 26-4 was prepared from 2-9A and 26-3 using the procedure described in Scheme 2.

TLC $R_f$=0.40 (50% 20:1:1 EtOH/NH$_4$OH/H$_2$O-50% EtOAc).
FAB MS Obs'd 450.3 (M+H).

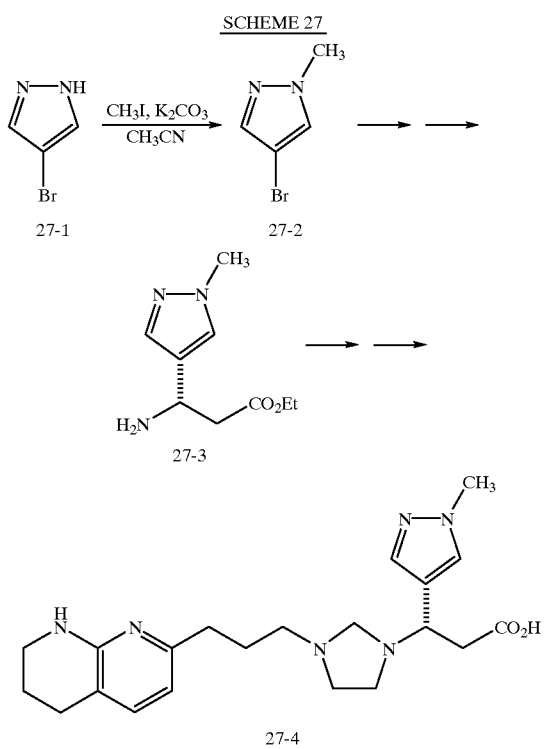

1-Methyl-4-bromopyrazole (27-2)

Methyl iodide (8.47 mL, 136 mmol) was added to a mixture of 4-bromopyrazole 27-1 (10 g, 38 mmol), and K$_2$CO$_3$ (18.9 g, 136 mmol) in CH$_3$CN (150 mL) and the mixture stirred at room temperature for 16 h, then filtered and evaporated to yield 27-2 as a yellow oil.

$^1$H NMR (300 MHz, CDCl$_3$) δ 7.44(s, 1H),7.38 (s, 1H), 3.90 (s, 3H).

3 (S)-Amino-3-(1-methyl-1H-pyrazol-4yl)-propionic acid ethyl ester (27-3)

The bromide 27-2 was converted to the amino ester 27-3 following the procedure depicted in Scheme 1.

$^1$H NMR (300 MHz, CD$_3$OD) δ 7.81 (s, 1H),7.58 (s, 1H),4.80 (m, 1H), 4.05 (q, J=7.0 Hz, 2 H), 3.89 (s, 3H), 3.00 (m, 2 H), 1.24 (t, J=7.0 Hz, 3 H).

3(S)-(1-Methyl-1H-pyrazol-4-yl)-3-(2-oxo-3-[3-(5,6,7,8-tetrahydro-[1,8]naphthyridin-2-yl)propyl]-imidazolidin-1-yl)propionic acid (27-4)

The title compound 27-4 was prepared from 2-9A and 27-3 using the procedure described in Scheme 2.

TLC Rf=0.24 (15:10:1:1 ethyl acetate/EtOH/water/NH$_4$OH).

$^1$H NMR (300 MHz, CD$_3$OD) δ 7.58 (s, 1H), 7.52 (d, J=7.3 Hz, 1H), 7.38 (s, 1H), 6.62 (d, J=7.3 Hz, 1H), 5.38 (m, 1H),3.83 (s, 3H), 3.14–3.53 (9H), 2.97 (m, 2H), 2.80 (t, J=6.1 Hz, 2H), 2.67 (t, J=7.3 Hz, 2H), 1.93 (m,4H).

SCHEME A
SYNTHESIS OF RADIOLIGAND FOR SPA ASSAY

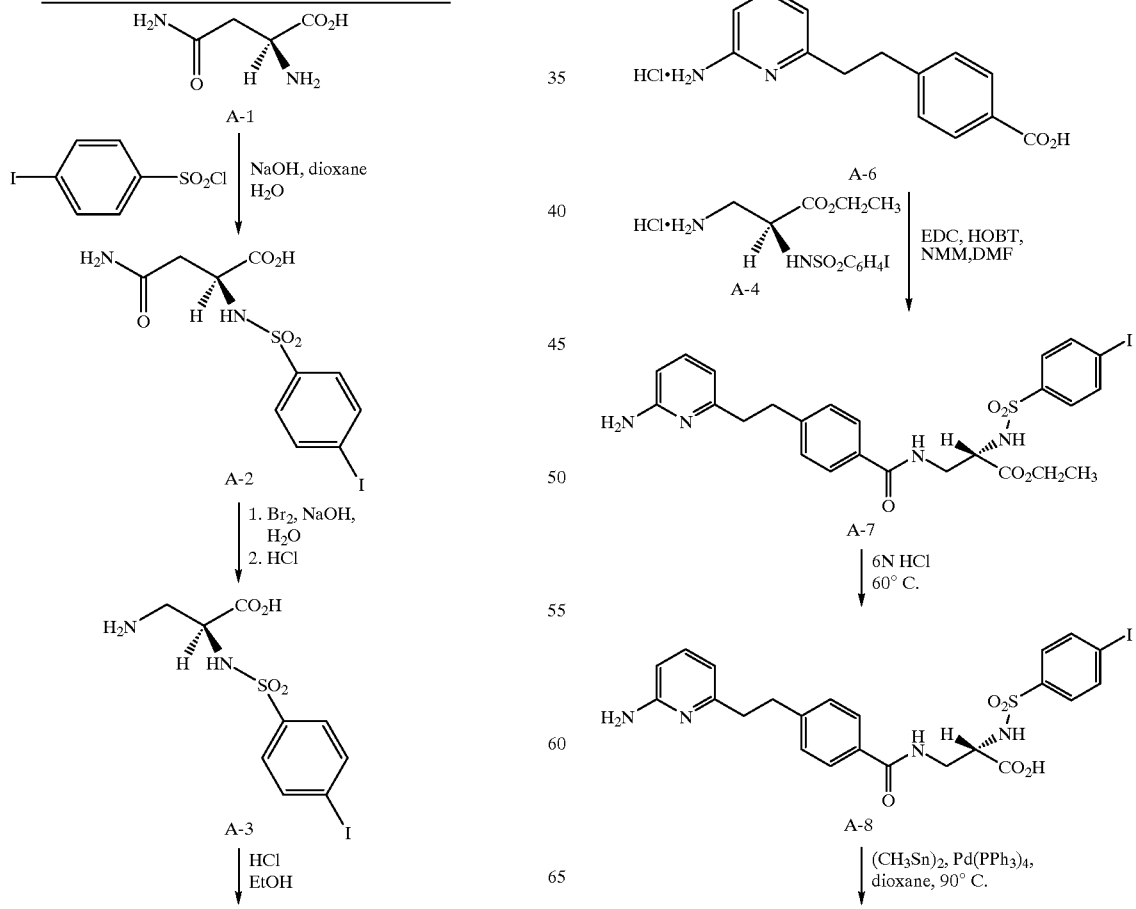

-continued

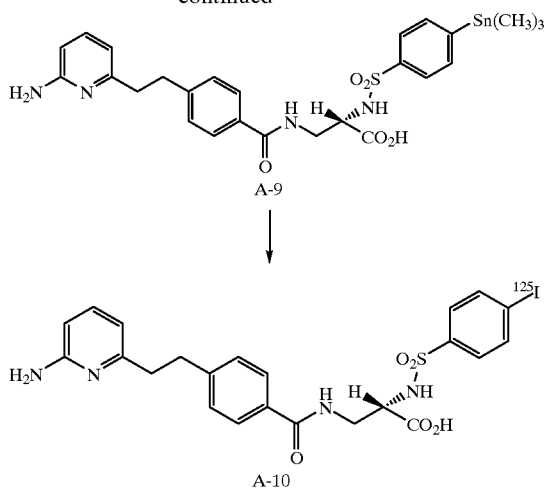

N-(4-Iodo-phenylsulfonylamino)-L-asparagine (A-2)

To a stirred solution of acid A-1 (4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After ~5 minutes, NaOH (1.49, 37.2 mmol), dissolved in 15 ml H$_2$O, was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$_2$O to provide acid A-2 as a white solid.
$^1$H NMR (300 MHz, D$_2$O) δ 7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (A-3)

To a stirred solution of NaOH (7.14 g, 181.8 mmol) and H$_2$O (40 ml) at 0° C. was added Br$_2$ (1.30 ml, 24.9 mmol) dropwise over a ten minute period. After ~5 minutes, acid A-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid A-3 as a white solid.
$^1$H NMR (300 MHz, D$_2$O) δ 8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (A-4)

HCl gas was rapidly bubbled through a suspension of add A-3 (4.0 g, 10.81 mmol) in EtOH (50 ml) at 0° C. for 10 minutes. The cooling bath was removed and the reaction was heated to 60° C. After 18 h, the reaction was concentrated to provide ester A-4 as a white solid.
$^1$H NMR (300 MHz, CD$_3$OD) δ 7.98 (d, 2H, J=8 Hz), 7.63 (d, 2H, J=8 Hz), 4.25 (m, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (A-5a)

A mixture of ester A-5 (700 mg, 2.63 mmol), (for preparation, see: Scheme 29 of PCT International Applica-tion Publication No. WO 95/32710, published Dec. 7, 1995) 10% Pd/C (350 mg) and EtOH were stirred under 1 atm H$_2$. After 20 h, the reaction was filtered through a celite pad and then concentrated to provide ester A-5a as a brown oil.
TLC R$_f$=0.23 (silica, 40% EtOAc/hexanes)
$^1$H NMR (300 MHz, CDCl$_3$) δ 7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (A-6)

A suspension of ester A-5a (625 mg, 2.31 mmol) in 6N HCl (12 ml) was heated to 60° C. After ~20 h, the reaction was concentrated to give acid A-6 as a tan solid.
$^1$H NMR (300 MHz, CD$_3$OD) δ 7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2(S)-(4-iodo-phenylsulfonylamino)-β-alanine (A-7)

A solution of acid 15-6 (400 mg, 1.43 mmol), amine A4 (686 mg, 1.57 mmol), EDC (358 mg, 1.86 mmol), HOBT (252 mg, 1.86 mmol), NMM (632 μl, 5.72 mmol) in DMF (10 ml) was stirred for ~20 h. The reaction was diluted with EtOAc and then washed with sat. NaHCO$_3$, brine, dried (MgSO$_4$) and concentrated. Flash chromatography (silica, EtOAc then 5% isopropanol/EtOAc) provided amide A-7 as a white solid.
TLC R$_f$=0.4 (silica, 10% isopropanol/EtOAc)
$^1$H NMR (300 MHz, CD$_3$OD) δ 7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8 Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenyl-sulfonylamino)-β-alanine (A-8)

A solution of ester A-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/NH$_4$OH/H$_2$O) provided acid A-8 as a white solid.
TLC R$_f$=0.45 (silica, 20:20:1:1 EtOAc/EtOH/NH$_4$OH/H$_2$O)
$^1$H NMR (400 MHz, DMSO-d$_6$) δ 8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl)benzoyl-2(S)-(4trimethylstannyl-phenylsulfonylamino-β-alanine (A-9)

A solution of iodide A-8 (70 mg, 0.1178 mmol), [(CH$_3$)$_3$Sn]$_2$ (49 μl, 0.2356 mmol), Pd(PPh$_3$)$_4$ (5 mg) and dioxane (7 ml) was heated to 90° C. After 2 h, the reaction was concentrated and then purified by preparative HPLC (Delta-Pak C$_{18}$ 15 μM 100A°, 40×100 mm; 95:5 then 5:95 H$_2$O/CH$_3$CN) to provide the trifluoroacetate salt. The salt was suspended in H$_2$O (10 ml), treated with NH$_4$OH (5 drops) and then lyophilized to provide amide A-9 as a white solid.
$^1$H NMR (400 MHz, DMSO-d$_6$) δ 8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodo-phenylsulfonylamino-β-alanine (A-10)

An iodobead (Pierce) was added to a shipping vial of 5 mCi of Na$^{125}$I (Amersham, IMS30) and stirred for five minutes at room temperature. A solution of 0.1 mg of A-9 in 0.05 mL of 10% $H_2SO_4$/MeOH was made and immediately added to the $Na^{125}$I/iodobead vial. After stirring for three minutes at room temperature, approximately 0.04–0.05 mL of $NH_4OH$ was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):$H_2O$ (0.1% TFA) to 90% acetonitrile (0.1% TFA):$H_2O$ (0.1% TFA) over 30 minutes, 1 mL/min]. The retention time of A-10 is 17 minutes under these conditions. Fractions containing the majority of the radioactivity were pooled, lyophilized and diluted with ethanol to give approximately 1 mCi of A-10, which coeluted on HPLC analysis with an authentic sample of A-8.

Instrumentation

Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC, a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure $\alpha v\beta 3$ and $\alpha v\beta 5$ binding and the bone resorption inhibiting activity of the compounds of the present invention are described below.

BONE RESORPTION-PIT ASSAY

When osteoclasts engage in bone resorption, they can cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a 6 mm cylinder of bovine femur diaphysis are cut with a low speed diamond saw (Isomet, Beuler, Ltd., Lake Bluff, Ill). Bone slices are pooled, placed in a 10% ethanol solution and refrigerated until further use.

Prior to experimentation, bovine bone slices are ultrasonicated twice, 20 minutes each in $H_2O$. Cleaned slices are placed in 96 well plates such that two control lanes and one lane for each drug dosage are available. Each lane represents either triplicate or quadruplicate cultures. The bone slices in 96 well plates are sterilized by UV irradiation. Prior to incubation with osteoclasts, the bone slices are hydrated by the addition of 0.1 ml $\alpha$MEM, pH 6.9 containing 5% fetal bovine serum and 1% penicillin/streptomycin.

Long bones from 7–14 day old rabbits (New Zealand White Hare) are dissected, cleaned of soft tissue and placed in $\alpha$MEM containing 20 mM HEPES. The bones are minced using scissors until the pieces are <1 mm and transferred to a 50 ml tube in a volume of 25 ml. The tube is rocked gently by hand for 60 cycles, the tissue is sedimented for 1 min., and the supernatant is removed. Another 25 ml of medium is added to the tissue and rocked again. The second supernatant is combined with the first. The number of cells is counted excluding erythrocytes (typically $\sim 2\times 10^7$ cells/ml). A cell suspension consisting of $5\times 10^6$/ml in $\alpha$MEM containing 5% fetal bovine serum, 10 nM 1,25$(OH)_2D_3$, and pencillin-streptomycin is prepared. 200 ml aliquots are added to bovine bone slices (200 mm×6 mm) and incubated for 2 hrs. at 37° C. in a humidified 5% $CO_2$ atmosphere. The medium is removed gently with a micropipettor and fresh medium containing test compounds is added. The cultures are incubated for 48 hrs., and assayed for c-telopeptide (fragments of the a1 chain of type I collagen) by Crosslaps for culture media (Herlev, Denmark).

Bovine bone slices are exposed to osteoclasts for 20–24 hrs and are processed for staining. Tissue culture media is removed from each bone slice. Each well is washed with 200 ml of $H_2O$, and the bone slices are then fixed for 20 minutes in 2.5% glutaraldehyde, 0.1 M cacodylate, pH 7.4. After fixation, any remaining cellular debris is removed by 2 min. ultrasonication in the presence of 0.25 M $NH_4OH$ followed by 2×15 min ultrasonication in $H_2O$. The bone slices are immediately stained for 6–8 min with filtered 1% toluidine blue and 1% borax.

After the bone slices have dried, resorption pits are counted in test and control slices. Resorption pits are viewed in a Microphot Fx (Nikon) fluorescence microscope using a polarizing Nikon IGS filter cube. Test dosage results are compared with controls and resulting $IC_{50}$ values are determined for each compound tested.

The appropriateness of extrapolating data from this assay to mammalian (including human) disease states is supported by the teaching found in Sato, M., et al., *Journal of Bone and Mineral Research*, Vol. 5, No. 1, pp.31–40, 1990, which is incorporated by reference herein in its entirety. This article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8: S378 (1993) describes a system for expressing the human integrin $\alpha v\beta 3$. It has been suggested that the integrin stimulates attachment of osteoclasts to bone matrix, since antibodies against the integrin, or RGD-containing molecules, such as echistatin (European Publication 382 451), can effectively block bone resorption.

Reaction Mixture 1. 175 $\mu$l TBS buffer (50 mM Tris.HCl pH 7.2, 150 mM NaCl, 1% BSA, 1 mM $CaCl_2$, 1 mM $MgCl_2$).

2. 25 $\mu$l cell extract (dilute with 100 mM octylglucoside buffer to give 2000 cpm/25 $\mu$l).

3. $^{125}$I-echistatin (25 $\mu$l/50,000 cpm) (see EP 382 451).

4. 25 $\mu$l buffer (total binding) or unlabeled echistatin (non-specific binding).

The reaction mixture was then incubated for 1 h at room temp. The unbound and the bound $\alpha v\beta 3$ were separated by filtration using a Skatron Cell Harvester. The filters (prewet in 1.5% poly-ethyleneimine for 10 mins) were then washed with the wash buffer (50 mM Tris HCl, 1 mM $CaCl_2$/$MgCl_2$, pH 7.2). The filter was then counted in a gamma counter.

SPA ASSAY

Materials

1. Wheat germ agglutinin Scintillation Proximity Beads (SPA): Amersham

2. Octylglucopyranoside: Calbiochem

3. HEPES: Calbiochem

4. NaCl: Fisher

5. $CaCl_2$: Fisher

6. $MgCl_2$: SIGMA

7. Phenylmethylsulfonylfluoride (PMSF): SIGMA

8. Optiplate: PACKARD

9. Compound A-10 (specific activity 500–1000 Ci/mmole)

10. test compound

11. Purified integrin receptor: $\alpha_v\beta_3$ was purified from 293 cells overexpressing $\alpha_v\beta_3$ (Duong et al., *J. Bone Min. Res.*, 8:S378, 1993) according to Pytela (*Methods in Enzymology*, 144:475, 1987)

12. Binding buffer: 50 mM HEPES, pH 7.8, 100 mM NaCl, 1 mM $Ca^{2+}/Mg^{2+}$, 0.5 mM PMSF 13. 50 mM octylglucoside in binding buffer: 50-OG buffer

Procedure

1. Pretreatment of SPA Beads 500 mg of lyophilized SPA beads were first washed four times with 200 ml of 50-OG buffer and once with 100 ml of binding buffer, and then resuspended in 12.5 ml of binding buffer.

2. Preparation of SPA Beads and Receptor Mixture

In each assay tube, 2.5 $\mu$l (40 mg/ml) of pretreated beads were suspended in 97.5 $\mu$l of binding buffer and 20 $\mu$l of 50-OG buffer. 5 $\mu$l (~30 ng/$\mu$l) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 $\mu$l of binding buffer and 25 $\mu$l of 50-OG buffer.

3. Reaction

The following were sequentially added into Optiplate in corresponding wells:

(i) Receptor/beads mixture (75 ml)

(ii) 25 $\mu$l of each of the following: compound to be tested, binding buffer for total binding or A-8 for non-specific binding (final concentration 1 $\mu$M)

(iii) A-10 in binding buffer (25 $\mu$l, final concentration 40 pM)

(iv) Binding buffer (125 $\mu$l)

(v) Each plate was sealed with plate sealer from PACK-ARD and incubated overnight with rocking at 40° C.

4. Plates were counted using PACKARD TOPCOUNT

5. % inhibition was calculated as follows:

A=total counts

B=nonspecific counts

C=sample counts

% inhibition=[{(A−B)−(C−B)}/(A−B)]/(A−B)×100

OCFORM ASSAY

Osteoblast-like cells (1.8 cells), originally derived from mouse calvaria, were plated in CORNING 24 well tissue culture plates in αMEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 $\mu$m nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1\times10^6$ cells/mL. 50 $\mu$L was added to each well of 1.8 cells to yield 50,000 cells/well and 1,25-dihydroxy-vitamin $D_3$ ($D_3$) was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h., the medium was removed, cells were fixed with 10% formaldehyde in phosphate-buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS-MX phosphate. After staining, the plates were washed extensively with deionized water and air dried. The number of multinucleated, positive staining cells was counted in each well.

αvβ5 ATTACHMENT ASSAY

Duong et al., *J. Bone Miner. Res.*, 11: S290 (1996), describes a system for expressing the human (αvβ5 integrin receptor.

Materials

1. Media and solutions used in this assay are purchased from BRL/Gibco, except BSA and the chemicals are from Sigma.

2. Attachment medium: HBSS with 1 mg/ml heat-inactivated fatty acid free BSA and 2 mM $CaCl_2$.

3. Glucosaminidase substrate solution: 3.75 mM p-nitrophenyl N-acetyl-beta-D-glucosaminide, 0.1 M sodium citrate, 0.25% Triton, pH 5.0.

4. Glycine-EDTA developing solution: 50 mM glycine, 5 mM EDTA, pH 10.5.

Methods

1. Plates (96 well, Nunc Maxi Sorp) were coated overnight at 4° C. with human vitronectin (3 ug/ml) in 50 mM carbonate buffer (pH 9/0.6), using 100 $\mu$l/well. Plates were then washed 2× with DPBS and blocked with 2% BSA in DPBS for 2 h at room temperature. After additional washes (2×) with DPBS, plates were used for cell attachment assay.

2. 293 (αvβ5) cells were grown in MEM media in presence of 10% fetal calf serum to 90% confluence. Cells were then lifted from dishes with 1× Trypsin/EDTA and washed 3× with serum free MEM. Cells were resuspended in attachment medium ($3\times10^5$ cells/ml).

3. Test compounds were prepared as a series of dilutions at 2× concentrations and added as 50 $\mu$l/well. Cell suspension was then added as 50 $\mu$l/well. Plates were incubated at 37° C. with 55 $CO_2$ for 1 hour to allow attachment.

4. Non-adherent cells were removed by gently washing the plates (3×) with DPBS and then incubated with glucosaminidase substrate solution (100 μl/well), overnight at room temperature in the dark. To quantitate cell numbers, standard curve of glucosaminidase activity was determined for each experiment by adding samples of cell suspension directly to wells containing the enzyme substrate solution.

5. The next day, the reaction was developed by addition of 185 μl/well of glycine/EDTA solution and reading absorbance at 405 nm using a Molecular Devices V-Max plate reader. Average test absorbance values (4 wells per test samples) were calculated. Then, the number of attached cells at each drug concentration was quantitated versus the standard curve of cells using the Softmax program.

EXAMPLE OF A PHARMACEUTICAL FORMULATION

As a specific embodiment of an oral composition, 100 mg of a compound of the present invention are formulated with sufficient finely divided lactose to provide a total amount of 580 to 590 mg to fill a size O hard gel capsule.

Representative compounds of the present invention were tested and found to bind to human αvβ3 integrin. These compounds are generally found to have $IC_{50}$ values less than about 100 nM in the SPA assay.

Representative compounds of the present invention were tested and generally found to inhibit ≧50% the attachment of αvβ5 expressing cells to plates coated with vitronectin at concentrations of about 1 μM.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound having a structural formula selected from the group consisting of

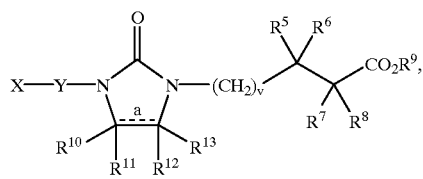

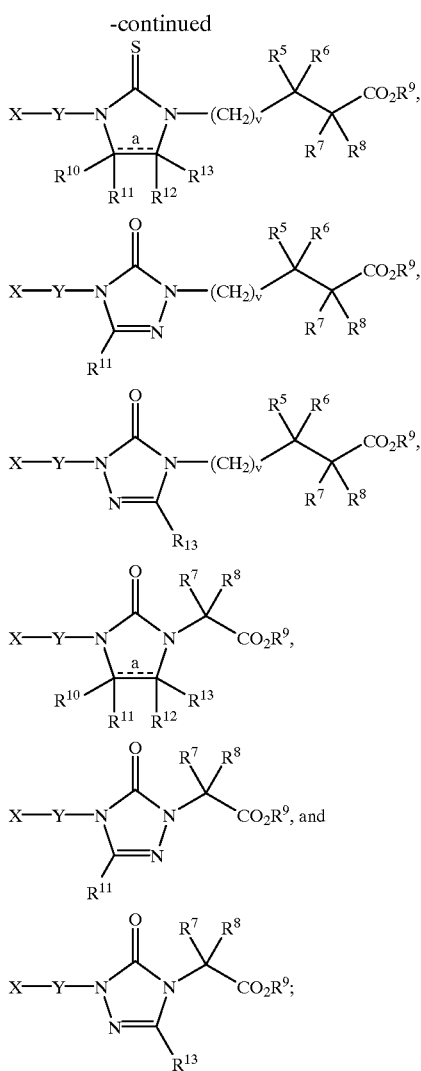

wherein the dotted line a represents a single or a double bond, provided that when a represents a double bond, the double bond carbon atoms are substituted only with $R^{10}$ and $R^{12}$;

X is selected from the group consisting of

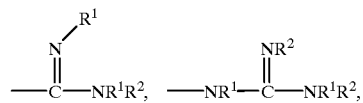

a 5- or 6-membered monocyclic aromatic or nonaromatic ring system having 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and a 9- to 14-membered polycyclic ring system, wherein one or more of the rings is aromatic, and wherein the polycyclic ring system has 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents;

Y is selected from the group consisting of

—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,
—$(CH_2)_m$—SO—$(CH_2)_n$—,
—$(CH_2)_m$—$SO_2$—$(CH_2)_n$—,
—$(CH_2)_m$—O—$(CH_2)_n$—O—$(CH_2)_p$—,
—$(CH_2)_m$—O—$(CH_2)_n$—$NR^4$—$(CH_2)_p$—,
—$(CH_2)_m$—$NR^4$—$(CH_2)_n$—$NR^4$—$(CH_2)_p$—,
—$(CH_2)_m$—O—$(CH_2)_n$—S—$(CH_2)_p$—,
—$(CH_2)_m$—S—$(CH_2)_n$—S—$(CH_2)_p$—,
—$(CH_2)_m$—$NR^4$—$(CH_2)_n$—O—$(CH_2)_p$—,
—$(CH_2)_m$—$NR^4$—$(CH_2)_n$—O—$(CH_2)_p$—,
—$(CH_2)_m$—S—$(CH_2)_n$—O—$(CH_2)_p$—,
—$(CH_2)_m$—S—$(CH_2)_n$—$NR^4$—$(CH_2)_p$—, and
—$(CH_2)_m$—Z—$(CH_2)_n$—, wherein Z is a 3- to 10-membered monocyclic or polycyclic aromatic or nonaromatic ring system having 0, 1, 2, 3, or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and wherein any methylene ($CH_2$) carbon atom in Y, other than in $R^4$, can be substituted by one or two $R^3$ substituents; and wherein $R^1$ and $R^2$ are each independently selected from the group consisting of hydrogen, halogen, $C_{1-10}$ alkyl, $C_{3-8}$ cycloalkyl, $C_{3-8}$ cycloheteroalkyl, $C_{3-8}$ cycloalkyl $C_{1-6}$ alkyl, $C_{3-8}$ cycloheteroalkyl $C_{1-6}$ alkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $(C_{1-6}$ alkyl$)_p$amino, $(C_{1-6}$ alkyl$)_p$amino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-$S(O)_p$, $(C_{1-8}$ alkyl$)_p$aminocarbonyl, $C_{1-8}$ alkyloxycarbonylamino, $(C_{1-8}$ alkyl$)_p$aminocarbonyloxy, (aryl $C_{1-8}$ alkyl$)_p$amino, (aryl$)_p$amino, aryl $C_{1-8}$ alkylsulfonylamino, and $C_{1-8}$ alkylsulfonylamino;

or two $R^1$ substituents, when on the same carbon atom, are taken together with the carbon atom to which they are attached to form a carbonyl group;

each $R^3$ is independently selected from the group consisting of hydrogen,
aryl,
$C_{1-10}$ alkyl,
aryl—$(CH_2)_r$—O—$(CH_2)_s$—,
aryl—$(CH_2)_r$$S(O)_p$—$(CH_2)_s$—,
aryl—$(CH_2)_r$—C(O)—$(CH_2)_s$—,
aryl—$(CH_2)_r$—C(O)—$N(R^4)$—$(CH_2)_s$—,
aryl—$(CH_2)_r$—$N(R^4)$—C(O)—$(CH_2)_s$—,
aryl—$(CH_2)_r$—$N(R^4)$—$(CH_2)_s$—,
halogen,
hydroxyl,
oxo,
trifluoromethyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl C1–6 alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
(aryl$)_p$amino,
(aryl$)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl, $C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$(C_{1-8}$ alkyl$)_p$aminocarbonyl $C_{1-6}$ alkyl,
$(aryl)_p$aminocarbonyl $C_{1-6}$ alkyl,
(aryl $C_{1-8}$ alkyl$)_p$aminocarbonyl, and
(aryl $C_{1-8}$ alkyl$)_p$aminocarbonyl $C_{1-6}$ alkyl;
or two $R^3$ substituents, when on the same carbon atom, are taken together with the carbon atom to which they are attached to form a carbonyl group or a cyclopropyl group, wherein any of the alkyl groups of $R^3$ are either unsubstituted or substituted with one to three $R^1$ substituents, provided that each $R^3$ is selected such that in the resultant compound the carbon atom or atoms to which $R^3$ is attached is itself attached to no more than one heteroatom;
each $R^4$ is independently selected from the group consisting of hydrogen,
aryl,
aminocarbonyl,
$C_{3-8}$ cycloalkyl,
amino $C_{1-6}$ alkyl,
$(aryl)_p$aminocarbonyl,
(aryl $C_{1-5}$ alkyl$)_p$aminocarbonyl,
hydroxycarbonyl $C_{1-6}$ alkyl,
$C_{1-8}$ alkyl,
aryl $C_{1-6}$ alkyl,
$(C_{1-6}$ alkyl$)_p$amino $C_{2-6}$ alkyl,
(aryl $C_{1-6}$ alkyl$)_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
$(C_{1-8}$ alkyl$)_p$aminocarbonyl,
aminosulfonyl,
$C_{1-8}$ alkylaminosulfonyl,
$(aryl)_p$aminosulfonyl,
(aryl $C_{1-8}$ alkyl$)_p$aminosulfonyl,
arylsulfonyl,
aryl$C_{1-6}$ alkylsulfonyl,
$C_{1-6}$ alkylthiocarbonyl,
arylthiocarbonyl, and
aryl $C_{1-6}$ alkylthiocarbonyl, wherein any of the alkyl groups of $R^4$ are either unsubstituted or substituted with one to three $R^1$ substituents;
$R^5$ and $R^6$ are each independently selected from the group consisting of hydrogen,
$C_{1-10}$ alkyl,
aryl,
aryl—$(CH_2)_r$—O—$(CH_2)_s$—,
aryl—$(CH_2)_r$S(O)$_p$—$(CH_2)_s$—,
aryl—$(CH_2)_r$—C(O)—$(CH_2)_s$—,
aryl—$(CH_2)_r$—C(O)—N($R^4$)—$(CH_2)_s$—,
aryl—$(CH_2)_r$—N($R^4$)—C(O)—$(CH_2)_s$—,
aryl—$(CH_2)_r$—N($R^4$)—$(CH_2)_s$—,
halogen,
hydroxyl,
$C_{1-8}$ alkylcarbonylamino,
aryl $C_{1-5}$ alkoxy,
$C_{1-5}$ alkoxycarbonyl,
$(C_{1-8}$ alkyl$)_p$aminocarbonyl,
$C_{1-6}$ alkylcarbonyloxy,
$C_{3-8}$ cycloalkyl,
$(C_{1-6}$ alkyl$)_p$amino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-6}$ alkoxy,
aryl $C_{1-6}$ alkoxy,
aryl $C_{1-6}$ alkyl,
$(C_{1-6}$ alkyl$)_p$amino $C_{1-6}$ alkyl,
$(aryl)_p$amino,
$(aryl)_p$amino $C_{1-6}$ alkyl,
(aryl $C_{1-6}$ alkyl$)_p$amino,
(aryl $C_{1-6}$ alkyl$)_p$amino $C_{1-6}$ alkyl,
arylcarbonyloxy,
aryl $C_{1-6}$ alkylcarbonyloxy,
$(C_{1-6}$ alkyl$)_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
$(aryl)_p$aminocarbonylamino $C_{1-6}$ alkyl,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl, (aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl, and
(aryl C$_{1-8}$ alkyl)$_p$aminocarbonyl C$_{1-6}$ alkyl;

or R$^5$ and R$^6$ are taken together with the carbon atom to which they are attached to form a carbonyl group,
wherein any of the alkyl groups of R$^5$ or R$^6$ are either unsubstituted or substituted with one to three R$^1$ substituents,
and provided that each R$^5$ and R$^6$ are selected such that in the resultant compound the carbon atom to which R$^5$ and R$^6$ are attached is itself attached to no more than one heteroatom;
R$^7$ and R$^8$ are each independently selected from the group consisting of hydrogen,
C$_{1-10}$ alkyl,
aryl,
aryl—(CH$_2$)$_r$—O—(CH$_2$)$_s$—,
aryl—(CH$_2$)$_r$S(O)$_p$—(CH$_2$)$_s$—,
aryl—(CH$_2$)$_r$—C(O)—(CH$_2$)$_s$—,
aryl—(CH$_2$)$_r$—C(O)—N(R$^4$)—(CH$_2$)$_s$—,
aryl—(CH$_2$)$_r$—N(R$^4$)—C(O)—(CH$_2$)$_2$—,
aryl—(CH$_2$)$_r$—N(R$^4$)—(CH$_2$)$_s$—,
halogen,
hydroxyl,
C$_{1-8}$ alkylcarbonylamino,
aryl C$_{1-5}$ alkoxy,
C$_{1-5}$ alkoxycarbonyl,
(C$_{1-8}$ alkyl)$_p$aminocarbonyl,
C$_{1-6}$ alkylcarbonyloxy,
C$_{3-8}$ cycloalkyl,
(C$_{1-6}$ alkyl)$_p$amino,
amino C$_{1-6}$ alkyl,
arylaminocarbonyl,
aryl C$_{1-5}$ alkylaminocarbonyl,
aminocarbonyl,
aminocarbonyl C$_{1-6}$ alkyl,
hydroxycarbonyl,
hydroxycarbonyl C$_{1-6}$ alkyl,
HC≡C—(CH$_2$)$_t$—,
C$_{1-6}$ alkyl—C≡C—(CH$_2$)$_t$—,
C$_{3-7}$ cycloalkyl—C≡C—(CH$_2$)$_t$—,
aryl—C≡C—(CH$_2$)$_t$—,
C$_{1-6}$ alkylaryl—C≡C—(CH$_2$)$_t$—,
CH$_2$=CH—(CH$_2$)$_t$—,
C$_{1-6}$ alkyl—CH=CH—(CH$_2$)$_t$—,
C$_{3-7}$ cycloalkyl—CH=CH—(CH$_2$)$_t$—,
aryl—CH=CH—(CH$_2$)$_t$—,
C$_{1-6}$ alkylaryl—CH=CH—(CH$_2$)$_t$—,
C$_{1-6}$ alkyl—SO$_2$—(CH$_2$)$_t$—,
C$_{1-6}$ alkylaryl—SO$_2$—(CH$_2$)$_t$—,
C$_{1-6}$ alkoxy,
aryl C$_{1-6}$ alkoxy,
aryl C$_{1-6}$ alkyl,
(C$_{1-6}$ alkyl)$_p$amino C$_{1-6}$ alkyl,
(aryl)$_p$amino,
(aryl)$_p$amino C$_{1-6}$ alkyl,
(aryl C$_{1-6}$ alkyl)$_p$amino,
(aryl C$_{1-6}$ alkyl)$_p$amino C$_{1-6}$ alkyl,
arylcarbonyloxy,
aryl C$_{1-6}$ alkylcarbonyloxy,
(C$_{1-6}$ alkyl)$_p$aminocarbonyloxy,
C$_{1-8}$ alkylsulfonylamino,
arylcarbonylamino,
arylsulfonylamino,
C$_{1-8}$ alkylsulfonylamino C$_{1-6}$ alkyl,
arylsulfonylamino C$_{1-6}$ alkyl,
aryl C$_{1-6}$ alkylsulfonylamino,
aryl C$_{1-6}$ alkylsulfonylamino C$_{1-6}$ alkyl,
C$_{1-8}$ alkoxycarbonylamino,
C$_{1-8}$ alkoxycarbonylamino C$_{1-8}$ alkyl,
aryloxycarbonylamino C$_{1-8}$ alkyl,
aryl C$_{1-8}$ alkoxycarbonylamino,
aryl C$_{1-8}$ alkoxycarbonylamino C$_{1-8}$ alkyl,
C$_{1-8}$ alkylcarbonylamino C$_{1-6}$ alkyl,
arylcarbonylamino C$_{1-6}$ alkyl,
aryl C$_{1-6}$ alkylcarbonylamino,
aryl C$_{1-6}$ alkylcarbonylamino C$_{1-6}$ alkyl,
aminocarbonylamino C$_{1-6}$ alkyl,
arylaminocarbonylamino,
(C$_{1-8}$ alkyl)$_p$aminocarbonylamino,
(C$_{1-8}$ alkyl)$_p$aminocarbonylamino C$_{1-6}$ alkyl,
(aryl)$_p$aminocarbonylamino C$_{1-6}$ alkyl,
(aryl C$_{1-8}$ alkyl)$_p$aminocarbonylamino,
(aryl C$_{1-8}$ alkyl)$_p$aminocarbonylamino C$_{1-6}$ alkyl,
aminosulfonylamino C$_{1-6}$ alkyl,
(C$_{1-8}$ alkyl)$_p$aminosulfonylamino,
(C$_{1-8}$ alkyl)$_p$aminosulfonylamino C$_{1-6}$ alkyl,
(aryl)$_p$aminosulfonylamino C$_{1-6}$ alkyl,
(aryl C$_{1-8}$ alkyl)$_p$aminosulfonylamino,
(aryl C$_{1-8}$ alkyl)$_p$aminosulfonylamino C$_{1-6}$ alkyl,
C$_{1-6}$ alkylsulfonyl,
C$_{1-6}$ alkylsulfonyl C$_{1-6}$ alkyl,
arylsulfonyl C$_{1-6}$ alkyl,
aryl C$_{1-6}$ alkylsulfonyl,
aryl C$_{1-6}$ alkylsulfonyl C$_{1-6}$ alkyl,
C$_{1-6}$ alkylcarbonyl,
C$_{1-6}$ alkylcarbonyl C$_{1-6}$ alkyl,
arylcarbonyl C$_{1-6}$ alkyl,
aryl C$_{1-6}$ alkylcarbonyl,
aryl C$_{1-6}$ alkylcarbonyl C$_{1-6}$ alkyl,
C$_{1-6}$ alkylthiocarbonylamino,
C$_{1-6}$ alkylthiocarbonylamino C$_{1-6}$ alkyl,
arylthiocarbonylamino C$_{1-6}$ alkyl,
aryl C$_{1-6}$ alkylthiocarbonylamino,
aryl C$_{1-6}$ alkylthiocarbonylamino C$_{1-6}$ alkyl,
(C$_{1-8}$ alkyl)$_p$aminocarbonyl C$_{1-6}$ alkyl,
(aryl)$_p$aminocarbonyl C$_{1-6}$ alkyl,
(aryl C$_{1-8}$ alkyl)$_p$aminocarbonyl,
(aryl C$_{1-8}$ alkyl)$_p$aminocarbonyl C$_{1-6}$ alkyl, and
C$_{7-20}$ polycyclyl C$_{0-8}$ alkylsulfonylamino;

wherein any of the alkyl groups of R$^7$ and R$^8$ are either unsubstituted or substituted with one to three R$^1$ substituents, and provided that each $R^7$ and $R^8$ are selected such that in the resultant compound the carbon atom to which $R^7$ and $R^8$ are attached is itself attached to no more than one heteroatom; $R^9$ is selected from the group consisting of hydrogen,
$C_{1-8}$ alkyl,
aryl,
aryl $C_{1-8}$ alkyl,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, and
$C_{1-8}$ dialkylaminocarbonylmethylene;

$R^{10}$, $R^{11}$, $R^{12}$ and $R^{13}$ are each independently selected from the group consisting of hydrogen,
$C_{1-8}$ alkyl,
aryl,
halogen,
hydroxyl,
aminocarbonyl,
$C_{3-8}$ cycloalkyl,
amino $C_{1-6}$ alkyl,
(aryl)$_p$aminocarbonyl,
hydroxycarbonyl,
(aryl $C_{1-5}$ alkyl)$_p$aminocarbonyl,
hydroxycarbonyl $C_{1-6}$ alkyl,
aryl $C_{1-6}$ alkyl,
($C_{1-6}$ alkyl)$_p$amino $C_{1-6}$ alkyl,
(aryl $C_{1-6}$ alkyl)$_p$amino $C_{2-6}$ alkyl,
$C_{1-8}$ alkylsulfonyl,
$C_{1-8}$ alkoxycarbonyl,
aryloxycarbonyl,
aryl $C_{1-8}$ alkoxycarbonyl,
$C_{1-8}$ alkylcarbonyl,
arylcarbonyl,
aryl $C_{1-6}$ alkylcarbonyl,
($C_{1-8}$ alkyl)$_p$aminocarbonyl,
aminosulfonyl,
$C_{1-8}$ alkylaminosulfonyl,
(aryl)$_p$aminosulfonyl,
(aryl $C_{1-8}$ alkyl)$_p$aminosulfonyl,
$C_{1-6}$ alkylsulfonyl,
arylsulfonyl,
aryl $C_{1-6}$ alkylsulfonyl,
aryl $C_{1-6}$ alkylcarbonyl,
$C_{1-6}$ alkylthiocarbonyl,
arylthiocarbonyl,
aryl $C_{1-6}$ alkylthiocarbonyl,
aryl—$(CH_2)_r$—O—$(CH_2)_s$—,
aryl—$(CH_2)_r$S(O)$_p$—$(CH_2)_s$—,
aryl—$(CH_2)_r$C(O)—$(CH_2)_s$—,
aryl—$(CH_2)_r$—C(O)—N($R^4$)—$(CH_2)_s$—,
aryl—$(CH_2)_r$—N($R^4$)—C(O)—$(CH_2)_s$—,
aryl—$(CH_2)_r$—N($R^4$)—$(CH_2)_s$—,
HC≡C—$(CH_2)_t$—,
$C_{1-6}$ alkyl—C≡C—$(CH_2)_t$—,
$C_{3-7}$ cycloalkyl—C≡C—$(CH_2)_t$—,
aryl—C≡C—$(CH_2)_t$—,
$C_{1-6}$ alkylaryl—C≡C—$(CH_2)_t$—,
$CH_2$=CH—$(CH_2)_t$—,
$C_{1-6}$ alkyl—CH=CH—$(CH_2)_t$—,
$C_{3-7}$ cycloalkyl—CH=CH—$(CH_2)_t$—,
aryl—CH=CH—$(CH_2)_t$—,
$C_{1-6}$ alkylaryl—CH=CH—$(CH_2)_t$—,
$C_{1-6}$ alkyl—$SO_2$—$(CH_2)_t$—,
$C_{1-6}$ alkylaryl—$SO_2$—$(CH_2)_t$—,
$C_{1-8}$ alkylcarbonylamino,
aryl $C_{1-5}$ alkoxy,
$C_{1-5}$ alkoxycarbonyl,
($C_{1-8}$ alkyl)$_p$aminocarbonyl,
$C_{1-6}$ alkylcarbonyloxy,
($C_{1-6}$ alkyl)$_p$amino,
aminocarbonyl $C_{1-6}$ alkyl,
$C_{1-6}$ alkoxy,
aryl $C_{1-6}$ alkoxy,
(aryl)$_p$amino,
(aryl)$_p$amino $C_{1-6}$ alkyl,
(aryl $C_{1-6}$ alkyl)$_p$amino,
(aryl $C_{1-6}$ alkyl)$_p$amino $C_{1-6}$ alkyl,
arylcarbonyloxy,
aryl $C_{1-6}$ alkylcarbonyloxy,
($C_{1-6}$ alkyl)$_p$aminocarbonyloxy,
$C_{1-8}$ alkylsulfonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
($C_{1-8}$ alkyl)$_p$aminocarbonylamino,
($C_{1-8}$ alkyl)$_p$aminocarbonylamino $C_{1-6}$ alkyl,
(aryl)$_p$aminocarbonylamino $C_{1-6}$ alkyl,
(aryl $C_{1-8}$ alkyl)$_p$aminocarbonylamino,
(aryl $C_{1-8}$ alkyl)$_p$aminocarbonylamino $C_{1-6}$ alkyl,
aminosulfonylamino $C_{1-6}$ alkyl,
($C_{1-8}$ alkyl)$_p$aminosulfonylamino,
($C_{1-8}$ alkyl)$_p$aminosulfonylamino $C_{1-6}$ alkyl,
(aryl)$_p$aminosulfonylamino $C_{1-6}$ alkyl,
(aryl $C_{1-8}$ alkyl)$_p$aminosulfonylamino,
(aryl $C_{1-8}$ alkyl)$_p$aminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
($C_{1-8}$ alkyl)$_p$aminocarbonyl $C_{1-6}$ alkyl,
(aryl)$_p$aminocarbonyl $C_{1-6}$ alkyl,
(aryl $C_{1-8}$ alkyl)$_p$aminocarbonyl, and
(aryl $C_{1-8}$ alkyl)$_p$aminocarbonyl $C_{1-6}$ alkyl; or
$R^{10}$ and $R^{12}$ are taken together with the carbon atoms to which they are attached to form a 5- to 7-membered monocyclic aromatic or nonaromatic ring system having 0, 1, 2, 3, or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents, and wherein any of the alkyl groups of $R^{10}$, $R^{11}$, $R^{12}$, and $R^{13}$ are either unsubstituted or substituted with one to three $R^1$ substituents;

wherein each m is independently an integer from 0 to 6;

each n is independently an integer from 0 to 6 each p is independently an integer from 0 to 2;

each r is independently an integer from 1 to 3;

each s is independently an integer from 0 to 3;

each t is independently an integer from 0 to 3; and each v is independently an integer from 0 to 2;

and the pharmaceutically acceptable salts thereof.

2. The compound of claim 1 having a structural formula selected from the group consisting of

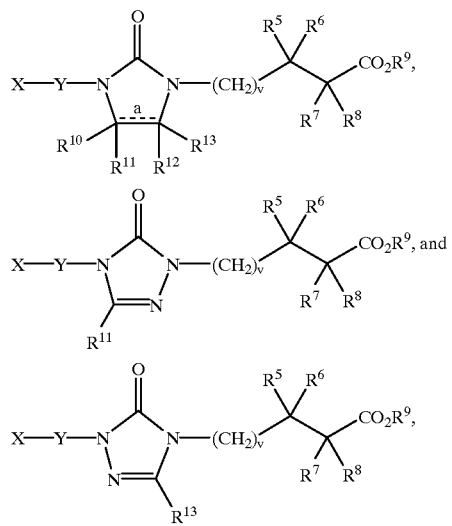

wherein the dotted line a represents a single or a double bond, provided that when a represents a double bond, the double bond carbon atoms are substituted only with $R^{10}$ and $R^{12}$;

X is a 6-membered monocyclic aromatic ring system having 1 or 2 nitrogen atoms wherein each ring carbon atom is unsubstituted or substituted with one $R^1$ substituent, or a 9- to 14-membered polycyclic ring system, wherein one or more of the rings is aromatic, and wherein the polycyclic ring system has 0, 1, 2, 3 or 4 heteroatoms selected from the group consisting of N, O, and S wherein the ring nitrogen atoms are unsubstituted or substituted with one $R^1$ substituent and the ring carbon atoms are unsubstituted or substituted with one or two $R^1$ substituents.

3. The compound of claim 2 having structural formula

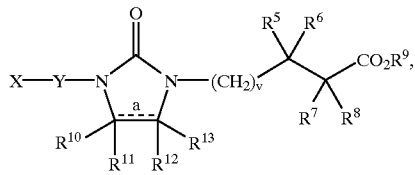

wherein the dotted line a represents a single or a double bond, provided that when a represents a double bond, the double bond carbon atoms are substituted only with $R^{10}$ and $R^{12}$; and X is selected from the group consisting of

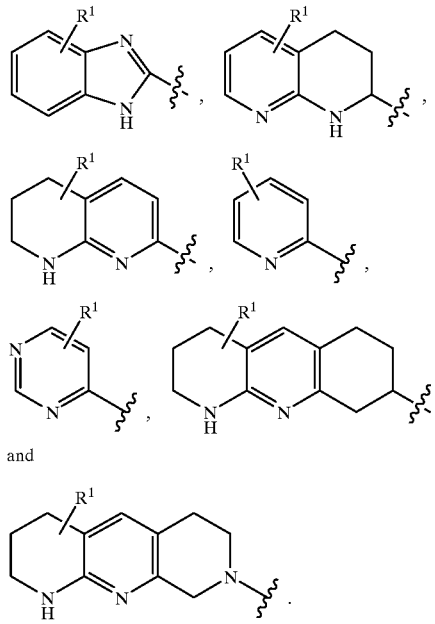

and

4. The compound of claim 3 having structural formula

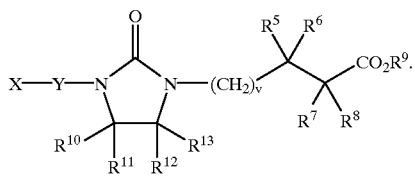

5. The compound of claim 4 wherein X is

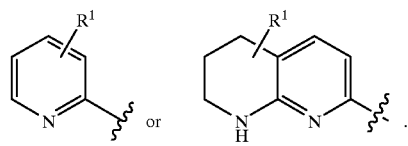

6. The compound of claim 5 wherein Y is selected from the group consisting of

—$(CH_2)_m$—,
—$(CH_2)_m$—O—$(CH_2)_n$—,
—$(CH_2)_m$—$NR^4$—$(CH_2)_n$—,
—$(CH_2)_m$—S—$(CH_2)_n$—,

—$(CH_2)_m$—SO—$(CH_2)_n$—,
—$(CH_2)_m$—$SO_2$—$(CH_2)_n$—,
—(CH2)m—O—(CH2)n—O—(CH2)p—,
—(CH2)m—O—(CH2)n—$NR^4$—(CH2)p—,
—(CH2)m—$NR^4$—(CH2)n—$NR^4$—(CH2)p—, and
—(CH2)m—$NR^4$—(CH2)n—O—(CH2)p—, wherein any methylene ($CH_2$) carbon atom in Y, other than in $R^4$, can be substituted by one or two $R^3$ substituents.

7. The compound of claim 6 wherein Y is selected from the group consisting of
$(CH_2)_m$, $(CH_2)_m$—S—$(CH_2)_n$, and $(CH_2)_m$—$NR^4$—$(CH_2)_n$,
wherein any methylene ($CH_2$) carbon atom in Y, other than in $R^4$, can be substituted by one or two $R^3$ substituents,
m and n are integers from 0–4,
and v is 0.

8. The compound of claim 7 wherein Y is
$(CH_2)_m$ or $(CH_2)_m$—$NR^4$—$(CH_2)_n$,
wherein any methylene ($CH_2$) group in Y, other than in $R^4$, can be substituted by one or two $R^3$ substituents.

9. The compound of claim 8 wherein each $R^3$ is independently selected from the group consisting of hydrogen,
fluoro,
trifluoromethyl,
aryl,
$C_{1-8}$ alkyl,
aryl$C_{1-6}$ alkyl
hydroxyl,
oxo,
arylaminocarbonyl,
aryl $C_{1-5}$ alkylaminocarbonyl,
aminocarbonyl, and
aminocarbonyl $C_{1-6}$ alkyl;

and each $R^4$ is independently selected from the group consisting of hydrogen,
aryl,
$C_{3-8}$ cycloalkyl,
$C_{1-8}$ alkyl,
$C_{1-8}$ alkylcarbonyl,
arylcarbonyl,
$C_{1-6}$ alkylsulfonyl,
arylsulfonyl,
aryl$C_{1-6}$alkylsulfonyl,
aryl$C_{1-6}$alkylcarbonyl,
$C_{1-8}$alkylaminocarbonyl,
aryl$C_{1-5}$alkylaminocarbonyl,
aryl$C_{1-8}$alkoxycarbonyl, and
$C_{1-8}$alkoxycarbonyl.

10. The compound of claim 9 wherein $R^6$, $R^7$, and $R^8$ are each hydrogen and $R^5$ is selected from the group consisting of hydrogen,
aryl,
$C_{1-8}$ alkyl,
aryl—C≡C—$(CH_2)_t$—,
aryl $C_{1-6}$ alkyl,
$CH_2$=CH—$(CH_2)_t$—, and
HC≡C—$(CH_2)_t$—.

11. The compound of claim 10 wherein $R^{10}$, $R^{11}$, $R^{12}$, and $R^{13}$ are each independently selected from the group consisting of hydrogen, aryl, $C_{1-6}$alkyl, and aryl$C_{1-6}$alkyl.

12. The compound of claim 10 wherein $R^9$ is selected from the group consisting of hydrogen, methyl, and ethyl.

13. The compound of claim 12 wherein $R^9$ is hydrogen.

14. The compound of claim 9 wherein $R^5$, $R^6$, and $R^8$ are each hydrogen and $R^7$ is selected from the group consisting of hydrogen,
aryl,
$C_{1-8}$ alkylcarbonylamino,
$C_{1-8}$ alkylsulfonylamino,
arylcarbonylamino,
arylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$(C_{1-8}$ alkyl$)_p$aminocarbonylamino,
$(C_{1-8}$ alkyl$)_p$aminocarbonylamino $C_{1-6}$ alkyl,
(aryl$)_p$aminocarbonylamino $C_{1-6}$ alkyl,
arylaminocarbonylamino,
(aryl $C_{1-8}$ alkyl$)_p$aminocarbonylamino,
(aryl $C_{1-8}$ alkyl$)_p$aminocarbonylamino $C_{1-6}$ alkyl,
aminosulfonylamino $C_{1-6}$ alkyl,
$(C_{1-8}$ alkyl$)_p$aminosulfonylamino,
$(C_{1-8}$ alkyl$)_p$aminosulfonylamino $C_{1-6}$ alkyl,
(aryl$)_p$aminosulfonylamino $C_{1-6}$ alkyl,
(aryl $C_{1-8}$ alkyl$)_p$aminosulfonylamino,
(aryl $C_{1-8}$ alkyl$)_p$aminosulfonylamino $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino, and
aryl $C_{1-6}$ alkylthiocarbonylamino $C_{1-6}$ alkyl.

15. The compound of claim 14 wherein $R^7$ is selected from the group consisting of hydrogen,
aryl,
$C_{1-8}$ alkylcarbonylamino,
aryl $C_{1-6}$ alkylcarbonylamino,
arylcarbonylamino,
$C_{1-8}$ alkylsulfonylamino,
aryl $C_{1-6}$ alkylsulfonylamino,
arylsulfonylamino,
$C_{1-8}$ alkoxycarbonylamino,
aryl $C_{1-8}$ alkoxycarbonylamino,
arylaminocarbonylamino,
$(C_{1-8}$ alkyl$)_p$aminocarbonylamino,
(aryl $C_{1-8}$ alkyl$)_p$aminocarbonylamino,
$(C_{1-8}$ alkyl$)_p$aminosulfonylamino, and
(aryl $C_{1-8}$ alkyl$)_p$aminosulfonylamino.

16. The compound of claim 15 wherein $R^{10}$, $R^{11}$, $R^{12}$, and $R^{13}$ are each independently selected from the group consisting of hydrogen, aryl, $C_{1-6}$alkyl, and aryl$C_{1-6}$ alkyl.

17. The compound of claim 15 wherein $R^9$ is selected from the group consisting of hydrogen, methyl, and ethyl.

18. The compound of claim 17 wherein $R^9$ is hydrogen.

19. The compound of claim 9 selected from the group consisting of

3(S)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3(R)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3(S)-(3-Fluorophenyl)-3-{2-oxo-3-[3-(5,6,7,8-tetrahydro-[1,8]naphthyridin-2-yl)-propyl]-imidazolidin-1-yl}-propionic acid, 3(R)-(3-Fluorophenyl)-3-{2-oxo-3-[3-(5,6,7,8-tetrahydro-[1,8]naphthyridin-2-yl)-propyl]-imidazolidin-1-yl}-propionic acid, 3-(3-Fluorophenyl)-3-{2-oxo-3-[3-(5,6,7,8-tetrahydro-[1,8]naphthyridin-2-yl)-propyl]-imidazolidin-1-yl}-propionic acid, 3(S)-(Quinolin-3-yl)-3-{2-oxo-3-[3-(5,6,7,8-tetrahydro-[1,8]naphthyridin-2-yl)-propyl]-imidazolidin-1-yl}-propionic acid, 3(R)-(Quinolin-3-yl)-3-{2-oxo-3-[3-(5,6,7,8-tetrahydro-[1,8]naphthyridin-2-yl)-propyl]-imidazolidin-1-yl}-propionic acid, 3-(Quinolin-3-yl)-3-{2-oxo-3-[3-(5,6,7,8-tetrahydro-[1,8]naphthyridin-2-yl)-propyl]-imidazolidin-1-yl}-propionic acid, 3(S)-(Ethynyl)-3-{2-oxo-3-[3-(5,6,7,8-tetrahydro-[1,8]naphthyridin-2-yl)-propyl]-imidazolidin-1-yl}-propionic acid, 3(R)-(Ethynyl)-3-{2-oxo-3-[3-(5,6,7,8-tetrahydro-[1,8]naphthyridin-2-yl)-propyl]-imidazolidin-1-yl}-propionic acid, 3-(Ethynyl)-3-{2-oxo-3-[3-(5,6,7,8-tetrahydro-[1,8]naphthyridin-2-yl)-propyl]-imidazolidin-1-yl}-propionic acid, 3(S)-(Pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(Pyridin-3-yl)-3-{2-oxo-3-[3-(5,6,7,8-tetrahydro-[1,8]naphthyridin-2-yl)-propyl]-imidazolidin-1-yl}-propionic acid, 3-(Pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(Pyridin-3-yl)-3-{2-oxo-3-[3-(5,6,7,8-tetrahydro-[1,8]naphthyridin-2-yl)-propyl]-4-methyl-imidazolidin-1-yl}-propionic acid, 3(R)-(Pyridin-3-yl)-3-{2-oxo-3-[3-(5,6,7,8-tetrahydro-[1,8]naphthyridin-2-yl)-propyl]-4-methyl-imidazolidin-1-yl}-propionic acid, 3-(Pyridin-3-yl)-3-{2-oxo-3-[3-(5,6,7,8-tetrahydro-[1,8]naphthyridin-2-yl)-propyl]-4-methyl-imidazolidin-1-yl}-propionic acid, 3(S)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, 3-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, trifluoroacetate salt, 3(S)-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, bis(trifluoroacetate) salt, 3(R)-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, 3-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, 3(S)-(6-Amino-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Amino-pyridin-3-yl)-3-{2-oxo-3-[3-(5,6,7,8-tetrahydro-[1,8]naphthyridin-2-yl)-propyl]-imidazolidin-1-yl}-propionic acid, 3-(6-Amino-pyridin-3-yl)-3-{2-oxo-3-[3-(5,6,7,8-tetrahydro-[1,8]naphthyridin-2-yl)-propyl]-imidazolidin-1-yl}-propionic acid, 3-(S)-(4-Methyl-3-oxo-3,4-dihydro-2H-benzo[1,4]oxazin-7-yl)-3-{2-oxo-3-[3-(5,6,7,8-tetrahydro-[1,8]naphthyridin-2-yl)-propyl]-imidazolidin-1-yl}-propionic acid, 3-(R)-(4-Methyl-3-oxo-3,4-dihydro-2H-benzo[1,4]oxazin-7-yl)-3-{2-oxo-3-[3-(5,6,7,8-tetrahydro-[1,8]naphthyridin-2-yl)-propyl]-imidazolidin-1-yl}-propionic acid, 3-(4-Methyl-3-oxo-3,4-dihydro-2H-benzo[1,4]oxazin-7-yl)-3-{2-oxo-3-[3-(5,6,7,8-tetrahydro-[1,8]naphthyridin-2-yl)-propyl]-imidazolidin-1-yl}-propionic acid, 3(S)-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid, 3-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(2-Fluoro-biphenyl-4-yl)-3-{2-oxo-3-[3-(5,6,7,8-tetrahydro-[1,8]naphthyridin-2-yl)-propyl]-imidazolidin-1-yl}-propionic acid, 3(R)-(2-Fluoro-biphenyl-4-yl)-3-{2-oxo-3-[3-(5,6,7,8-tetrahydro-[1,8]naphthyridin-2-yl)-propyl]-imidazolidin-1-yl}-propionic acid, 3-(2-Fluoro-biphenyl-4-yl)-3-{2-oxo-3-[3-(5,6,7,8-tetrahydro-[1,8]napthyridin-2-yl)-propyl]-imidazolidin-1-yl}-propionic acid, 3(S)-(2-Oxo-2,3-dihydro-benzoxazol-6-yl)-3-{2-oxo-3-[3-(5,6,7,8-tetrahydro-[1,8]napthyridin-2-yl)-propyl]-imidazolidin-1-yl}-propionic acid, 3(R)-(2-Oxo-2,3-dihydro-benzoxazol-6-yl)-3-{2-oxo-3-[3-(5,6,7,8-tetrahydro-[1,8]napthyridin-2-yl)-propyl]-imidazolidin-1-yl}-propionic acid, 3-(2-Oxo-2,3-dihydro-benzoxazol-6-yl)-3-{2-oxo-3-[3-(5,6,7,8-tetrahydro-[1,8]napthyridin-2-yl)-propyl]-imidazolidin-1-yl}-propionic acid, 3(S)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid, 3(R)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid, 3-(4Ethoxy-3-fluorophenyl)-3-{2-oxo-3-[3-(5,6,7,8-tetrahydro-[1,8]napthyridin-2-yl)-propyl]-imidazolidin-1-yl}-propionic acid, 3(S)-(5-Ethoxy-pyridin-3-yl)-3-{2-oxo-3-[3-(5,6,7,8-tetrahydro-[1,8]napthyridin-2-yl)-propyl]-imidazolidin-1-yl}-propionic acid, 3(R)-(5-Ethoxy-pyridin-3-yl)-3-{2-oxo-3-[3-(5,6,7,8-tetrahydro-[1,8]napthyridin-2-yl)-propyl]-imidazolidin-1-yl}-propionic acid, 3-(5-Ethoxy-pyridin-3-yl)-3-{2-oxo-3-[3-(5,6,7,8-tetrahydro-[1,8]napthyridin-2-yl)-propyl]-imidazolidin-1-yl}-propionic acid, 3(S)-(5-Hydroxy-pyridin-3-yl)-3-{2-oxo-3-[3-(5,6,7,8-tetrahydro-[1,8]napthyridin-2-yl)-propyl]-imidazolidin-1-yl}-propionic acid, 3(R)-(5-Hydroxy-pyridin-3-yl)-3-{2-oxo-3-[3-(5,6,7,8-tetrahydro-[1,8]napthyridin-2-yl)-propyl]-imidazolidin-1-yl}-propionic acid, 3-(5-Hydroxy-pyridin-3-yl)-3-{2-oxo-3-[3-(5,6,7,8-tetrahydro-[1,8]napthyridin-2-yl)-propyl]-imidazolidin-1-yl}-propionic acid, 2(S)-Benzenesulfonylamino-3-{2-oxo-3-[3-(5,6,7,8-tetrahydro-[1,8]napthyridin-2-yl)-propyl]-imidazolidin-1-yl}-propionic acid, 3(S)-{2-Oxo-3-[3-(5,6,7,8-tetrahydro-[1,8]naphthyridin-2-yl)-propyl]-imidazolidin-1-yl}-pent-4-enoic acid, 3(R)-{2-Oxo-3-[3-(5,6,7,8-tetrahydro-[1,8]naphthyridin-2-yl)-propyl]-imidazolidin-1-yl}-pent-4-enoic acid, 3-{2-Oxo-3-[3-(5,6,7,8-tetrahydro-[1,8]naphthyridin-2-yl)-propyl]-imidazolidin-1-yl}-pent-4-enoic acid, 3(S)-(5-Ethoxy-pyridin-3-yl)-3-(3-{3-[6-(4-methoxy-benzylamino)-pyridin-2-yl]-propyl}-2-oxo-imidazolidin-1-yl)-propionic acid, 3(R)-(5-Ethoxy-pyridin-3-yl)-3-(3-{3-[6-(4-methoxy-benzylamino)-pyridin-2-yl]-propyl}-2-oxo-imidazolidin-1-yl)-propionic acid, 3-(5-Ethoxy-pyridin-3-yl)-3-(3-{3-[6-(4-methoxy-benzylamino)-pyridin-2-yl]-propyl}-2-oxo-imidazolidin-1-yl)-propionic acid, 3-{3-[3-(6-Amino-pyridin-2-yl)-propyl]-2-oxo-imidazolidin-1-yl}-3(S)-(5-ethoxy-pyridin-3-yl)-propionic acid, 3-{3-[3-(6-Amino-pyridin-2-yl)-propyl]-2-oxo-imidazolidin-1-yl}-3(R)-(5-ethoxy-pyridin-3-yl)-propionic acid, 3-{3-[3-(6-Amino-pyridin-2-yl)-propyl]-2-oxo-imidazolidin-1-yl}-3-(5-ethoxy-pyridin-3-yl)-propionic acid, 3(S)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(S)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(S)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(S)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3(R)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid, 3-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Furo[2,3-b]pyridin-6-yl)-3-{2-oxo-3-[3-(5,6,7,8-tetrahydro-[1,8]naphthyridin-2-yl)propyl]imidazolidin-1-yl]propionic acid, 3(R)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid, 3-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid, 3-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(R)-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid, 3-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid, 3(S)-(Benzimidazol-2-yl)-3-(2-oxo-3-[3-(5,6,7,8-tetrahydro-[1,8]naphthyridin-2-yl)propyl]imidazolidin-1-yl)propionic acid, 3(R)-(Benzimidazol-2-yl)-3-(2-oxo-3-[3-(5,6,7,8-tetrahydro-[1,8]naphthyridin-2-yl)propyl]imidazolidin-1-yl)propionic acid, 3-(Benzimidazol-2-yl)-3-(2-oxo-3-[3-(5,6,7,8-tetrahydro-[1,8]naphthyridin-2-yl)propyl]imidazolidin-1-yl) propionic acid, 3(S)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid, 3(R)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid, 3-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid, 3(S)-(Benzoxazol-2-yl)-3-(2-oxo-3-[3-(5,6,7,8-tetrahydro-[1,8]naphthyridin-2-yl)propyl]imidazolidin-1-yl) propionic acid, 3(R)-(Benzoxazol-2-yl)-3-(2-oxo-3-[3-(5,6,7,8-tetrahydro-[1,8]naphthyridin-2-yl)propyl]imidazolidin-1-yl) propionic acid, 3-(Benzoxazol-2-yl)-3-(2-oxo-3-[3-(5,6,7,8-tetrahydro-[1,8]naphthyridin-2-yl)propyl]imidazolidin-1-yl)propionic acid, 3(S)-(1-Methyl-1H-pyrazol-4-yl)-3-(2-oxo-3-[3-(5,6,7,8-tetrahydro-[1,8]naphthyridin-2-yl)propyl]-imidazolidin-1-yl)propionic acid, 3(R)-(1-Methyl-1H-pyrazol-4-yl)-3-(2-oxo-3-[3-(5,6,7,8-tetrahydro-[1,8]naphthyridin-2-yl)propyl]-imidazolidin-1-yl)propionic acid, 3-(1-Methyl-1H-pyrazol-4-yl)-3-(2-oxo-3-[3-(5,6,7,8-tetrahydro-[1,8]naphthyridin-2-yl)propyl]-imidazolidin-1-yl)propionic acid, and the pharmaceutically acceptable salts thereof.

20. The compound of claim 19 selected from the group consisting of

3(S)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3(R)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3(S)-(3-Fluorophenyl)-3-{2-oxo-3-[3-(5,6,7,8-tetrahydro-[1,8]naphthyridin-2-yl)-propyl]-imidazolidin-1-yl}-propionic acid, 3(R)-(3-Fluorophenyl)-3-{2-oxo-3-[3-(5,6,7,8-tetrahydro-[1,8]naphthyridin-2-yl)-propyl]-imidazolidin-1-yl}-propionic acid, 3(S)-(Quinolin-3-yl)-3-{2-oxo-3-[3-(5,6,7,8-tetrahydro-[1,8]naphthyridin-2-yl)-propyl]-imidazolidin-1-yl}-propionic acid, 3(R)-(Quinolin-3-yl)-3-{2-oxo-3-[3-(5,6,7,8-tetrahydro-[1,8]naphthyridin-2-yl)-propyl]-imidazolidin-1-yl}-propionic acid, 3(S)-(Ethynyl)-3-{2-oxo-3-[3-(5,6,7,8-tetrahydro-[1,8]naphthyridin-2-yl)-propyl]-imidazolidin-1-yl}-propionic acid, 3(R)-(Ethynyl)-3-{2-oxo-3-[3-(5,6,7,8-tetrahydro-[1,8]naphthyridin-2-yl)-propyl]-imidazolidin-1-yl}-propionic acid, 3(S)-(Pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(Pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(Pyridin-3-yl)-3-{2-oxo-3-[3-(5,6,7,8-tetrahydro-[1,8]naphthyridin-2-yl)-propyl]-4-methyl-imidazolidin-1-yl}-propionic acid, 3(R)-(Pyridin-3-yl)-3-{2-oxo-3-[3-(5,6,7,8-tetrahydro-[1,8]naphthyridin-2-yl)-propyl]-4-methyl-imidazolidin-1-yl}-propionic acid, 3(S)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, bis(trifluoroacetate) salt, 3(R)-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, 3(S)-(6-Amino-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Amino-pyridin-3-yl)-3-{2-oxo-3-[3-(5,6,7,8-tetrahydro-[1,8]naphthyridin-2-yl)-propyl]-imidazolidin-1-yl}-propionic acid, 3-(S)-(4-Methyl-3-oxo-3,4-dihydro-2H-benzo[1,4]oxazin-7-yl)-3-{2-oxo-3-[3-(5,6,7,8-tetrahydro-[1,8]naphthyridin-2-yl)-propyl]-imidazolidin-1-yl}-propionic acid, 3-(R)-(4-Methyl-3-oxo-3,4-dihydro-2H-benzo[1,4]oxazin-7-yl)-3-{2-oxo-3-[3-(5,6,7,8-tetrahydro-[1,8]naphthyridin-2-yl)-propyl]-imidazolidin-1-yl}-propionic acid, 3(S)-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(2-Fluoro-biphenyl-4-yl)-3-{2-oxo-3-[3-(5,6,7,8-tetrahydro-[1,8]napthyridin-2-yl)-propyl]-imidazolidin-1-yl}-propionic acid, 3(R)-(2-Fluoro-biphenyl-4-yl)-3-{2-oxo-3-[3-(5,6,7,8-tetrahydro-[1,8]napthyridin-2-yl)-propyl]-imidazolidin-1-yl}-propionic acid, 3(S)-(2-Oxo-2,3-dihydro-benzoxazol-6-yl)-3-{2-oxo-3-[3-(5,6,7,8-tetrahydro-[1,8]napthyridin-2-yl)-propyl]-imidazolidin-1-yl}-propionic acid, 3(R)-(2-Oxo-2,3-dihydro-benzoxazol-6-yl)-3-{2-oxo-3-[3-(5,6,7,8-tetrahydro-[1,8]napthyridin-2-yl)-propyl]-imidazolidin-1-yl}-propionic acid, 3(S)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid, 3(R)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid, 3(S)-(5-Ethoxy-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(5-Ethoxy-pyridin-3-yl)-3-{2-oxo-3-[3-(5,6,7,8-tetrahydro-[1,8]naphthyridin-2-yl)-propyl]-imidazolidin-1-yl}-propionic acid, 3(S)-(5-Hydroxy-pyridin-3-yl)-3-{2-oxo-3-[3-(5,6,7,8-tetrahydro-[1,8]naphthyridin-2-yl)-propyl]-imidazolidin-1-yl}-propionic acid, 3(R)-(5-Hydroxy-pyridin-3-yl)-3-{2-oxo-3-[3-(5,6,7,8-tetrahydro-[1,8]naphthyridin-2-yl)-propyl]-imidazolidin-1-yl}-propionic acid, 3(S)-{2-Oxo-3-[3-(5,6,7,8-tetrahydro-[1,8]naphthyridin-2-yl)-propyl]-imidazolidin-1-yl}-pent-4-enoic acid,
3(R)-{2-Oxo-3-[3-(5,6,7,8-tetrahydro-[1,8]naphthyridin-2-yl)-propyl]-imidazolidin-1-yl}-pent-4-enoic acid,
3(S)-(5-Ethoxy-pyridin-3-yl)-3-(3-{3-[6-(4-methoxy-benzylamino)-pyridin-2-yl]-propyl}-2-oxo-imidazolidin-1-yl)-propionic acid,
3(R)-(5-Ethoxy-pyridin-3-yl)-3-(3-{3-[6-(4-methoxy-benzylamino)-pyridin-2-yl]-propyl}-2-oxo-imidazolidin-1-yl)-propionic acid,
3-{3-[3-(6-Amino-pyridin-2-yl)-propyl]-2-oxo-imidazolidin-1-yl}-3(S)-(5-ethoxy-pyridin-3-yl)-propionic acid,
3-{3-[3-(6-Amino-pyridin-2-yl)-propyl]-2-oxo-imidazolidin-1-yl}-3(R)-(5-ethoxy-pyridin-3-yl)-propionic acid,
3(S)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(R)-(2-Oxo-2,3-dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(S)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(R)-(2,3-Dihydro-1H-4-oxa-1,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(S)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(R)-(3-Oxo-3,4-dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(S)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(R)-(3,4-Dihydro-2H-1-oxa-4,5-diaza-naphthalen-7-yl)-3-{2-oxo-3-[3-(5,6,7,8-tetrahydro-[1,8]naphthyridin-2-yl)propyl]-imidazolidin-1-yl}propionic acid,
3(S)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid,
3(R)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid,
3(S)-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid,
3(R)-(2,3-Dihydrofuro[2,3-b]pyridin-6-yl)-3-{2-oxo-3-[3-(5,6,7,8-tetrahydro-[1,8]naphthyridin-2-yl)propyl]imidazolidin-1-yl}propionic acid,
3(S)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid,
3(R)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid,
3(S)-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid,
3(R)-(2,3-Dihydrofuro[3,2-b]pyridin-6-yl)-3-{2-oxo-3-[3-(5,6,7,8-tetrahydro-[1,8]naphthyridin-2-yl)propyl]imidazolidin-1-yl}propionic acid,
3(S)-(Benzimidazol-2-yl)-3-(2-oxo-3-[3-(5,6,7,8-tetrahydro-[1,8]naphthyridin-2-yl)propyl]imidazolidin-1-yl)propionic acid,
3(R)-(Benzimidazol-2-yl)-3-(2-oxo-3-[3-(5,6,7,8-tetrahydro-[1,8]naphthyridin-2-yl)propyl]imidazolidin-1-yl)propionic acid,
3(S)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid,
3(R)-(1H-Imidazo[4,5-c]pyridin-2-yl)-3-(2-oxo-3-[3-(5,6,7,8-tetrahydro-[1,8]naphthyridin-2-yl)propyl]-imidazolidin-1-yl)propionic acid,
3(S)-(Benzoxazol-2-yl)-3-(2-oxo-3-[3-(5,6,7,8-tetrahydro-[1,8]naphthyridin-2-yl)propyl]imidazolidin-1-yl) propionic acid,
3(R)-(Benzoxazol-2-yl)-3-(2-oxo-3-[3-(5,6,7,8-tetrahydro-[1,8]naphthyridin-2-yl)propyl]imidazolidin-1-yl) propionic acid,
3(S)-(1-Methyl-1H-pyrazol-4-yl)-3-(2-oxo-3-[3-(5,6,7,8-tetrahydro-[1,8]naphthyridin-2-yl)propyl]-imidazolidin-1-yl)propionic acid,
3(R)-(1-Methyl-1H-pyrazol-4-yl)-3-(2-oxo-3-[3-(5,6,7,8-tetrahydro-[1,8]naphthyridin-2-yl)propyl]-imidazolidin-1-yl)propionic acid, and the pharmaceutically acceptable salts thereof.

21. The compound of claim 20 selected from the group consisting of

3(S)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid,
3(S)-(Quinolin-3-yl)-3-{2-oxo-3-[3-(5,6,7,8-tetrahydro-[1,8]naphthyridin-2-yl)-propyl]-imidazolidin-1-yl}-propionic acid,
3(S)-(Pyridin-3-yl)-3-{2-oxo-3-[3-(5,6,7,8-tetrahydro-[1,8]naphthyridin-2-yl)-propyl]-imidazolidin-1-yl}-propionic acid,
3(S)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid,
3(S)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid,
3(S)-(4-Methoxyquinolin-7-yl)-3-{2-oxo-3-[3-(5,6,7,8-tetrahydro-[1,8]naphthyridin-2-yl)-propyl]-imidazolidin-1-yl}-propionic acid, bis(trifluoroacetate) salt,
3(S)-(6-Methylamino-pyridin-3-yl)-3-{2-oxo-3-[3-(5,6,7,8-tetrahydro-[1,8]naphthyridin-2-yl)-propyl]-imidazolidin-1-yl}-propionic acid,
3(S)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid,
3(S)-(Furo[2,3-b]pyridin-6-yl)-3-{2-oxo-3-[3-(5,6,7,8-tetrahydro-[1,8]naphthyridin-2-yl)propyl]imidazolidin-1-yl}propionic acid,
3(S)-(Furo[3,2-b]pyridin-6-yl)-3-{2-oxo-3-[3-(5,6,7,8-tetrahydro-[1,8]naphthyridin-2-yl)propyl]imidazolidin-1-yl}propionic acid,
3(S)-(Benzimidazol-2-yl)-3-(2-oxo-3-[3-(5,6,7,8-tetrahydro-[1,8]naphthyridin-2-yl)propyl]imidazolidin-1-yl)propionic acid,
3(S)-(Benzoxazol-2-yl)-3-(2-oxo-3-[3-(5,6,7,8-tetrahydro-[1,8]naphthyridin-2-yl)propyl]imidazolidin-1-yl) propionic acid, and the pharmaceutically acceptable salts thereof.

22. A pharmaceutical composition comprising a compound according to claim 1 and a pharmaceutically acceptable carrier.

23. A pharmaceutical composition made by combining a compound according to claim 1 and a pharmaceutically acceptable carrier.

24. A process for making a pharmaceutical composition comprising combining a compound according to claim 1 and a pharmaceutically acceptable carrier.

25. The composition of claim 22 which further comprises an active ingredient selected from the group consisting of
   a) an organic bisphosphonate or a pharmaceutically acceptable salt or ester thereof,
   b) an estrogen receptor modulator,
   c) a cytotoxic/antiproliferative agent,
   d) a matrix metalloproteinase inhibitor,
   e) an inhibitor of epidermal-derived, fibroblast-derived, or platelet-derived growth factors,
   f) an inhibitor of VEGF,
   g) an inhibitor of Flk-1/KDR, Flt-1, Tck/Tie-2, or Tie-1,
   h) a cathepsin K inhibitor, and
   i) a prenylation inhibitor, such as a farnesyl transferase inhibitor or a geranylgeranyl transferase inhibitor or a dual farnesyl/geranylgeranyl transferase inhibitor;
   and mixtures thereof.

26. The composition of claim 25 wherein said active ingredient is selected from the group consisting of
   a) an organic bisphosphonate or a pharmaceutically acceptable salt or ester thereof,
   b) an estrogen receptor modulator, and
   c) a cathepsin K inhibitor;
   and mixtures thereof.

27. The composition of claim 26 wherein said organic bisphosphonate or pharmaceutically acceptable salt or ester thereof is alendronate monosodium trihydrate.

28. The composition of claim 25 wherein said active ingredient is selected from the group consisting of
   a) a cytotoxic/antiproliferative agent,
   b) a matrix metalloproteinase inhibitor,
   c) an inhibitor of epidermal-derived, fibroblast-derived, or platelet-derived growth factors,
   d) an inhibitor of VEGF, and
   e) an inhibitor of Flk-1/KDR, Flt-1, Tck/Tie-2, or Tie-1;
   and mixtures thereof.

29. A method of eliciting an integrin receptor antagonizing effect in a mammal in need thereof, comprising administering to the mammal a therapeutically effective amount of a compound according to claim 1.

30. The method of claim 29 wherein the integrin receptor antagonizing effect is an $\alpha v\beta 3$ antagonizing effect.

31. The method of claim 30 wherein the $\alpha v\beta 3$ antagonizing effect is selected from the group consisting of inhibition of bone resorption, restenosis, angiogenesis, diabetic retinopathy, macular degeneration, inflammation, viral disease, and tumor growth.

32. The method of claim 31 wherein the $\alpha v\beta 3$ antagonizing effect is the inhibition of bone resorption.

33. The method of claim 29 wherein the integrin receptor antagonizing effect is an $\alpha v\beta 5$ antagonizing effect.

34. The method of claim 33 wherein the $\alpha v\beta 5$ antagonizing effect is selected from the group consisting of inhibition of restenosis, angiogenesis, diabetic retinopathy, macular degeneration, inflammation, and tumor growth.

35. The method of claim 29 wherein the integrin receptor antagonizing effect is a dual $\alpha v\beta 3/\alpha v\beta 5$ antagonizing effect.

36. The method of claim 35 wherein the dual $\alpha v\beta 3/\alpha v\beta 5$ antagonizing effect is selected from the group consisting of inhibition of bone resorption, restenosis, angiogenesis, diabetic retinopathy, macular degeneration, inflammation, viral disease, and tumor growth.

37. The method of claim 29 wherein the integrin antagonizing effect is an $\alpha v\beta 6$ antagonizing effect.

38. The method of claim 37 wherein the $\alpha v\beta 6$ antagonizing effect is selected from the group consisting of angiogenesis, inflammatory response, and wound healing.

39. A method of eliciting an integrin receptor antagonizing effect in a mammal in need thereof, comprising administering to the mammal a therapeutically effective amount of the composition of claim 22.

40. A method of treating or preventing a condition mediated by antagonism of an integrin receptor in a mammal in need thereof, comprising administering to the mammal a therapeutically effective amount of the composition of claim 22.

41. A method of inhibiting bone resorption in a mammal in need thereof, comprising administering to the mammal a therapeutically effective amount of the composition of claim 22.

42. A method of inhibiting bone resorption in a mammal in need thereof, comprising administering to the mammal a therapeutically effective amount of the composition of claim 26.

43. A method of treating tumor growth in a mammal in need thereof, comprising administering to the mammal a therapeutically effective amount of the composition of claim 28.

44. A method of treating tumor growth in a mammal in need thereof, comprising administering to the mammal a therapeutically effective amount of a compound according to claim 1 in combination with radiation therapy.

45. The compound of claim 21 selected from the group consisting of

3(S)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid, 3(S)-(Quinolin-3-yl)-3-{2-oxo-3-[3-(5,6,7,8-tetrahydro-[1,8]naphthyridin-2-yl)-propyl]-imidazolidin-1-yl}-propionic acid, 3(S)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(6-Ethoxypyridin-3-yl)-3-{2-oxo-3-[3-(5,6,7,8-tetrahydro-[1,8]naphthyridin-2-yl)-propyl]-imidazolidin-1-yl}-propionic acid, 3(S)-(4-Ethoxy-3-fluorophenyl)-3-{2-oxo-3-[3-(5,6,7,8-tetrahydro-[1,8]napthyridin-2-yl)-propyl]-imidazolidin-1-yl}-propionic acid;

and the pharmaceutically acceptable salts thereof.

46. The compound of claim 45 which is

3(S)-(2,3-Dihydro-benzofuran-6-yl)-3-{2-oxo-3-[3-(5,6,7,8-tetrahydro-[1,8]naphthyridin-2-yl)-propyl]-imidazolidin-1-yl}-propionic acid or a pharmaceutically acceptable salt thereof.

47. The compound of claim 45 which is

3(S)-(6-Methoxypyridin-3-yl)-3-{2-oxo-3-[3-(5,6,7,8-tetrahydro-[1,8]naphthyridin-2-yl)-propyl]-imidazolidin-1-yl}-propionic acid or a pharmaceutically acceptable salt thereof.

48. The compound of claim 45 which is

3(S)-(Quinolin-3-yl)-3-{2-oxo-3-[3-(5,6,7,8-tetrahydro-[1,8]naphthyridin-2-yl)-propyl]-imidazolidin-1-yl}-propionic acid or a pharmaceutically acceptable salt thereof.

* * * * *